(12) United States Patent
Baldwin

(10) Patent No.: US 11,944,339 B2
(45) Date of Patent: *Apr. 2, 2024

(54) MINIMALLY INVASIVE SURGICAL DEVICES AND METHODS

(71) Applicant: FACULTY PHYSICIANS AND SURGEONS OF LOMA LINDA UNIVERSITY OF MEDICINE, Loma Linda, CA (US)

(72) Inventor: Dalton Duane Baldwin, Loma Linda, CA (US)

(73) Assignee: FACULTY PHYSICIANS AND SURGEONS OF LOMA LINDA UNIVERSITY OF MEDICINE, Loma Linda, CA (US)

( * ) Notice: Subject to any disclaimer, the term of this patent is extended or adjusted under 35 U.S.C. 154(b) by 394 days.

This patent is subject to a terminal disclaimer.

(21) Appl. No.: 16/949,981

(22) Filed: Nov. 23, 2020

(65) Prior Publication Data

US 2021/0093310 A1    Apr. 1, 2021

Related U.S. Application Data

(63) Continuation of application No. 16/057,244, filed on Aug. 7, 2018, now Pat. No. 10,842,474, which is a
(Continued)

(51) Int. Cl.
*A61B 17/29* (2006.01)
*A61B 17/00* (2006.01)
(Continued)

(52) U.S. Cl.
CPC ............... *A61B 17/320016* (2013.01); *A61B 17/00234* (2013.01); *A61B 17/083* (2013.01);
(Continued)

(58) Field of Classification Search
CPC . A61B 17/28; A61B 17/29; A61B 2017/2901; A61B 2017/2902;
(Continued)

(56) References Cited

U.S. PATENT DOCUMENTS 5,441,059 A    8/1995   Dannan
6,309,397 B1  10/2001   Julian et al.
(Continued)

FOREIGN PATENT DOCUMENTS

CA    2762552    12/2010
EP    2432372     3/2012
(Continued)

OTHER PUBLICATIONS

Extended European Search Report issued in corresponding European Application No. 14782807.3 dated Oct. 13, 2016.
(Continued)

*Primary Examiner* — Martin T Ton
(74) *Attorney, Agent, or Firm* — Womble Bond Dickinson (US) LLP

(57) ABSTRACT

Surgical tools for use during scarless or near scarless surgical procedures. At least some of the surgical tools can include a handle portion and a working end removably connected to the handle portion.

10 Claims, 53 Drawing Sheets

Related U.S. Application Data continuation of application No. 14/639,551, filed on Mar. 5, 2015, now Pat. No. 10,299,771, which is a continuation of application No. 14/250,244, filed on Apr. 10, 2014, now Pat. No. 8,992,566.

(60) Provisional application No. 61/811,092, filed on Apr. 11, 2013.

(51) Int. Cl.
| | |
|---|---|
| *A61B 17/08* | (2006.01) |
| *A61B 17/128* | (2006.01) |
| *A61B 17/32* | (2006.01) |
| *A61B 17/3201* | (2006.01) |
| *A61B 17/34* | (2006.01) |
| *A61B 90/00* | (2016.01) |
| *A61M 1/00* | (2006.01) |
| *A61B 17/30* | (2006.01) |
| *A61B 18/00* | (2006.01) |
| *A61B 18/14* | (2006.01) |
| *A61B 34/30* | (2016.01) |

(52) U.S. Cl.
CPC ........ *A61B 17/128* (2013.01); *A61B 17/1285* (2013.01); *A61B 17/29* (2013.01); *A61B 17/2909* (2013.01); *A61B 17/3201* (2013.01); *A61B 17/3421* (2013.01); *A61B 90/361* (2016.02); *A61M 1/86* (2021.05); *A61B 2017/00292* (2013.01); *A61B 2017/00477* (2013.01); *A61B 2017/2901* (2013.01); *A61B 2017/2931* (2013.01); *A61B 2017/306* (2013.01); *A61B 2017/3443* (2013.01); *A61B 2017/3454* (2013.01); *A61B 2018/00982* (2013.01); *A61B 2018/1422* (2013.01); *A61B 18/1477* (2013.01); *A61B 34/30* (2016.02); *A61B 2217/007* (2013.01); *Y10T 29/49826* (2015.01)

(58) Field of Classification Search
CPC ...... A61B 2017/291; A61B 2017/2912; A61B 2017/2913; A61B 2017/2916; A61B 2017/2932; A61B 2017/2933; A61B 2017/2936; A61B 2017/294
USPC ....................................................... 606/205
See application file for complete search history.

(56) References Cited

U.S. PATENT DOCUMENTS

| | | | |
|---|---|---|---|
| 7,666,181 B2 | 2/2010 | Abou El Kheir | |
| 7,927,327 B2* | 4/2011 | Lu ........................ | A61B 17/221 606/1 |
| 8,225,798 B2 | 7/2012 | Baldwin et al. | |
| 8,721,539 B2 | 5/2014 | Shohat et al. | |
| 8,828,046 B2 | 9/2014 | Stefanchik et al. | |
| 8,858,538 B2 | 10/2014 | Belson et al. | |
| 8,887,750 B2 | 11/2014 | Stefan et al. | |
| 8,992,566 B2 | 3/2015 | Baldwin | |
| 9,795,449 B2 | 10/2017 | Baldwin | |
| 10,299,771 B2 | 5/2019 | Baldwin | |
| 2006/0200186 A1 | 9/2006 | Marchek et al. | |
| 2008/0027279 A1 | 1/2008 | Abou El Kheir | |
| 2008/0319455 A1 | 12/2008 | Harris et al. | |
| 2009/0062792 A1 | 3/2009 | Vakharia et al. | |
| 2010/0179540 A1 | 7/2010 | Marczyk et al. | |
| 2010/0298774 A1 | 11/2010 | Igov | |
| 2011/0087267 A1* | 4/2011 | Spivey ................. | A61B 17/29 606/1 |
| 2011/0152887 A1* | 6/2011 | Surti ................... | A61B 17/122 606/142 |
| 2011/0264136 A1 | 10/2011 | Choi et al. | |
| 2012/0078292 A1 | 3/2012 | Banju | |
| 2012/0083826 A1 | 4/2012 | Chao et al. | |
| 2012/0165611 A1 | 6/2012 | Warren et al. | |
| 2012/0259317 A1 | 10/2012 | Baldwin et al. | |
| 2013/0066304 A1 | 3/2013 | Belson et al. | |
| 2014/0052061 A1* | 2/2014 | Weisshaupt .......... | A61B 1/0055 604/95.04 |
| 2014/0309677 A1 | 10/2014 | Baldwin | |
| 2018/0344306 A1 | 12/2018 | Baldwin | |

FOREIGN PATENT DOCUMENTS

| | | |
|---|---|---|
| WO | 2010068004 | 6/2010 |
| WO | 2010114634 | 10/2010 |
| WO | 2010144219 | 12/2010 |
| WO | WO2012040183 | 3/2012 |
| WO | 2012051188 | 4/2012 |
| WO | 2012112622 | 8/2012 |
| WO | 2013036024 | 3/2013 |
| WO | 2014169132 | 10/2014 |

OTHER PUBLICATIONS

Korean Intellectual Property Office, International Search Report and Written Opinion for International Patent Application No. PCT/US2014/033664, dated Sep. 4, 2014.
EPO Examination Report for European Patent Application No. 14782807.3, dated Nov. 14, 2019.

* cited by examiner

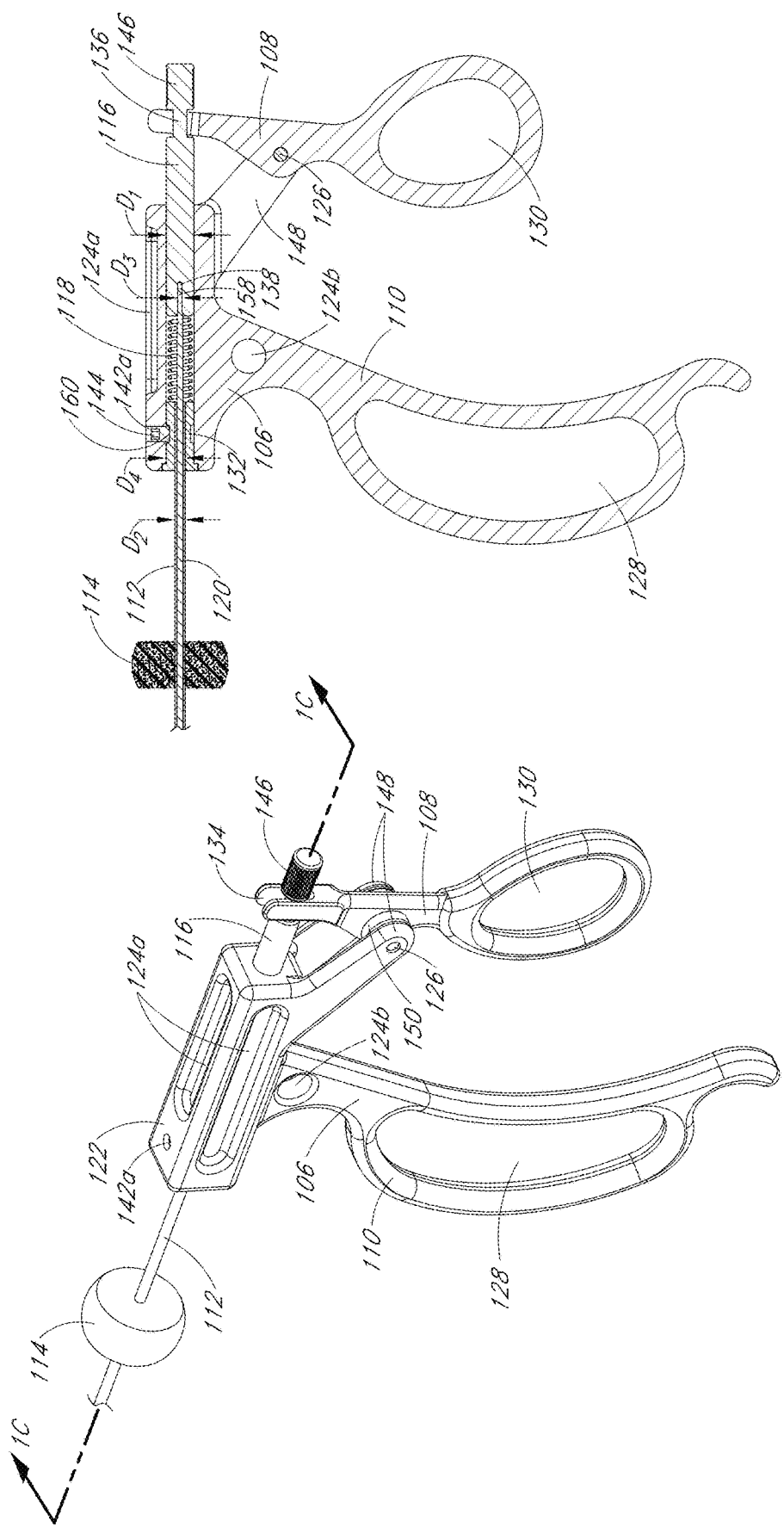

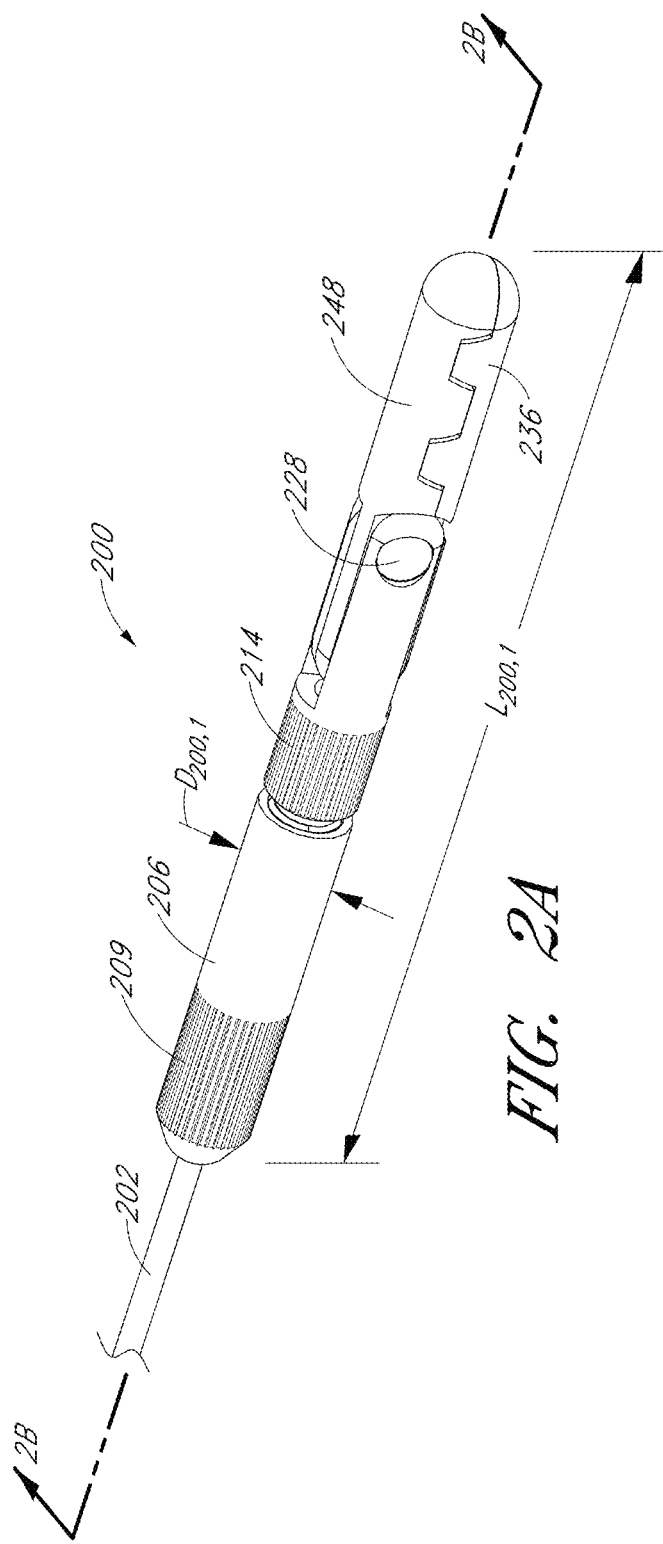
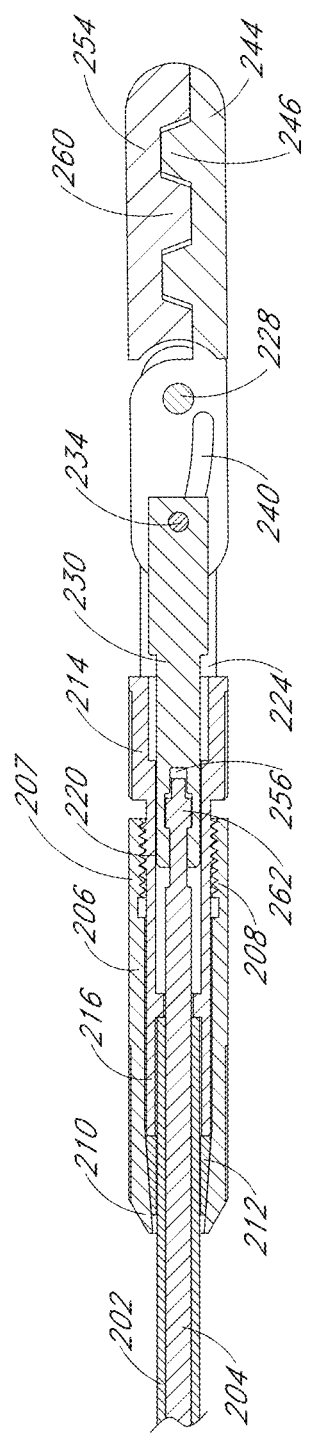
FIG. 2A
FIG. 2B

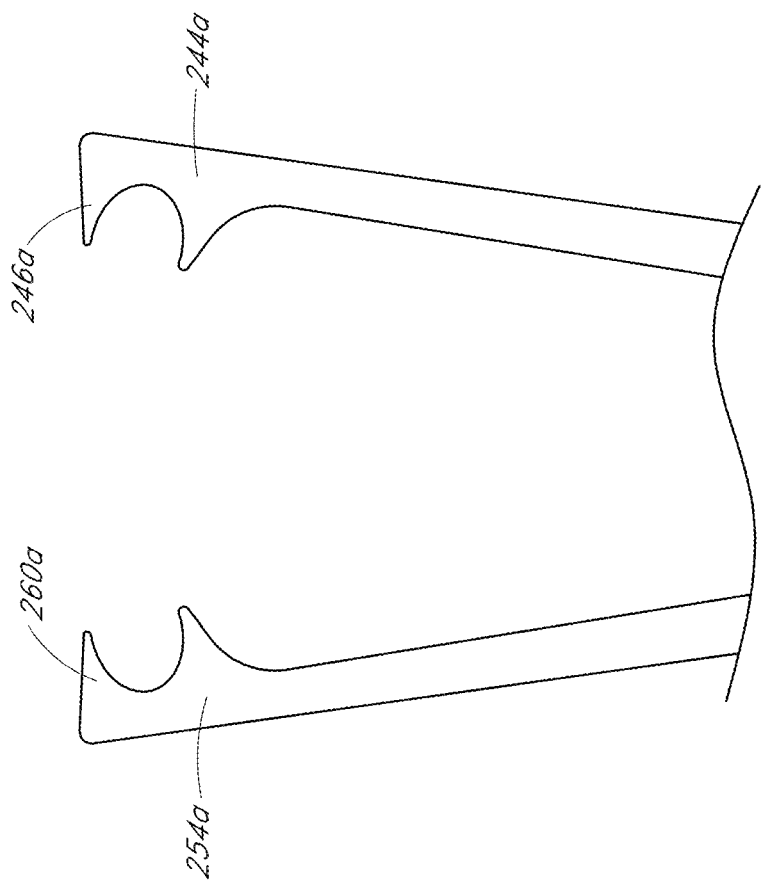
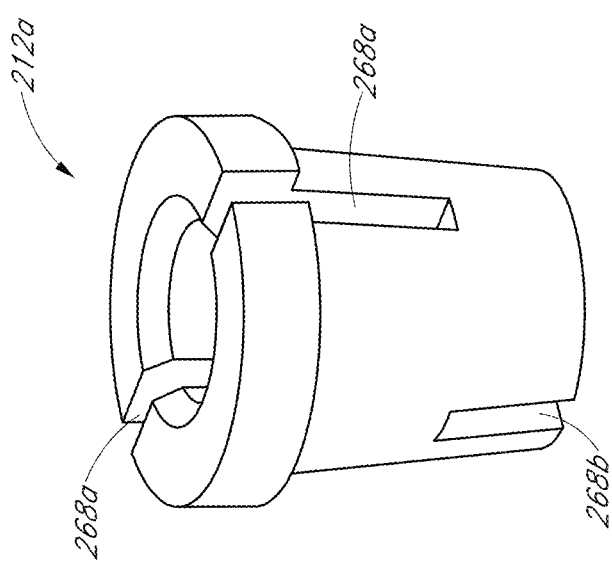
FIG. 2G
FIG. 2F

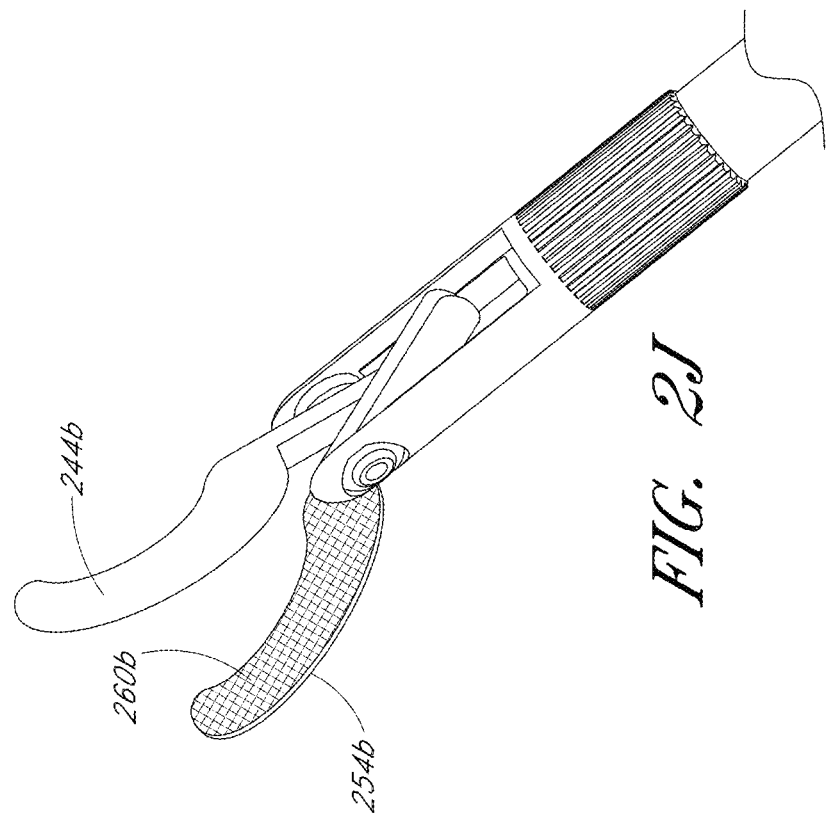
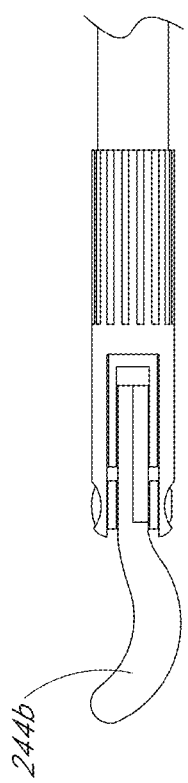
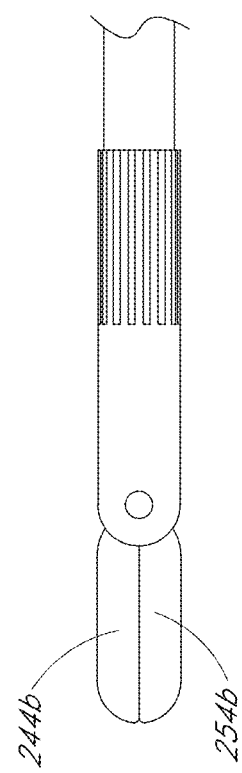

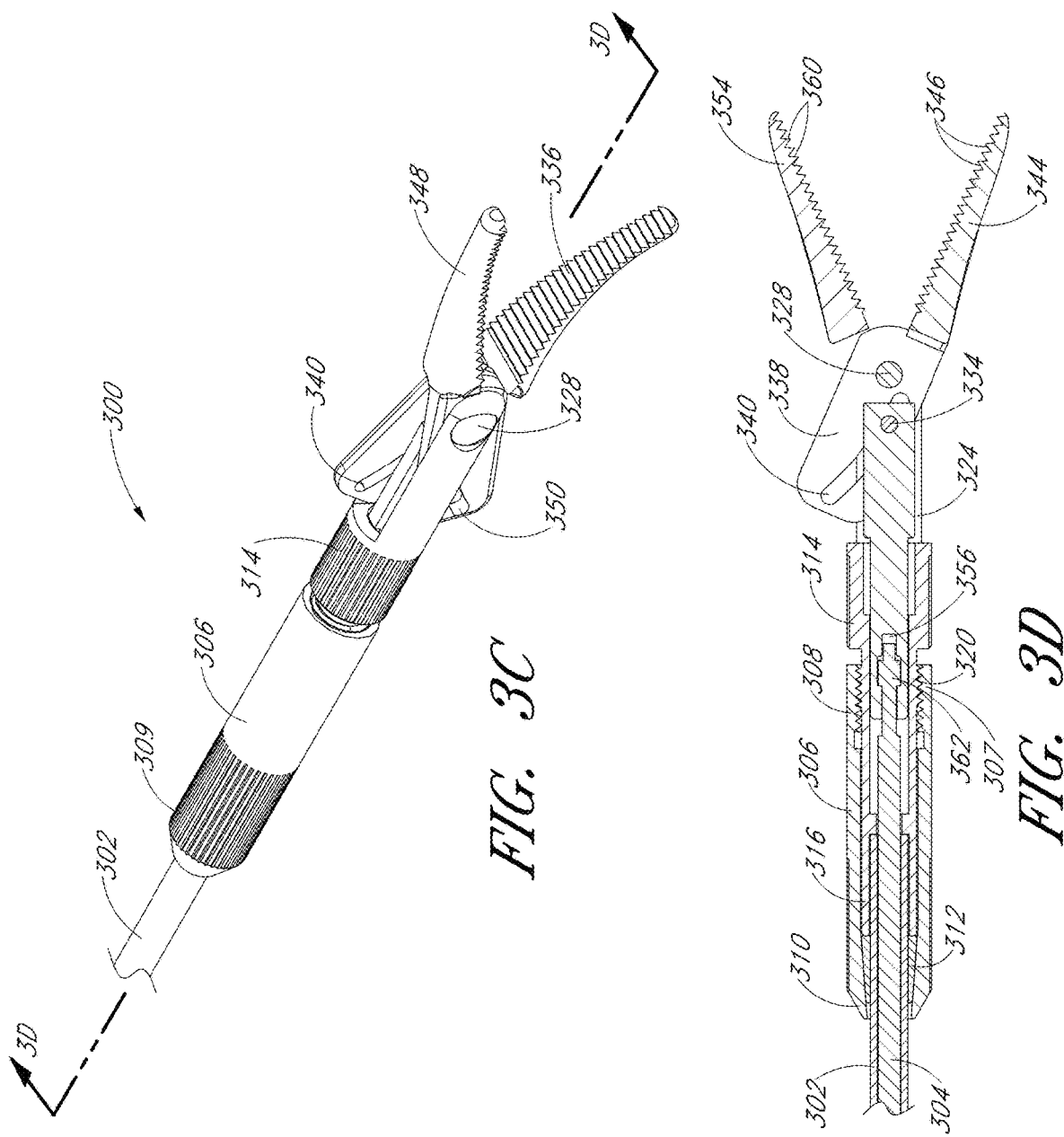

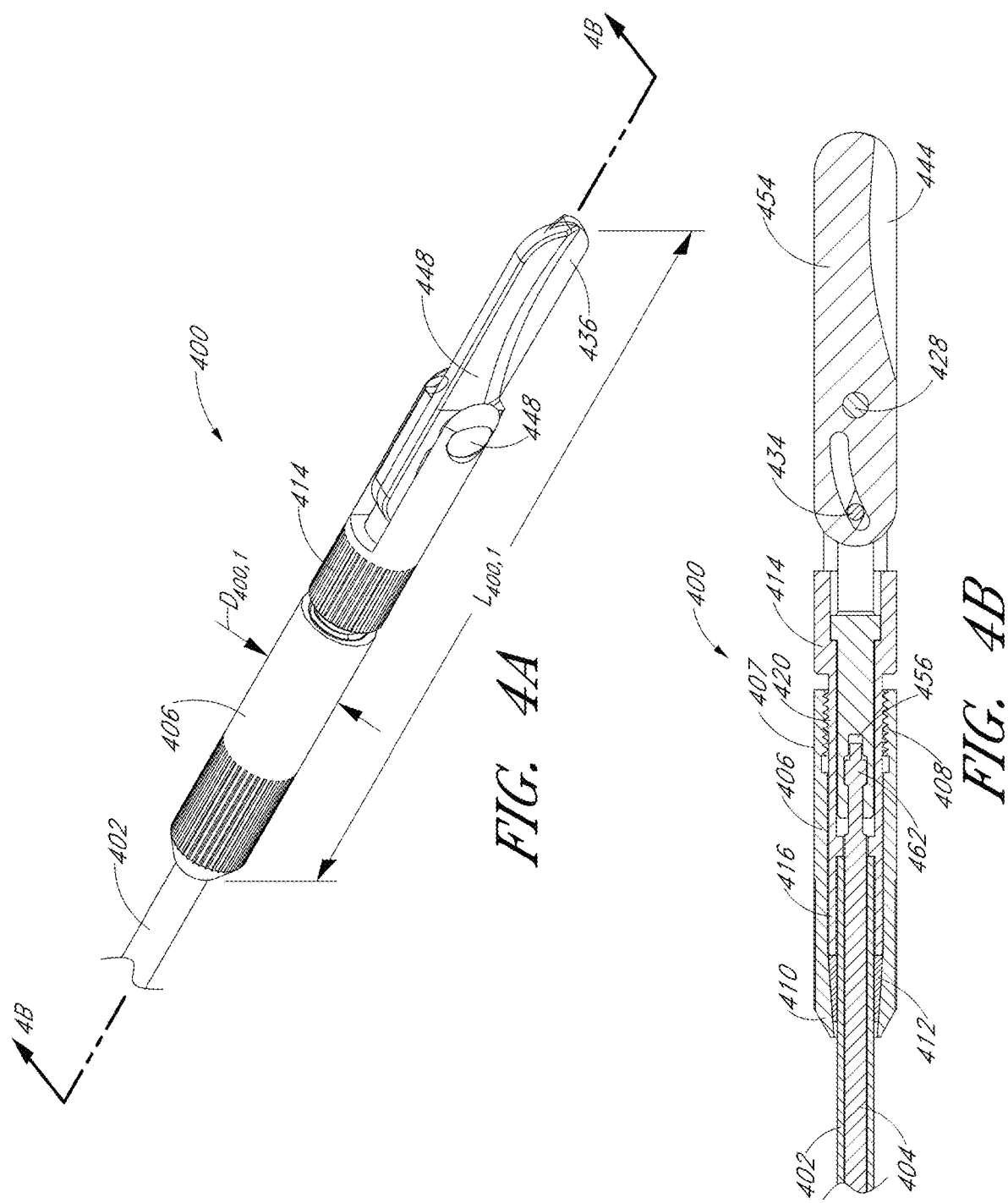

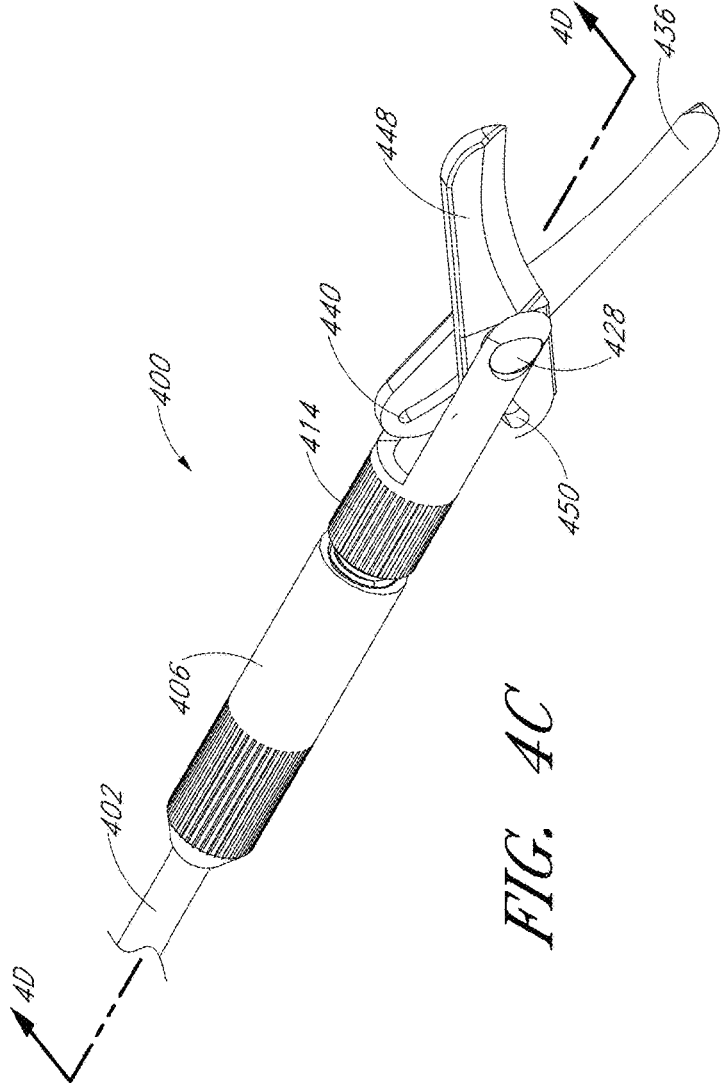
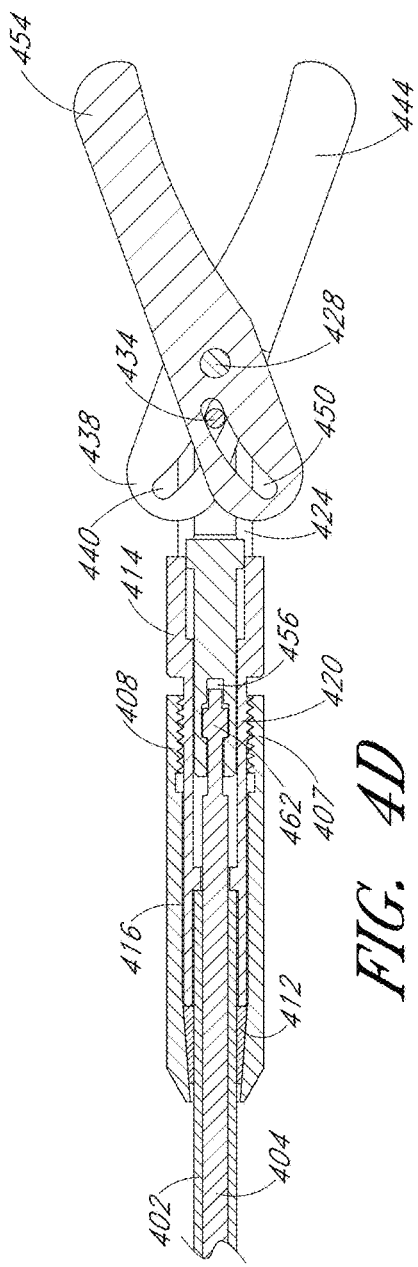
FIG. 4C
FIG. 4D

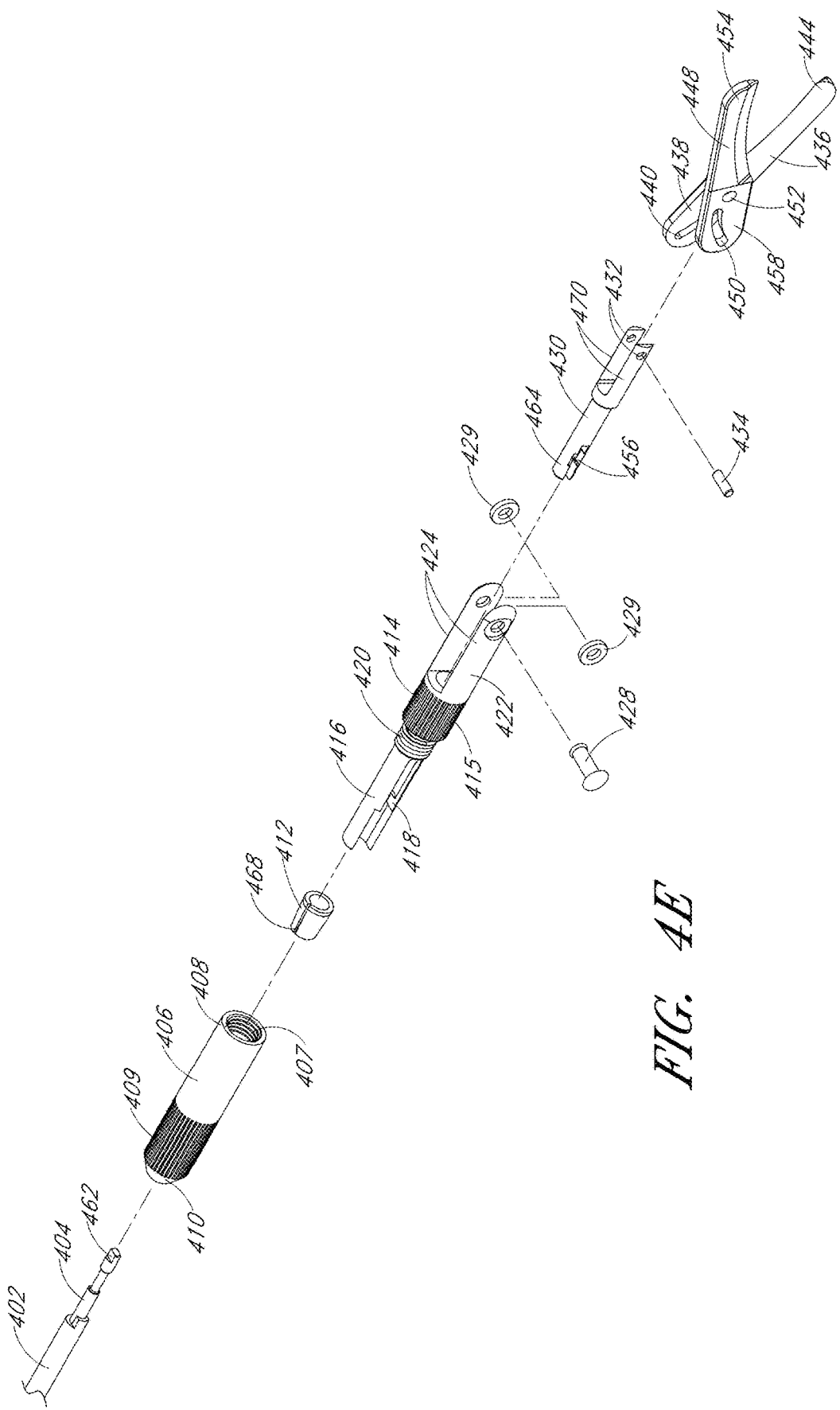

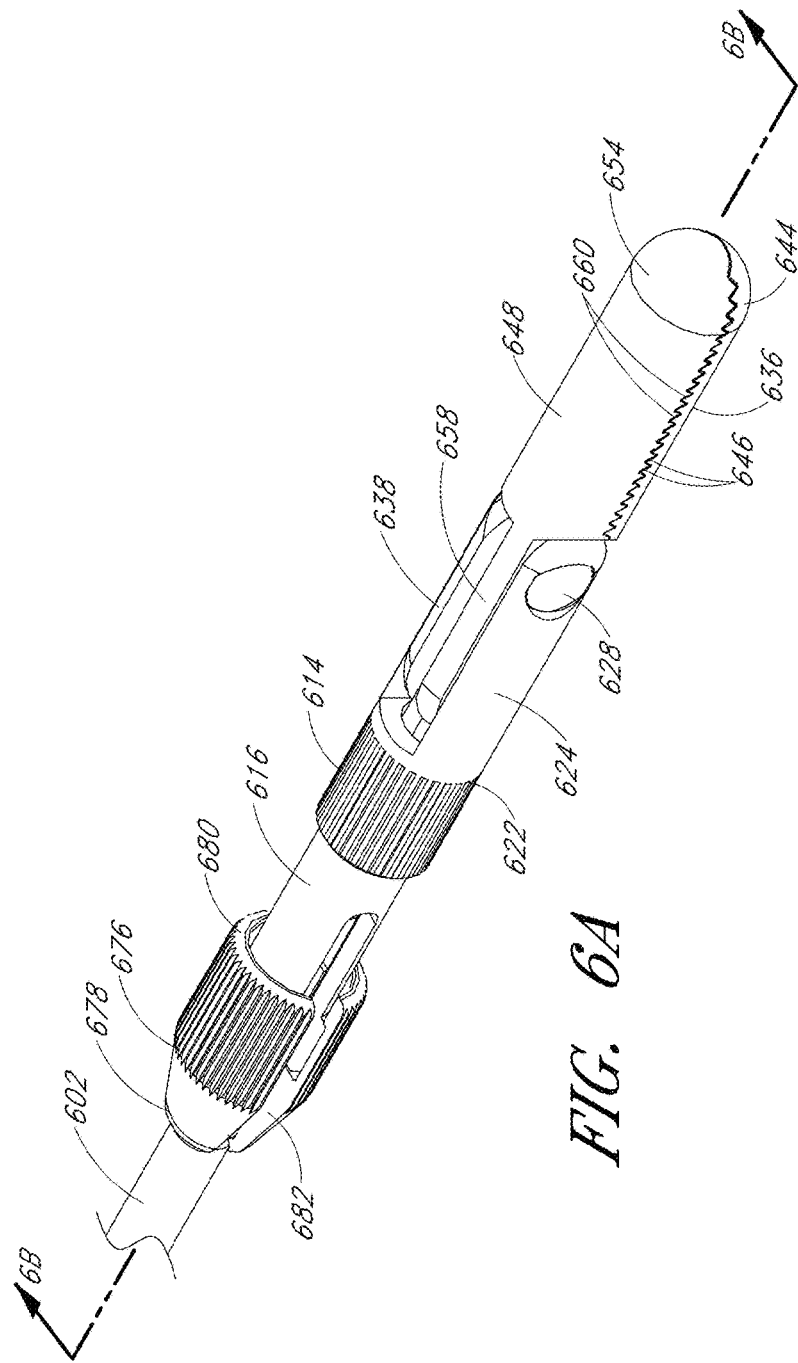
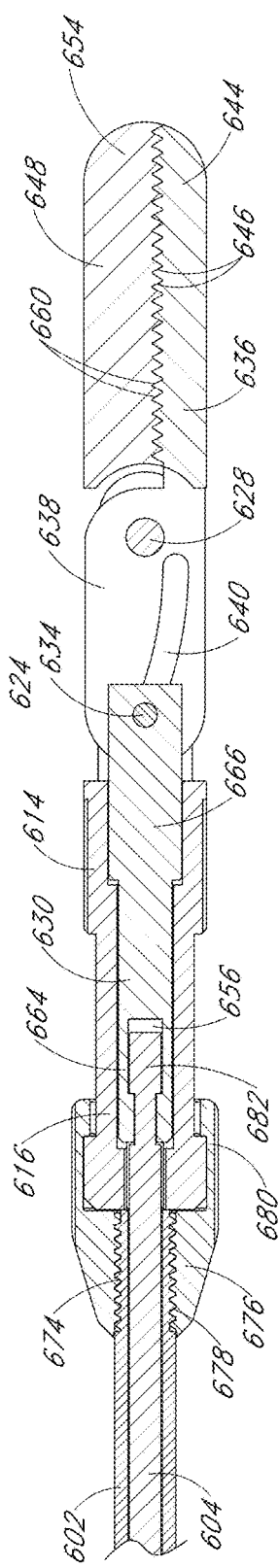
FIG. 6A
FIG. 6B

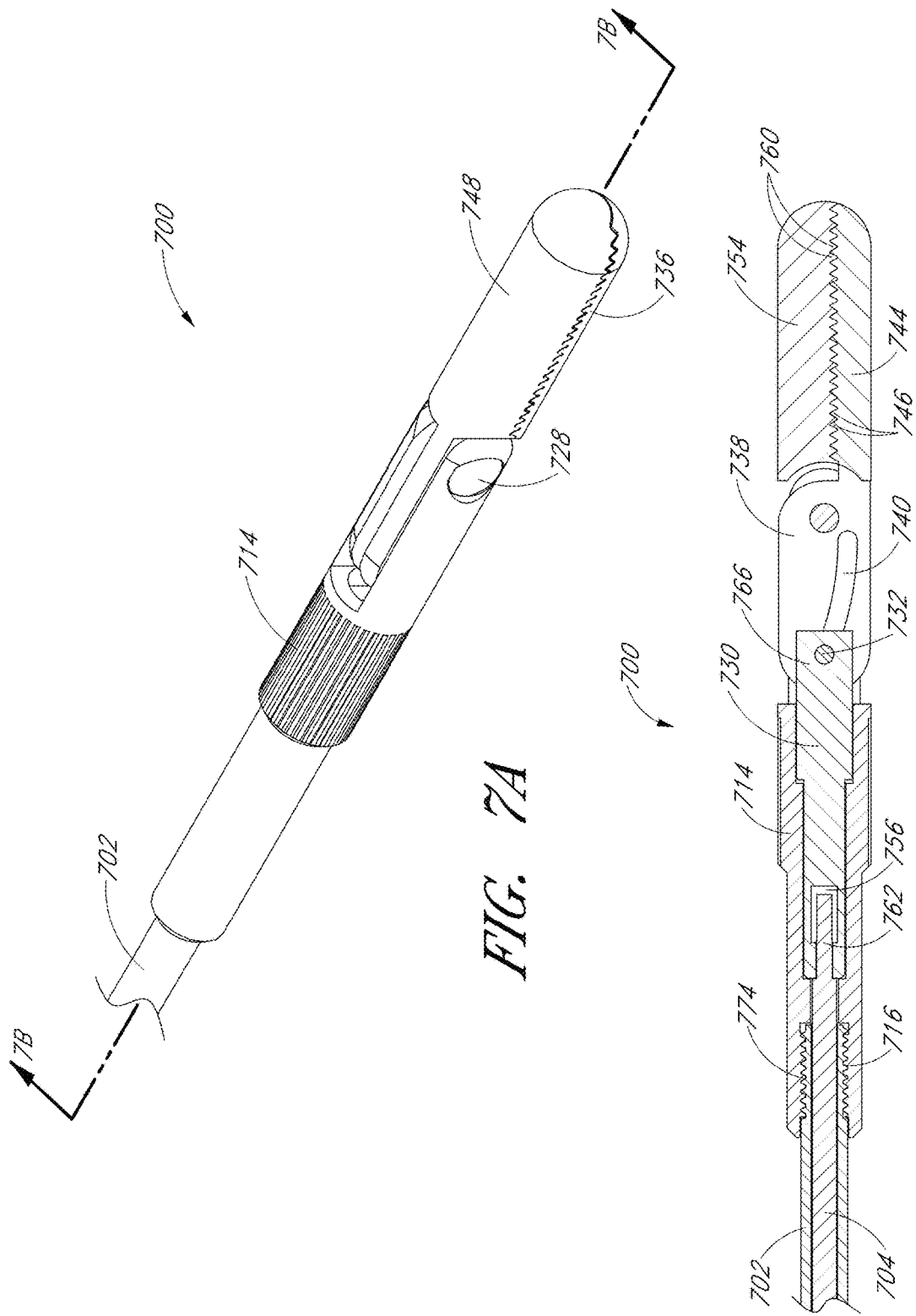

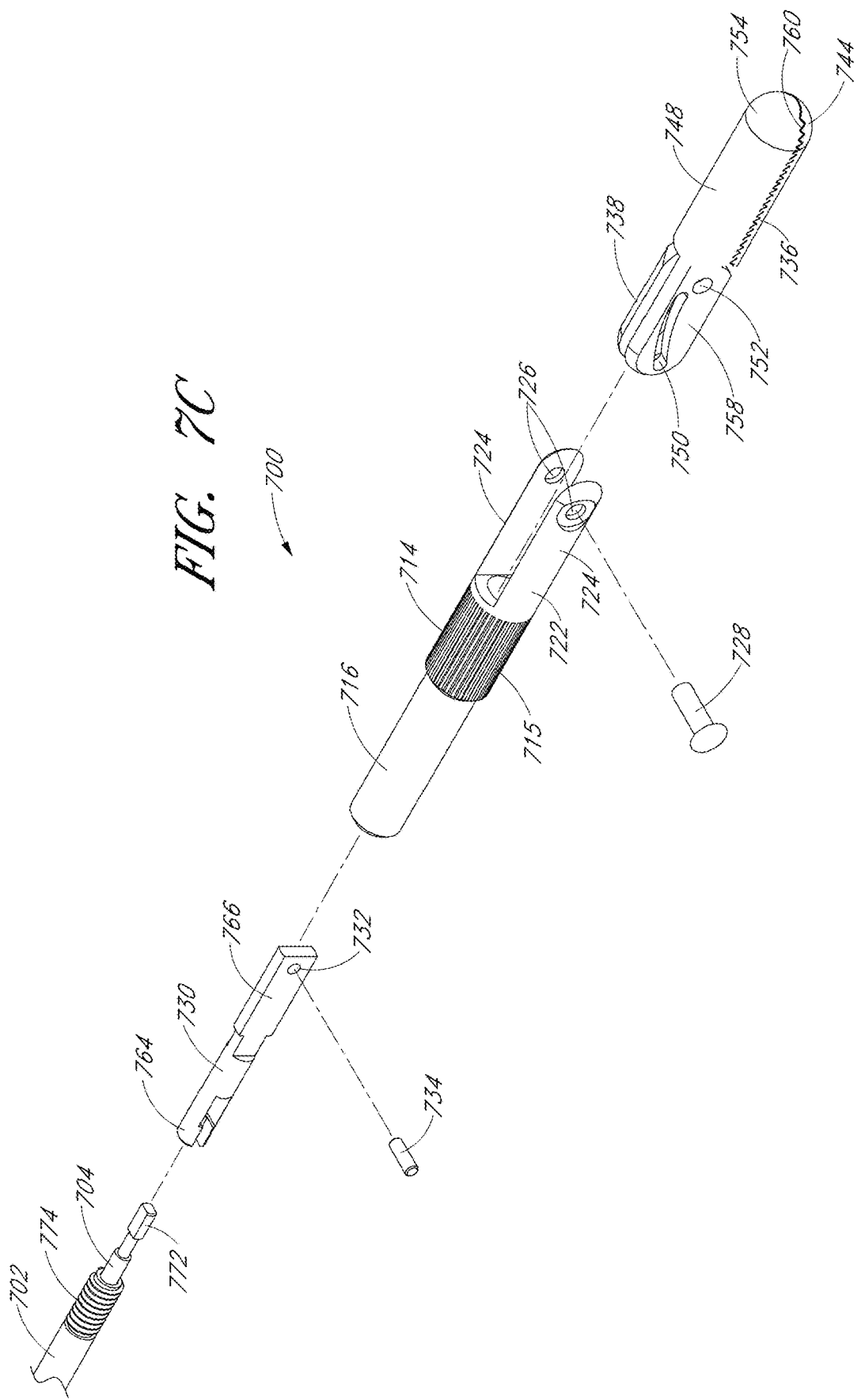

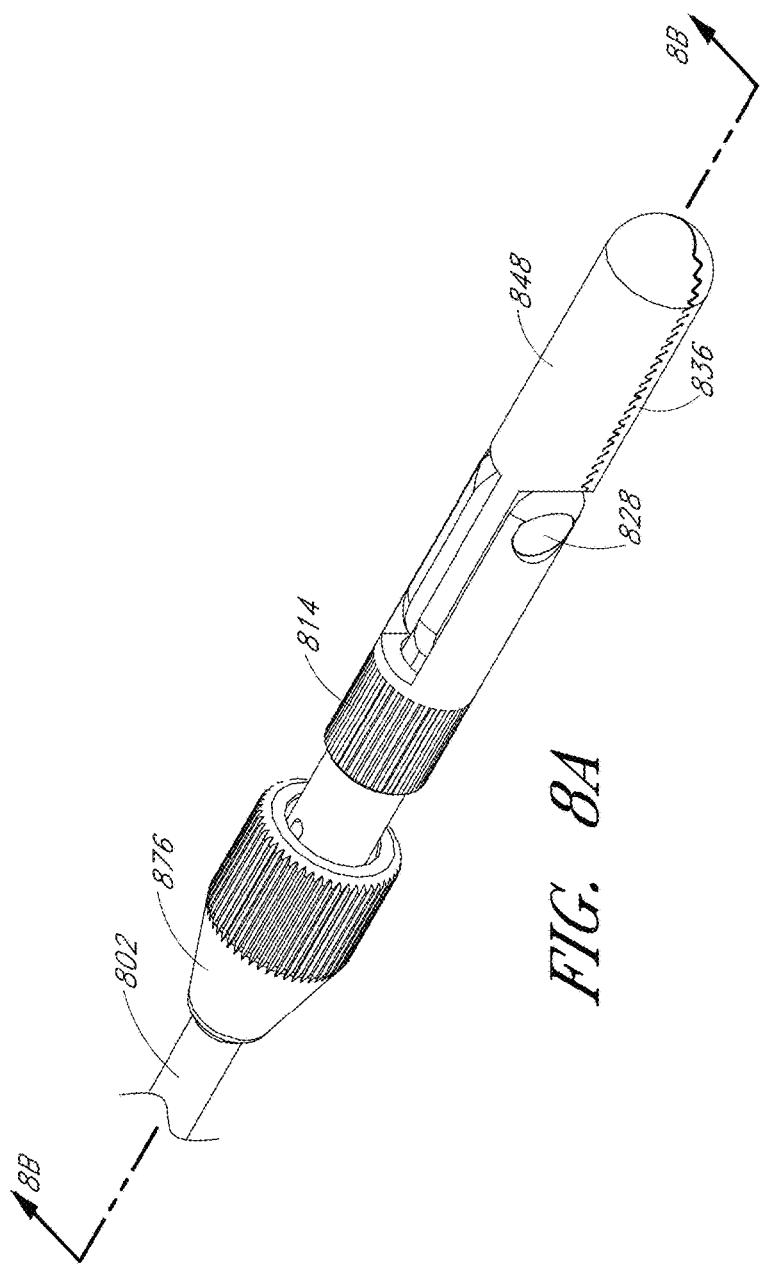
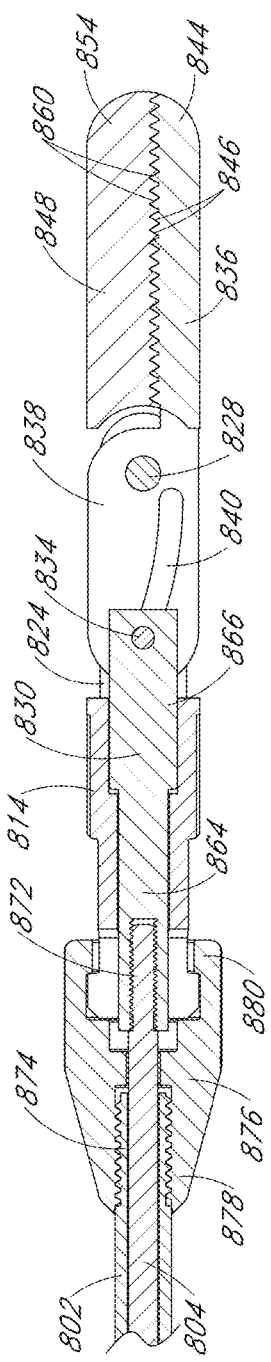
FIG. 8A
FIG. 8B

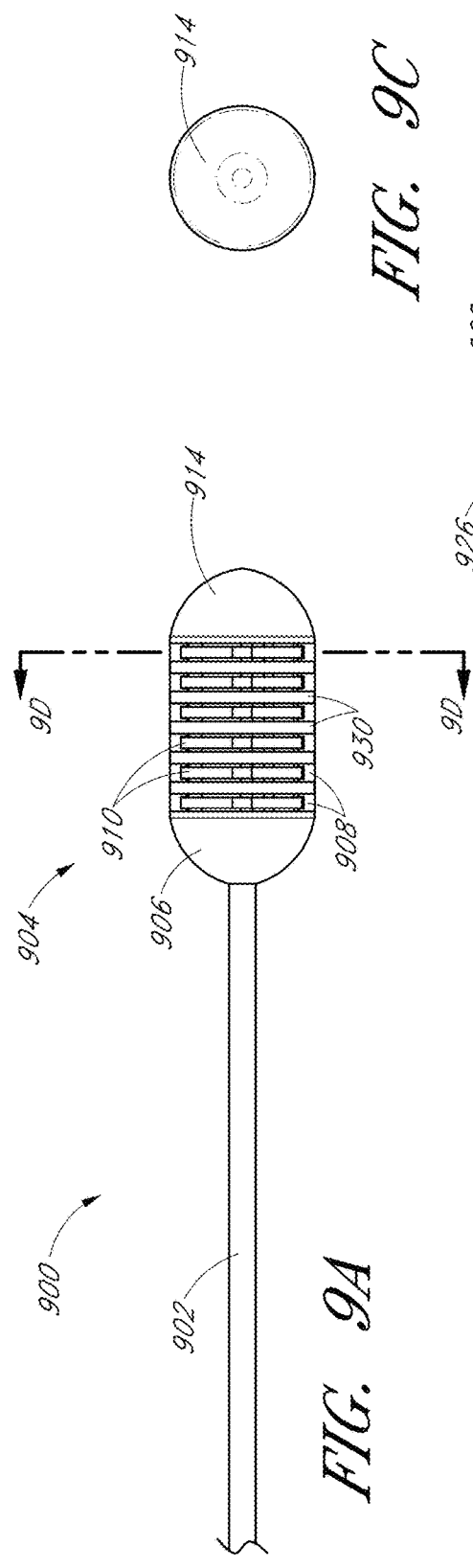
FIG. 9A
FIG. 9C
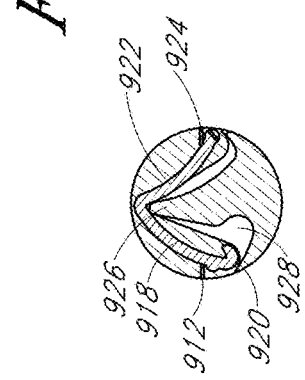
FIG. 9D
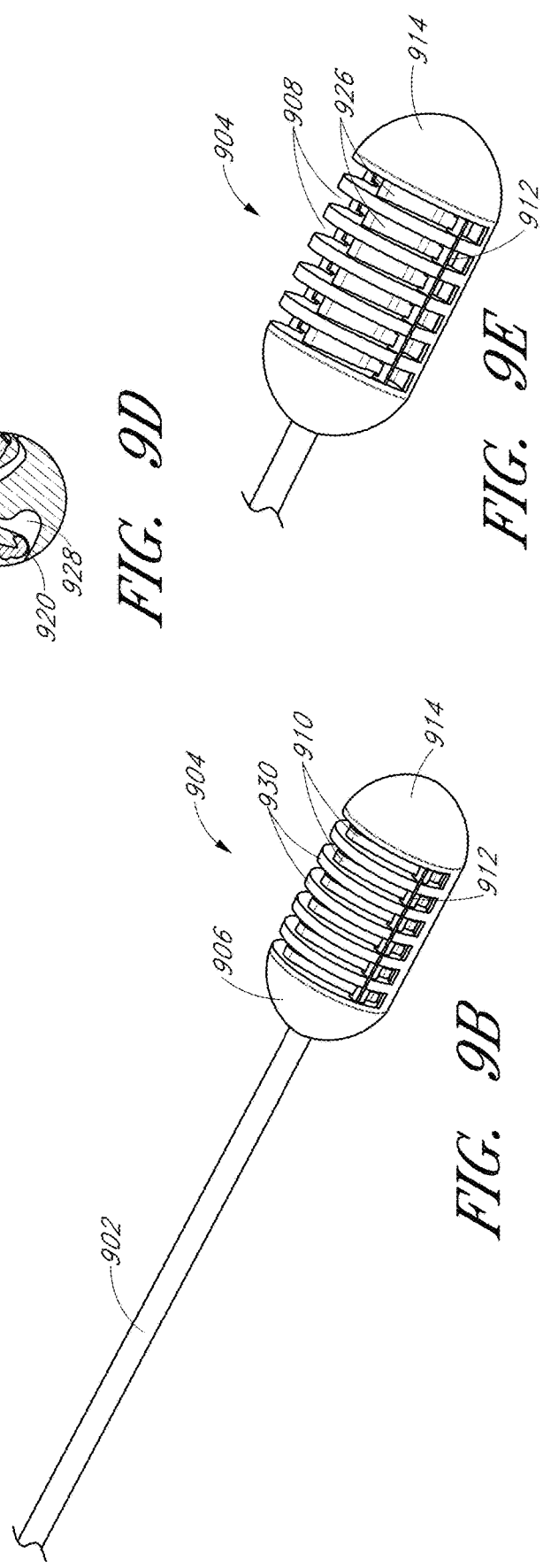
FIG. 9B
FIG. 9E

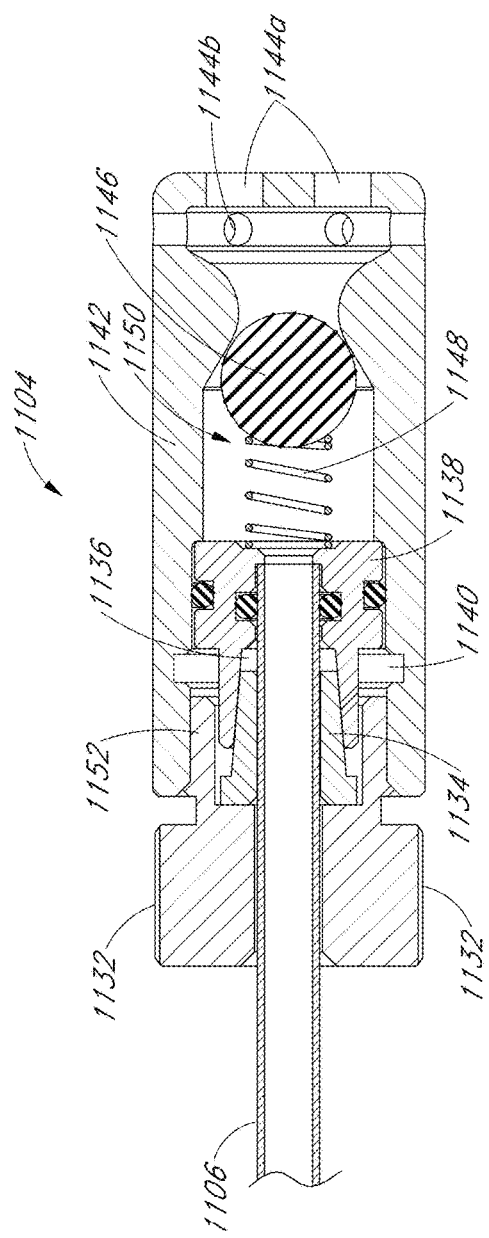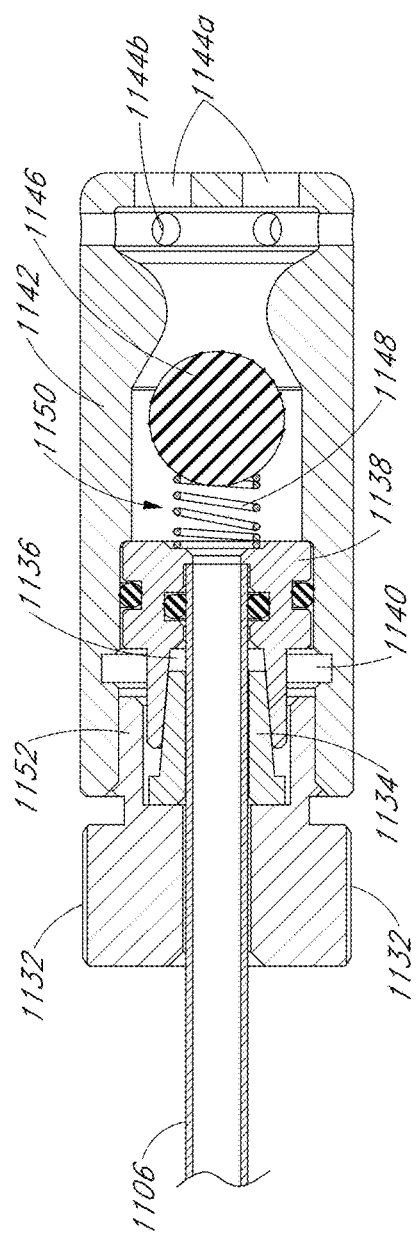
FIG. 11C
FIG. 11D

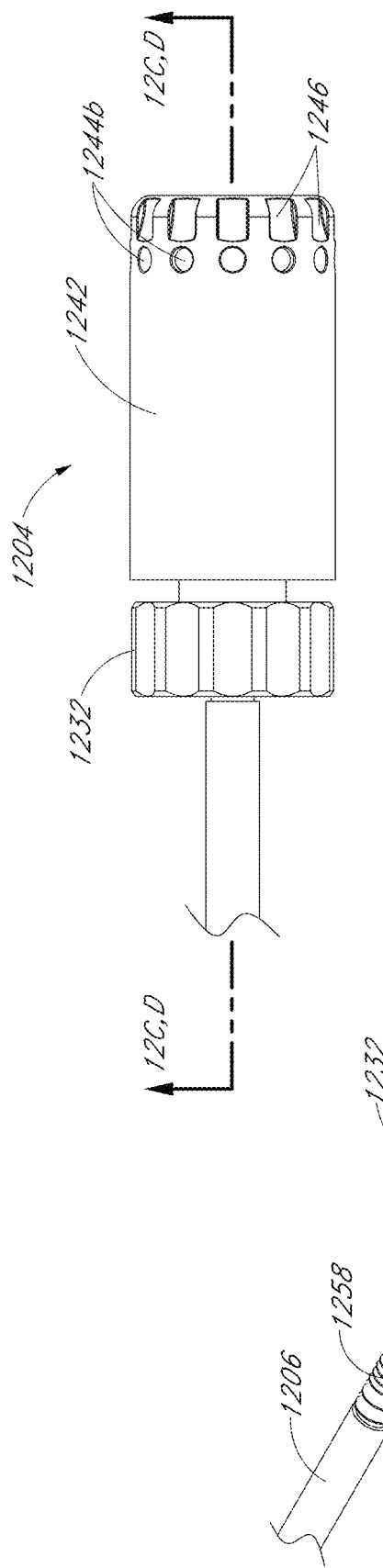
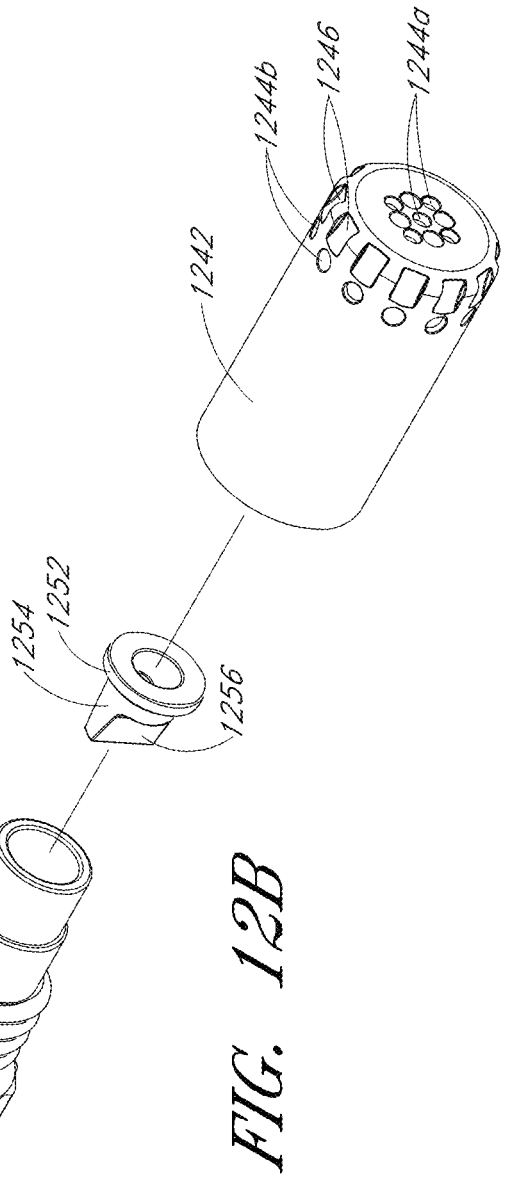
FIG. 12A
FIG. 12B

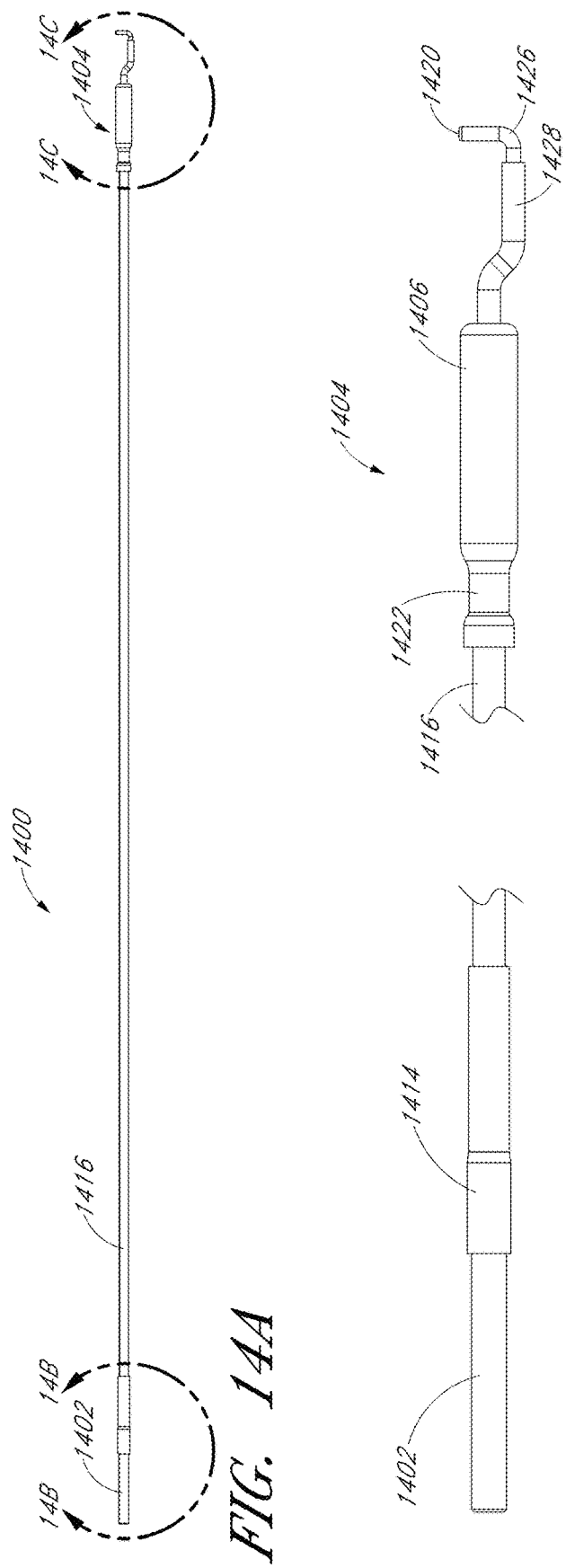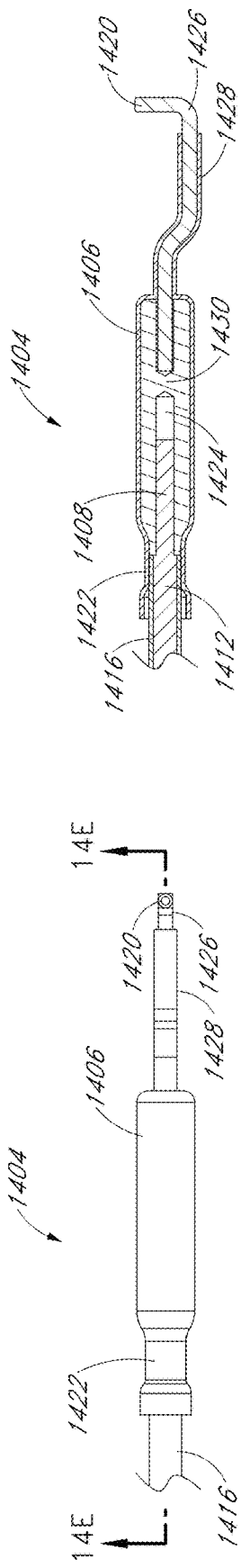

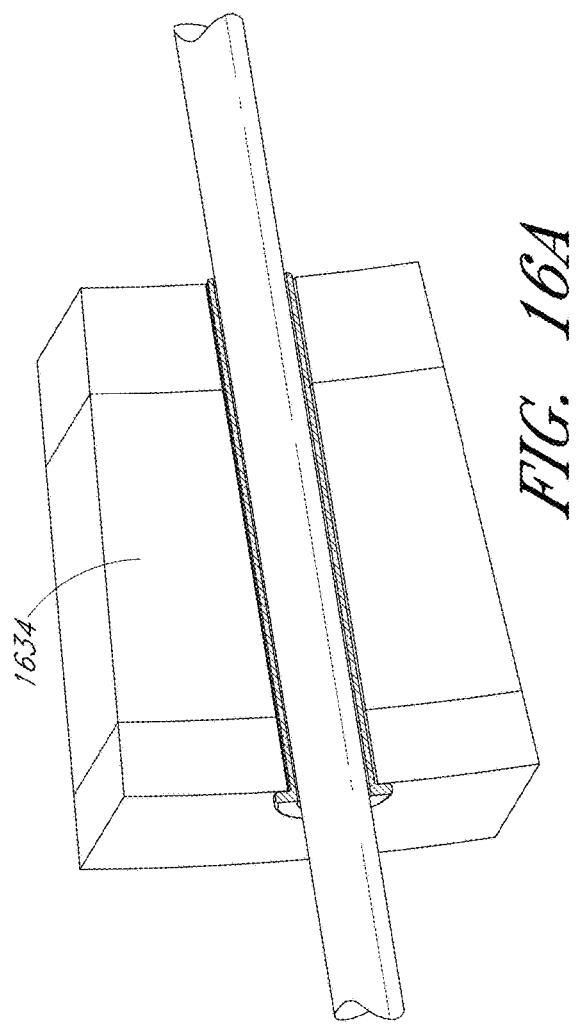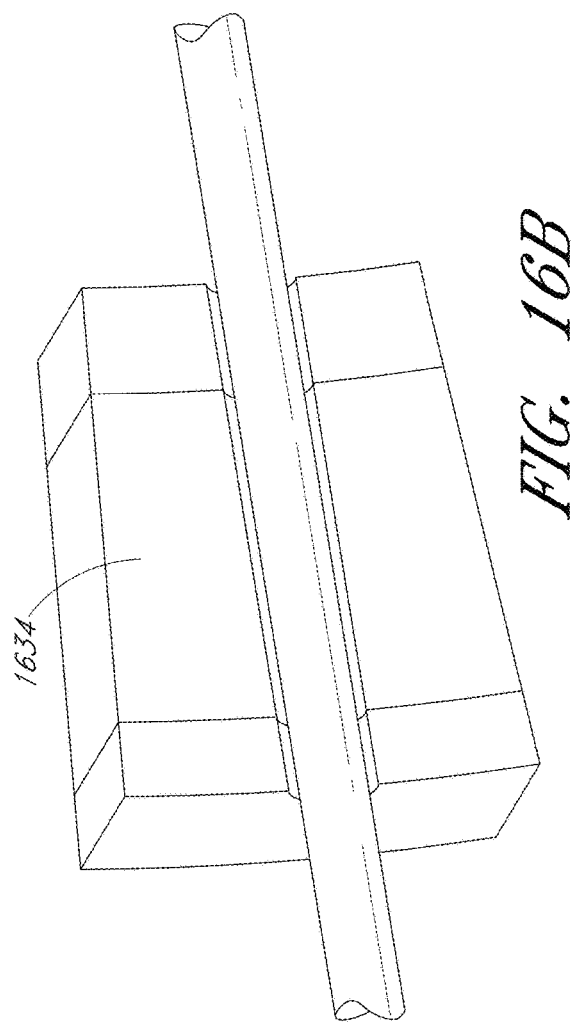

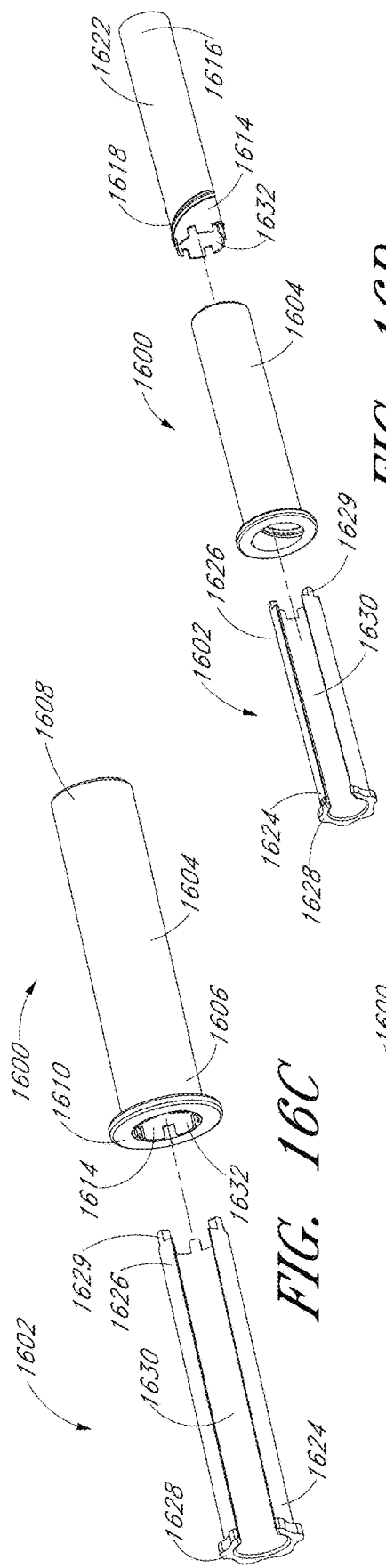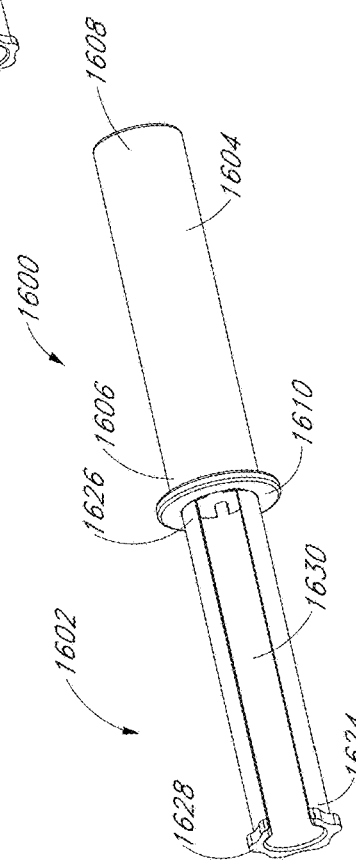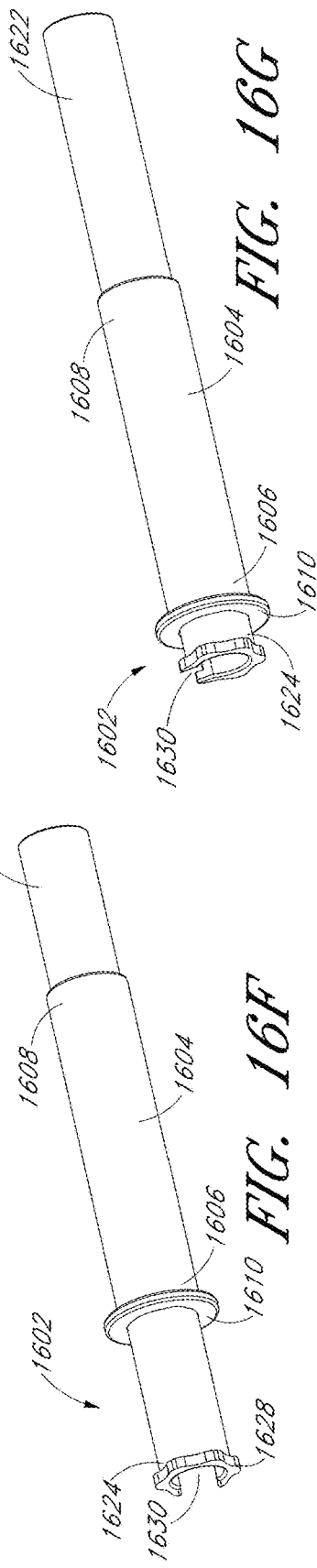

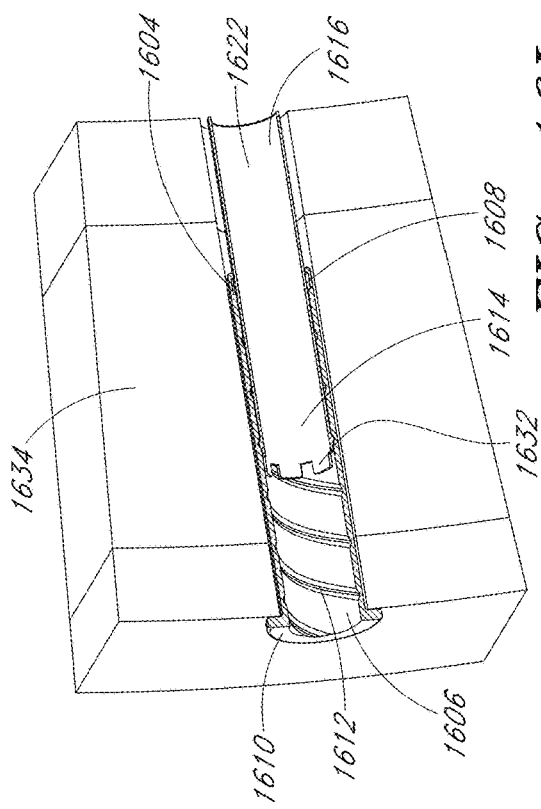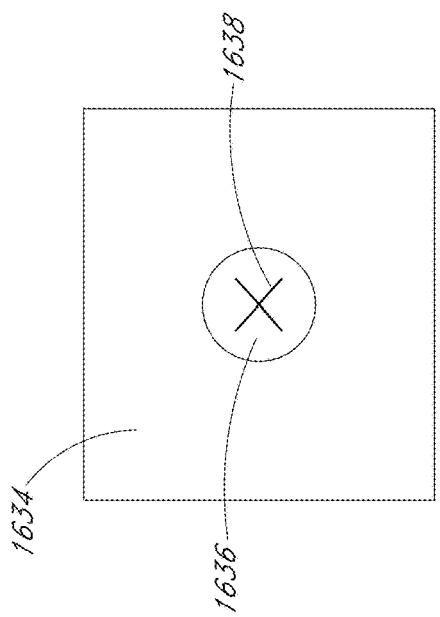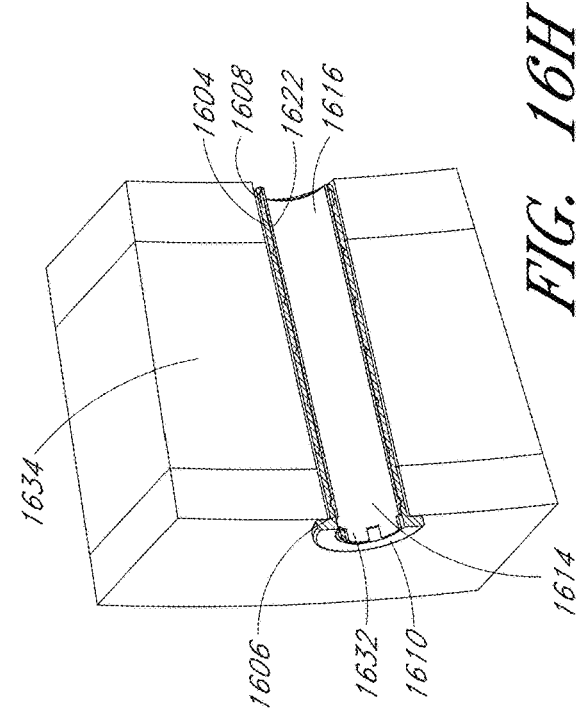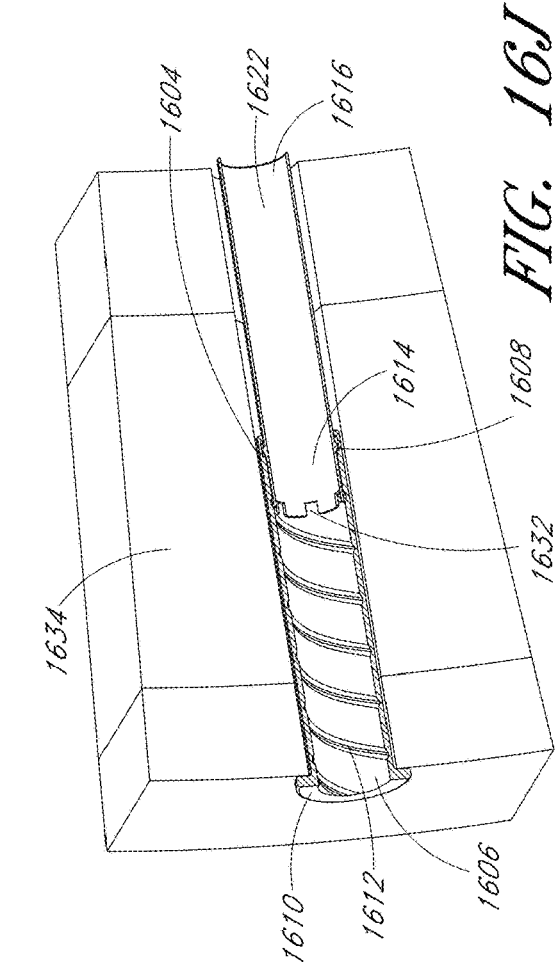
FIG. 16I
FIG. 16K
FIG. 16H
FIG. 16J

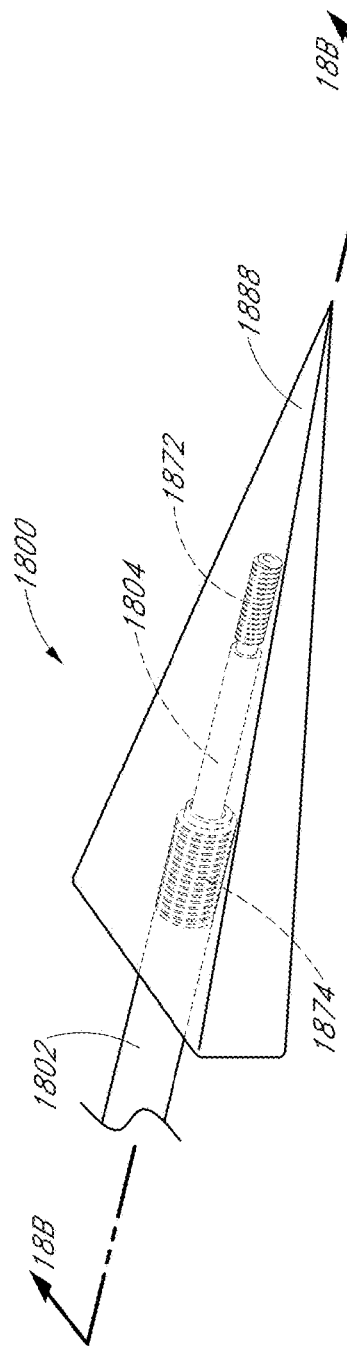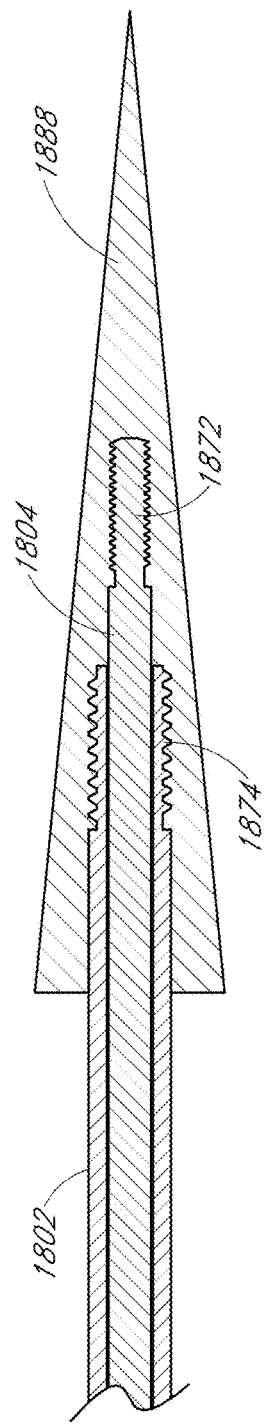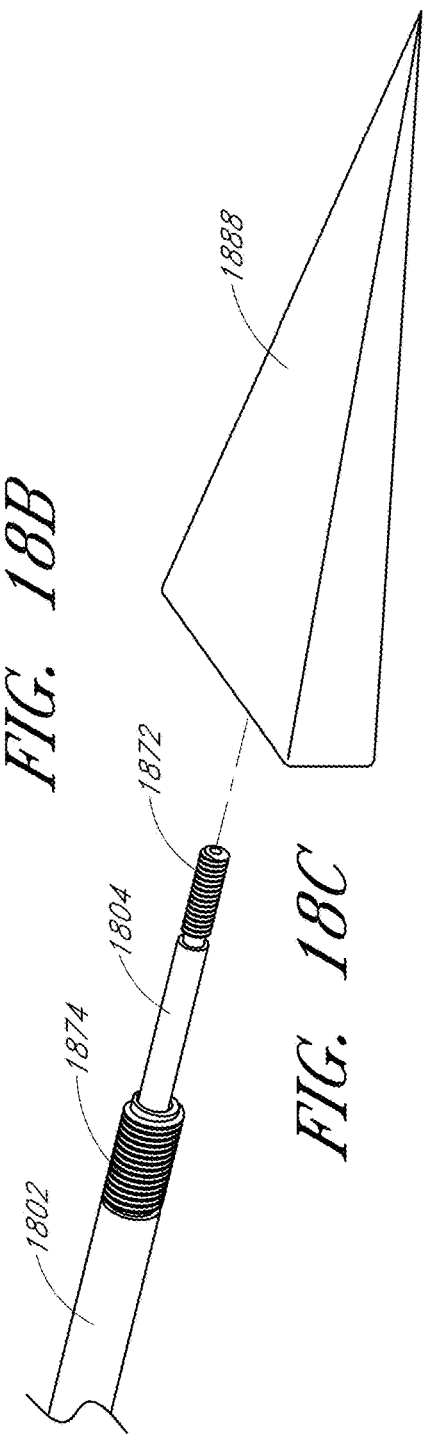

MINIMALLY INVASIVE SURGICAL DEVICES AND METHODS

CROSS-REFERENCE TO RELATED APPLICATIONS

This present application is a continuation of U.S. patent application Ser. No. 16/057,244, filed Aug. 7, 2018, titled "MINIMALLY INVASIVE SURGICAL DEVICES AND METHODS," now U.S. Pat. No. 10,842,474, issued Nov. 24, 2020, which is a continuation of U.S. patent application Ser. No. 14/639,551, filed Mar. 5, 2015, titled "MINIMALLY INVASIVE SURGICAL DEVICES AND METHODS," now U.S. Pat. No. 10,299,771, issued May 28, 2019, which is a continuation of U.S. patent application Ser. No. 14/250,244, filed Apr. 10, 2014, titled "MINIMALLY INVASIVE SURGICAL DEVICES AND METHODS," now U.S. Pat. No. 8,992,566, issued Mar. 31, 2015, which claims priority and benefit to U.S. Provisional Application No. 61/811,092, filed Apr. 11, 2013, titled "MINIMALLY INVASIVE SURGICAL DEVICES AND METHODS," all of which is hereby incorporated by reference herein in their entirety.

BACKGROUND

Field

The present disclosure relates to minimally invasive surgical devices and methods.

Description of the Related Art

Abdominal surgery is used to treat various diseases and conditions. The surgical methods can include creating one or more incisions that can accommodate different tools. Certain known techniques for performing abdominal surgery suffer from various drawbacks.

SUMMARY

Traditional laparoscopic surgery can require multiple incisions for each tool used during the procedure. Each incision can have a length between about 1 to 2 cm. Although these incisions are smaller than traditional open surgery incisions, laparoscopic surgery still leaves behind multiple scars. Accordingly, there is still a need for surgical tools that leave behind no visible scars and/or reduce the total number of incisions necessary to perform a procedure.

Certain aspects of the present disclosure are directed toward a surgical tool that leaves behind no visible scars. The surgical tool can include a handle portion having a central shaft and a plurality of stabilizing shafts surrounding the central shaft. The scarless surgical tool can include a working end configured to be removably secured to the handle portion. The working end can include a securing member at a proximal portion of the working end, a housing portion configured to receive a distal portion of the central shaft, and a tool portion at a distal portion of the working end. The securing member can be configured to be secured to the plurality of stabilizing shafts. The central shaft can be configured to control movement of the tool portion when the working end is secured to the handle portion.

In the above-mentioned surgical tool, the securing member can surround the central shaft when the securing member is secured to the plurality of stabilizing shafts.

In any of the above-mentioned surgical tools, each of the plurality of stabilizing shafts can have a diameter of less than or equal to about 1.0 mm. In certain aspects, each of the plurality of stabilizing shafts can be hollow. In certain variants, each of the plurality of stabilizing shafts can be solid.

In any of the above-mentioned surgical tools, each of the stabilizing shafts can have a sharpened distal tip capable of forming an opening. In certain variants, each of the stabilizing shafts can have a spherical end to prevent injury.

In any of the above-mentioned surgical tools, a length of the central shaft can be longer than a length of each of the plurality of stabilizing shafts.

In any of the above-mentioned surgical tools, the securing member can include a locking mechanism that can fix the position of the plurality of stabilizing shafts relative to each other. In certain aspects, the locking mechanism can include a retaining ring that can form a friction fit with the securing member.

In any of the above-mentioned surgical tools, the working end can include a slide member positioned in the housing portion. The slide member can control movement of the tool portion. In certain aspects, the slide member can receive the distal portion of the central shaft, such that the slide member is positioned radially between the central shaft and the housing.

In any of the above-mentioned surgical tools, the tool portion can be graspers, and axial movement of the central shaft can move the graspers between an open configuration and a closed configuration.

Certain aspects of the present disclosure are directed toward a method of using a scarless surgical tool having any of the features described herein. For example, the scarless surgical tool can include a handle portion and a working end. The handle portion can include a plurality of stabilizing shafts surrounding a central shaft. The working end can include a securing member at a proximal portion of the working end, a housing portion extending from the securing member, and a tool portion at a distal portion of the working end. The method can include securing the proximal portion of the working end to the handle portion, and positioning a distal portion of the central shaft in the housing portion of the working end. The central shaft can be configured to control movement of the tool portion when the working end is secured to the handle portion. Securing the proximal portion of the working end to the handle portion can include securing the securing member to the plurality of stabilizing shafts.

In the above-mentioned method, securing the securing member to the plurality of stabilizing shafts can include locking the position of the plurality of stabilizing shafts relative to each other. In certain aspects, locking the position of the plurality of stabilizing shafts relative to each other can include forming a friction fit between a retaining ring and the securing member. The plurality of stabilizing shafts can be positioned radially between the retaining ring an outer periphery of the securing member.

In any of the above-mentioned methods, positioning the distal portion of the central shaft in the housing portion can include positioning the central shaft in a slide member, such that the slide member is positioned radially between the central shaft and the housing. The slide member can control movement of the tool portion.

Certain aspects of this disclosure are directed toward a surgical tool having a handle portion including a shaft portion and a push rod slidably disposed within the shaft portion. The surgical tool can include a working end removably connected to a distal portion of the shaft portion.

In certain aspects, the working end can include a housing portion configured to receive a distal portion of the shaft portion. A slide member can be at least partially disposed within the housing portion. The slide member can include a receiving portion configured to receive a distal portion of the push rod. In some configurations, a nut can threadably engage the housing portion. A ferrule can be coaxially positioned between the nut and the shaft portion.

In certain aspects, the working end can include a housing portion configured to threadably engage a distal portion of the shaft portion. The working end can include a slide member at least partially disposed within the housing portion. The slide member can be configured to threadably engage a distal portion of the push rod.

In certain aspects, the working end can include a slide member at least partially disposed within a housing portion. The slide member can include a receiving portion configured to receive a distal portion of the push rod. In some configurations, a nut can secure the housing portion to the shaft portion. The nut can threadably engage a distal portion of the shaft portion.

In certain aspects, the working end can include a housing portion configured to threadably engage a distal portion of the push rod. A slide member can be at least partially disposed within the housing portion. The slide member can include a receiving portion configured to receive a distal portion of the push rod.

Certain aspects of this disclosure are directed toward a clip holder having a cartridge body secured to a shaft portion. The cartridge body can include one or more openings configured to receive one or more surgical clips. Each opening can be sized to permit at least partial deflection of the one or more surgical clips.

Certain aspects of this disclosure are directed toward a suction tool having a suction end secured to a shaft portion. The suction end can include a suction tip. A one-way check valve can be positioned within the suction tip.

Certain aspects of this disclosure are directed toward a camera including a camera body having a proximal end and a distal end. At least two image sensors can be positioned at a distal end of the camera body. One or more lights can be positioned at the distal end of the body. The camera body can define at least one or more lumens configured to removably engage a control rod.

Certain aspects of this disclosure are directed toward an adjustable port. The adjustable port can include an outer member having a tubular body and an annular rim disposed at a first end of the outer member. The outer member can include a first threaded region. An inner member can be slidably disposed within the outer member. The inner member can include a second threaded region configured to threadably engage the first threaded region.

For purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. In addition, various features of different disclosed embodiments can be combined to form additional embodiments, which are part of this disclosure.

FIG. 1B illustrates an enlarged view of the handle portion illustrated in FIG. 1A.

FIG. 1C illustrates a cross section of the handle portion illustrated in FIG. 1B taken along lines 1C-1C.

FIG. 2A illustrates a perspective view of a grasper tool in a closed configuration.

FIG. 2B illustrates a cross-section of the grasper tool shown in FIG. 2A taken along line 2B-2B.

FIG. 2F illustrates a ferrule that can be used with the grasper tool shown in FIGS. 2A-2D.

FIG. 2G illustrates an alternate jaw member shape for the grasper tool shown in FIGS. 2A-2D used to apply a locking clip.

FIGS. 2H-2J illustrate yet another alternate jaw member shape for the grasper tool shown in FIGS. 2A-2D for a needle driver.

FIG. 3C illustrates a perspective view of the dissector tool shown in FIG. 3A in an opened configuration.

FIG. 3D illustrates a cross-section of the dissector tool shown in FIG. 3C taken along line 3D-3D.

FIG. 4A illustrates a perspective view of a scissor tool in a closed configuration.

FIG. 4B illustrates a cross-section of the scissor tool shown in FIG. 4A taken along line 4B-4B.

FIG. 4C illustrates a perspective view of the scissor tool shown in FIG. 4A in an opened configuration.

FIG. 4D illustrates a cross-section of the scissor tool shown in FIG. 4C taken along line 4D-4D.

FIG. 4E illustrates an exploded view of the scissor tool shown in FIG. 4A.

FIG. 6A illustrates a perspective view of yet another grasper tool.

FIG. 6B illustrates a cross-section of the grasper tool shown in FIG. 6A taken along line 6B-6B.

FIG. 7A illustrates a perspective view of another embodiment of a grasper tool.

FIG. 7B illustrates a cross-section of the grasper tool shown in FIG. 7A taken along line 7B-7B.

FIG. 7C illustrates an exploded view of the grasper tool shown in FIG. 7A.

FIG. 8A illustrates a perspective view of yet another embodiment of a grasper tool.

FIG. 8B illustrates a cross-section of the grasper tool shown in FIG. 8A taken along line 8B-8B.

FIG. 9A illustrates a top view of a clip holder holding a plurality of clips.

FIG. 9B illustrates a perspective view of a clip holder holding a plurality of clips.

FIG. 9C illustrates an elevational view of a distal end of the clip holder.

FIG. 9D illustrates a cross-section of the clip holder shown in FIG. 9A taken along line 9D-9D.

FIG. 9E illustrates a perspective view of the clip holder shown in FIG. 9B without any clips.

FIG. 11C illustrates a cross-section of the suction end shown in FIG. 11A taken along line 11C-11C in a closed configuration.

FIG. 11D illustrates a cross-section of the suction end shown in FIG. 11A taken along line 11D-11D in an opened configuration.

FIG. 12A illustrates a perspective view of another suction end.

FIG. 12B illustrates an exploded view of the suction end shown in FIG. 12A.

FIG. 14A illustrates an elevational view of an electrocautery tool.

FIG. 14B illustrates an enlarged view of a connection portion of the electrocautery tool shown in FIG. 14A.

FIG. 14C illustrates an enlarged view of the hook electrode assembly of the electrocautery tool shown in FIG. 14A.

FIG. 14D illustrates a top view of the hook electrode assembly shown in FIG. 14C.

FIG. 14E illustrates a cross-section of the hook electrode assembly shown in FIG. 14D taken along line 14E-14E.

FIG. 16A illustrates a cross-section of a surgical tool extending through a port traversing an abdominal wall.

FIG. 16B illustrates a cross-section of a surgical tool extending through an abdominal wall without the standard port.

FIG. 16C illustrates a perspective view of an adjustable port and an adjustment tool used to modify the length of the adjustable port.

FIG. 16D illustrates an exploded view of the adjustable port.

FIGS. 16E thru 16G illustrate the adjustment tool connected to the adjustable port at varying lengths of the adjustable port.

FIGS. 16H thru 16J illustrate cross-sections of the adjustable port shown in FIG. 16A at varying lengths and positioned across the abdominal wall.

FIG. 16K illustrates a faceplate capable of engaging the adjustable port shown in FIG. 16A.

FIG. 18A illustrates a perspective view of an insertion tip configured for use with the shaft portion shown in FIGS. 5A-5C.

FIG. 18B illustrates a cross-section of the insertion tip shown in FIG. 18A taken along line 18B-18B.

FIG. 18C illustrates an exploded view of the insertion tip shown in FIG. 18A.

DETAILED DESCRIPTION

Figure 1A:
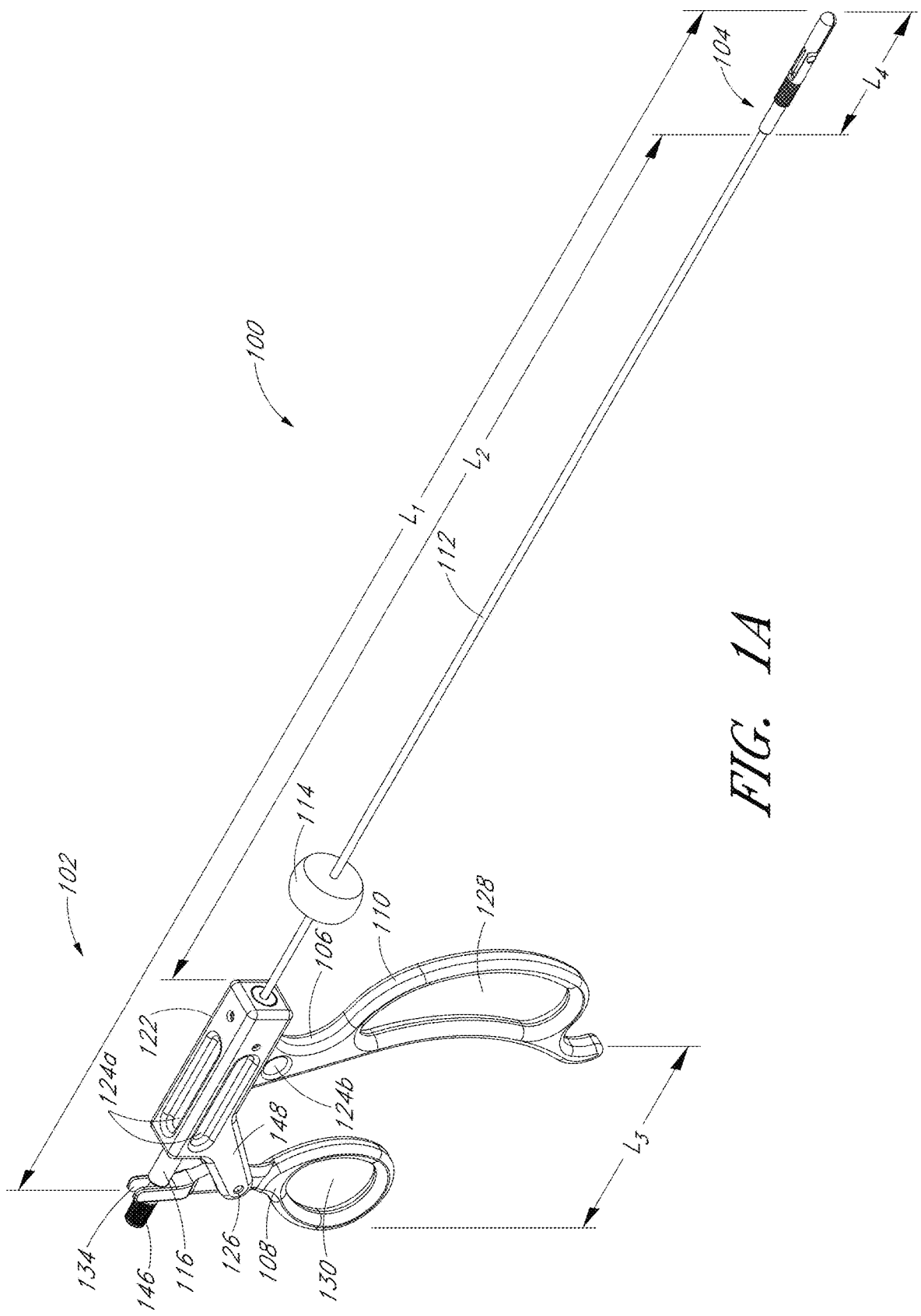
FIG. 1A illustrates a perspective view of a surgical tool.

During open surgery, surgeons make large incisions that allow them to insert both hands into the abdominal cavity.

This traditional open surgery requires large incisions that can accommodate retractors and tools inserted into the abdominal cavity. However, these large incisions can slow down the recovery process and leave behind large scars.

During the 1980's and 1990's, a new form of surgery was applied to many disease processes called laparoscopic surgery. In this form of surgery, several incisions are made which allows placement of multiple ports. An endoscopic camera and instruments are inserted through these ports to perform the functions previously performed using open instruments.

In some instances, laparoscopic surgery can require four to five incisions, each incision having a length of about 1 to 2 cm. Although these incisions are smaller than traditional open surgery incisions, laparoscopic surgery still leaves behind multiple scars each having a length of about 1 to 2 cm.

More recently, a new form of surgery was developed, which is known as LESS (laparoendoscopic single-site surgery). In this form of surgery, a single incision is created in the crease of the umbilicus. The LESS procedure incision can be about 2.5 to 3 cm, which can increase recovery time and increase the likelihood of a hernia.

The LESS procedure can be more difficult to perform than traditional open surgery or laparoscopic surgery because of a lack of triangulation. Triangulation is a method of positioning a camera and tools in a triangular fashion to facilitate instrument manipulation and adequate visualization. For example, during a laparoscopic procedure, the camera can be introduced through a central port and positioned to adequately visualize the target anatomy, while the tools can be introduced through lateral ports on either side of the central port to optimize access to the target anatomy and prevent the tools from colliding. Triangulation can facilitate natural right and left hand motion.

During the LESS procedure, all of the surgical tools are inserted through a single incision. As a result, the surgeon's hands and/or tools can collide when the surgeon attempts to operate the instruments. The absence of triangulation can also disrupt the surgeon's natural movement, which can increase the risk of complications and increase total surgery time. In addition, the use of a single incision can decrease the number and type of tools that can be used.

The present disclosure is directed toward a minimally invasive surgical method called scarless microport augmented restoration of triangulation surgery (SMART surgery), which is designed to eliminate the problems associated with the surgical methods described above. This minimally invasive surgical method can include forming one or more openings having a diameter of less than or equal to about 3.0 mm, preferably less than or equal to about 2.5 mm, or in some embodiments, less than or equal to about 1.5 mm or 1.0 mm. An opening having a diameter of less than or equal to about 3.0 mm will not leak insufflation gas and will not create any permanent scars in 50% of patients based upon research performed in our laboratory.

The one or more openings can be formed, for example, after insufflation, using a scalpel or a tool with an insertion tip. For example, the tool can include a handle, such as those handles described herein, and an insertion tip having a blade, such as the insertion tip shown in FIGS. 18A-18C. In some instances, when pressure is applied to the end of the tip, the blade can be released to form the one or more openings.

The SMART surgery method can include positioning the openings to facilitate triangulation, which, as described above, can help decrease complications, simplify the surgical procedure, and improve surgeon comfort. For example, the openings can include a central opening and one or more lateral openings on either side of the central opening. The central opening can have a diameter of less than or equal to about 4 cm, less than or equal to about 3 cm, less than or equal to about 1.5 cm, less than or equal to about 1 cm, or less than or equal to about 0.5 cm. The central opening can be formed through the umbilicus or at other locations, for example, at a location near the target anatomy, or in a site of low cosmetic and physiologic impact such as a Pfannenstiel incision, a suprapubic incision, in a skin fold or crease, or on the flank, or any other location the surgeon deems favorable. In some instances, the lateral openings can be substantially equidistant from the central opening and/or target anatomy, however in other instances the ports would be placed at different distances from the central opening to facilitate the particular task to be performed by the tool. As shown in FIGS. 1E and 1F, incisions can be formed at different locations depending on the target anatomy.

After the formation of the one or more openings, as shown in FIG. 16A, a port can be optionally introduced through one or more of the openings. The port can include a tubular structure configured to traverse a thickness of the abdominal wall, which can have a thickness of a few millimeters in very small neonatal applications and could be as thick as 20 cm or more in morbidly obese patients depending on the thickness of the muscle, fascia, and fat of the abdominal wall.

The tubular structures can include an internal diameter sized to receive a surgical tool having a shaft diameter ranging from 0.05 mm up to 3.0 mm. For example, the tubular structure can include an inner diameter of at least about 0.5 mm and/or less than or equal to about 3.0 mm. In some embodiments, the tubular structure can include an inner diameter between about 0.05 mm and about 0.5 mm, between about 0.51 mm and about 1.0 mm, between about 1.1 mm and about 1.5 mm, between about 1.51 mm and about 2.0 mm, between about 2.01 mm and about 2.5 mm, or between about 2.51 mm and about 3.0 mm. In some embodiments, the tubular structure can include an outer diameter of at least about 0.1 mm and less than or equal to about 3.5 mm. For instance, the tubular structure can include an outer diameter between 0.1 mm and 0.7 mm, between about 0.71 mm and about 1.2 mm, between about 1.21 mm and about 1.7 mm, between about 1.71 mm and about 2.2 mm, between about 2.21 mm and about 2.5 mm, between about 2.51 mm and about 2.7 mm, or between about 3.0 mm and about 3.5 mm In some instances, as shown in FIG. 16B, the tool can be introduced through the opening without the use of the port. This can be useful for maximizing the shaft diameter of the surgical tool and minimizing the skin opening size.

To achieve triangulation, the camera can be introduced through the central opening and a tool can be introduced through each one of the lateral openings. With the SMART surgery method, the surgeon can more easily perform the procedure using traditional laparoscopic techniques without leaving behind any scars.

During SMART surgery, it may be desirable to exchange the working end of the tool rather than use a completely separate tool. The ability to exchange the working end without removing the entire surgical tool can reduce complications associated with re-inserting tools into the patient. It can also save time and lower costs by allowing the surgeon to use one handle with multiple tips. In addition, the ability to exchange the working end can decrease the amount of inventory shelf space necessary to store the tools.

In some instances, the one or more openings can be sized to facilitate the exchange of working ends on a surgical tool.

For example, the method can include forming a first opening sized to receive the shaft portion of the surgical tool, but not the working end of a surgical tool. The method can include forming a second opening larger than the first opening and sized to receive the working end of the surgical tool. In some instances, the second opening can be formed in the umbilicus.

In some instances, the one or more openings can be positioned to facilitate the exchange of the working ends. For example, the method can include forming the first opening and the second opening. The first and the second openings can be positioned such that the distal end of the shaft portion can be introduced into the abdomen through the first opening and back out to the external environment through the second opening. Once the distal end of the shaft portion exits the abdomen, the working end can be connected to the distal end of the shaft portion. Thereafter, the working end can be introduced into the abdomen through the second opening. To exchange working ends, the working end can be introduced back out to the external environment allowing the physician to change the working end.

Due to the low cosmetic impact of the scarless ports, in some instances, the efficiency and safety of the procedure is enhanced by introducing multiple instruments through multiple scarless ports, including, but not limited to, any of the instruments discussed herein. For instance, the surgeon could introduce a Debakey-type grasper, a scissor, a clip applier, a clip cartridge, a right angle dissector, and/or a hook electrode all at the start of the procedure. All instruments that were not currently in use could be safely suspended on a rack external to the patient out of the way, but available inside the patient at a moment's notice should the surgeon require that instrument. Alternatively, the tools could be laid on the patient and affixed to the drape in a manner that ensured that the internal portions of the tool would not conflict with movements of the operating instruments in current use by the surgeon.

Multiple scarless ports allow the surgeon to dissect a vessel with a right angle dissector, apply clips, cut the vessel, and/or cauterize seamlessly without having to remove or change instruments. This method increases safety by ensuring that all tools required to control bleeding are immediately available to the surgeon. For example, if the surgeon, while dissecting a vessel, cuts a hole in a vessel and encounters bleeding, the surgeon would already have a grasper available inside the patient to hold the area of bleeding to control the bleeding, a right angle dissector immediately available inside the patient to dissect a plane around the vessel to clear it for clip application, a clip applier and clip immediately available to apply proximal and distal to the damaged area of the vessel, and/or scissors or cautery to sever the vessel between the clips without having to disassemble and change the tools.

The minimally invasive surgical procedures described above and/or use of any of the surgical tools described herein can be directly performed by a surgeon or robotically assisted. With robotic surgery, the surgeon can control the robotic arms by using computer controls or a telemanipulator. Robotic surgery can give the surgeon better control over the surgical tools and make access to certain anatomy easier. Any of the working ends described below (e.g., graspers, scissors, dissectors, needle drivers, insertion tips, suction ends, electrocautery tools, etc.) can be connected to the robotic arms using any of the connection features described below.

Handle Portion

FIGS. 1A-1D illustrate an exemplary surgical tool 100 that can be used with the SMART surgery method described above. The surgical tool 100 can include a handle portion 102 removably secured to a working end 104 (e.g., graspers, scissors, dissectors, needle driver, insertion tip, clip applier, suction tool, cautery tool, or otherwise) using any of the connection features described herein.

Any unintentional loosening of the working end 104 components can affect the functionality of the surgical tool 100. In addition, during the surgical procedure, if any of the working end 104 components fall into the patient, the surgeon will have to open, identify, localize, and remove the component, which may require complicated imaging and surgical methods. This may increase the invasiveness of the surgery up to and including traditional laparoscopic techniques and traditional open surgery. Accordingly, the connection features described herein are designed for easy assembly and stability.

During use, the handle portion 102 and/or the working end 104 can be reusable. For example, after a surgical procedure, both the handle portion 102 and the working end 104 can be sterilized using any medically acceptable method. Alternatively, both the handle portion 102 and the working end 104 can be disposed after the surgical procedure. In some instances, after the surgical procedure, the handle portion 102 can be sterilized and the working end 104 can be disposed.

The handle portion 102 and/or working end 104 can include any medical grade metal, such as stainless steel, or any medical grade polymer so long as the material has sufficient properties to carry out the functions described herein. If the surgical tool 100 is reusable, then the tool should be constructed from a medical grade metal or polymer that can be appropriately sterilized.

As shown in FIGS. 1A-1D, the handle portion 102 can include a first handle body 106 and a second handle body 108. The first and second handle bodies 106, 108 can include first and second finger openings 128, 130 sized to receive the surgeon's fingers. The first finger opening 128 can be elongated and sized to receive one or more of the surgeon's fingers during the procedure, and the second handle body 108 can include the thumb opening 130 sized to receive the surgeon's thumb.

The first handle body 106 can include a generally elongate portion 122 and a grip portion 110. The elongate portion 122 can be substantially coaxial with the shaft portion 112, and the grip portion 110 can extend downward from the generally elongate portion 122. The grip portion 110 can be integrally or separately formed with the generally elongate portion 122.

Figure 1D:
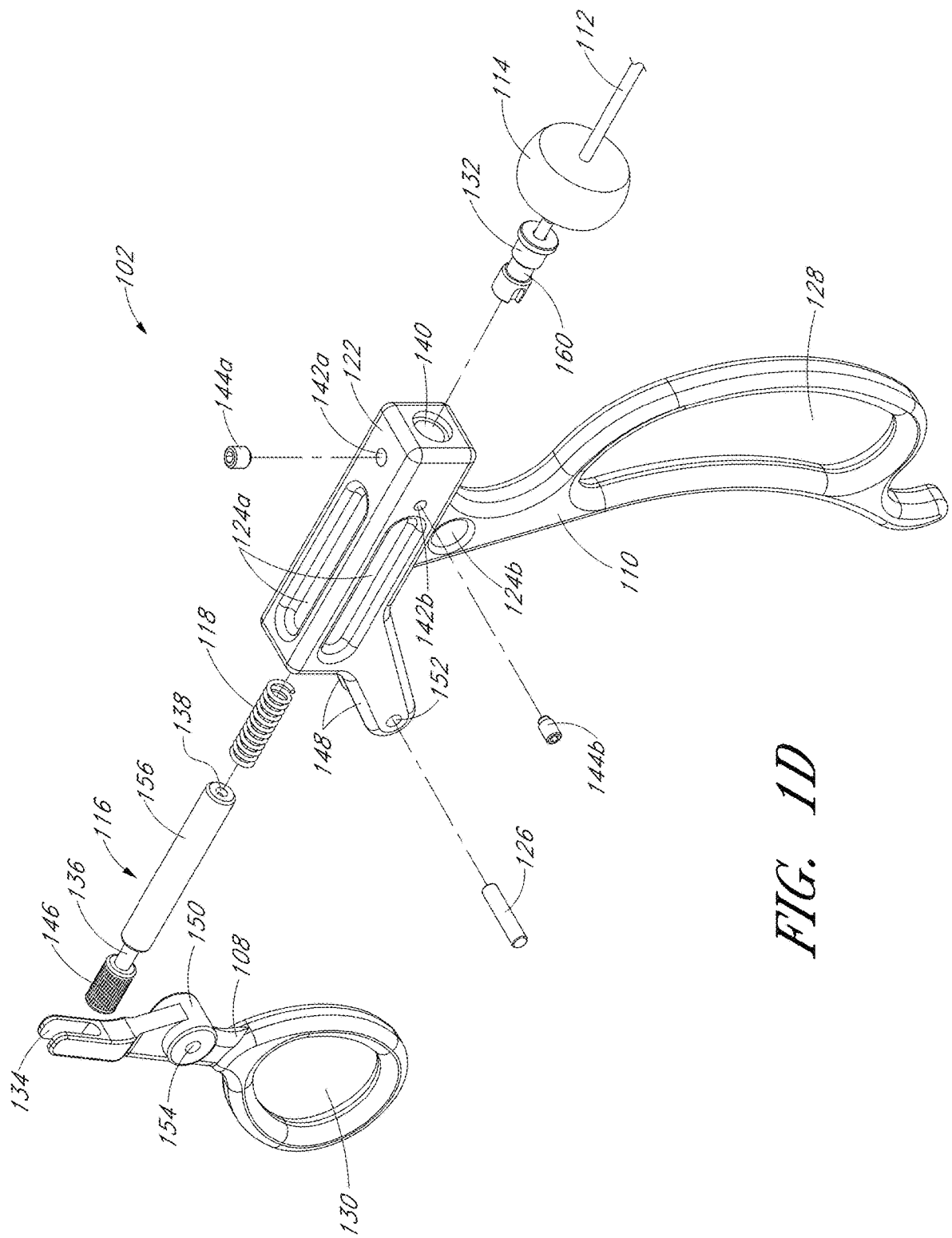
FIG. 1D illustrates an exploded view of the handle portion.
Figure 1E:
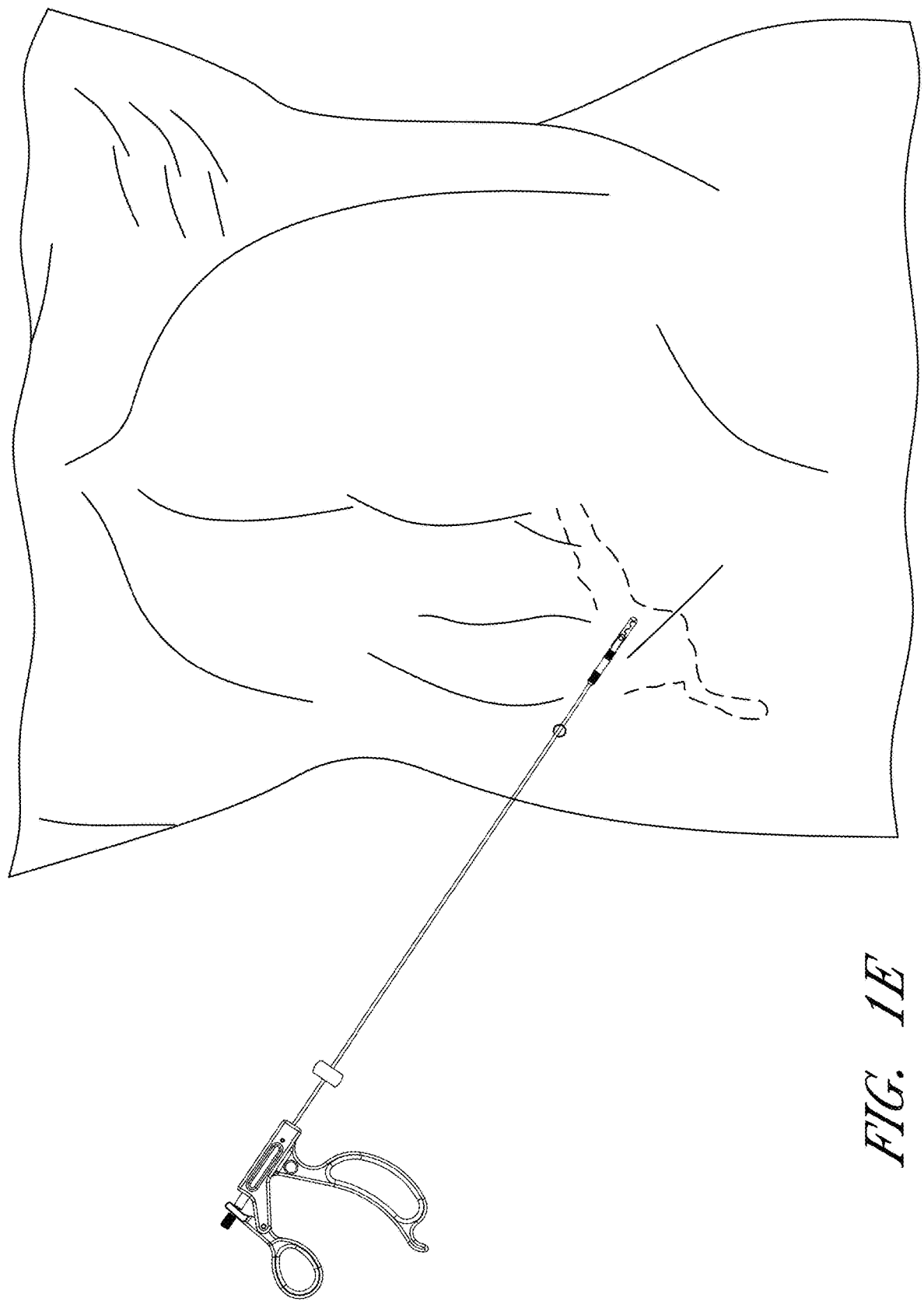
FIG. 1E illustrates the surgical tool introduced into the abdomen near the appendix.
Figure 1F:
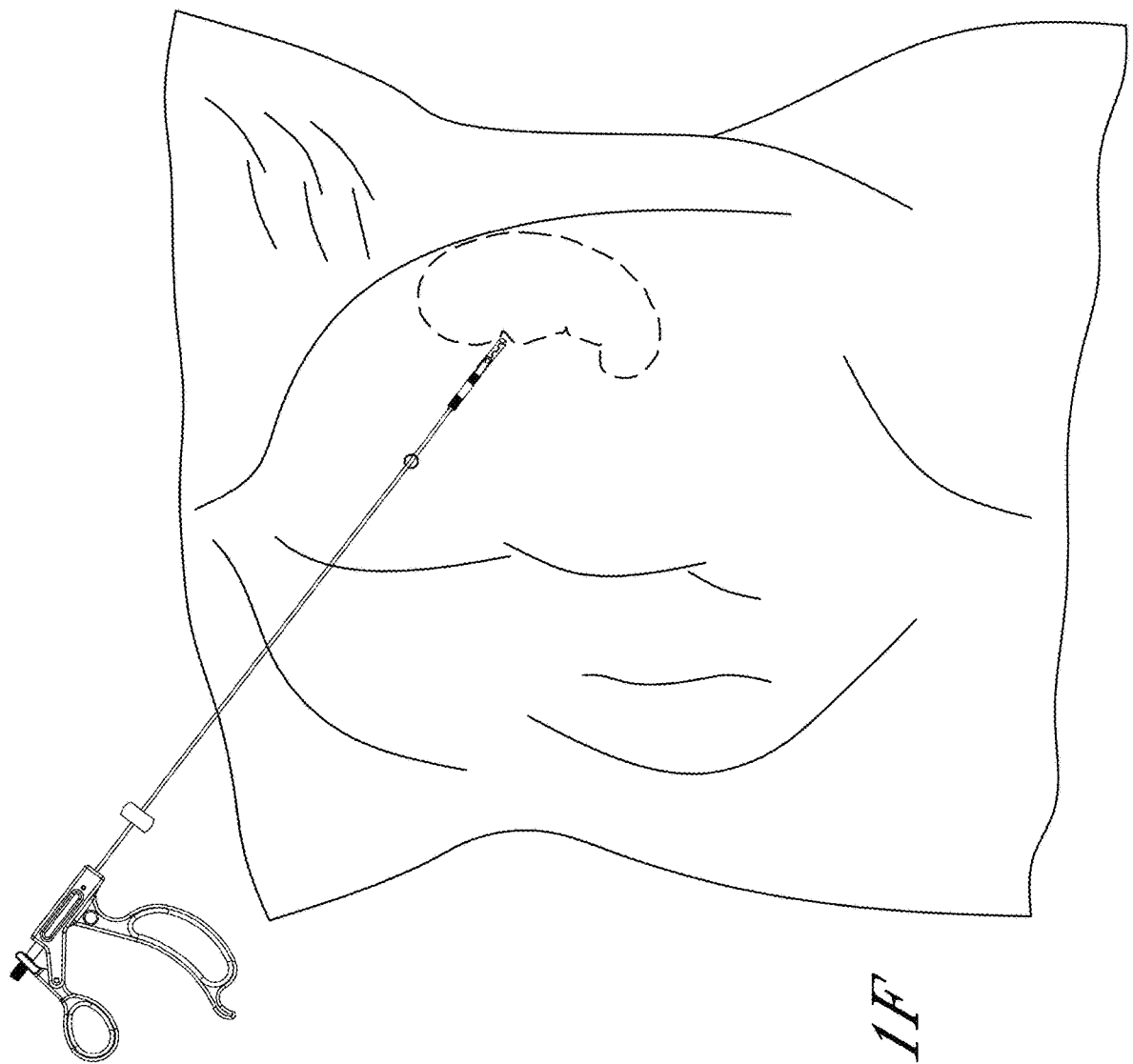
FIG. 1F illustrates the surgical tool introduced into the abdomen near a kidney.

The first handle body 106 can include an extension portion 148 configured to receive an insert portion 150 of the second handle body 108 (see FIG. 1D). For example, the extension portion 148 can include two arms that define an opening for receiving the insert portion 150.

The second handle body 108 can be movable relative to the first handle portion 106. For example, the handle portion 102 can include a pivot pin 126 configured to permit pivotable movement between the first handle body 106 and the second handle body 108. The first and second handle bodies 106, 108 can include openings 152, 154 configured to receive the pivot pin 126. In some instances, the position of the first and second handle bodies 106, 108 can be locked in place to secure the configuration of the working end 104.

In order to facilitate surgeon comfort, the total weight of the handle portion 102 can be reduced by decreasing the dimensions of the handle portion 102 and forming a number of cuts 124a, 124b in the first and second handle bodies 106, 108. The total weight of the handle portion 102 can be less than or equal to about 300 g, and preferably less than or equal to about 200 g. The cuts 124a, 124b can take on various shapes and sizes and can be formed along any part of the handle portion 102. For example, the first handle body 106 can include a number of elongate cuts 124a along the length of the elongate portion 122 and/or a number of circular cuts 124b along the grip portion 110.

As shown in FIGS. 1C-1D, the elongate portion 122 can define a lumen 140. The lumen 140 can be configured to receive at least a portion of each of a proximal handle portion 116, a push rod 120, a spring 118, and/or the shaft portion 112.

The proximal handle portion 116 can extend from the first handle body 106 to the second handle body 108. For example, the lumen 140 can receive a distal segment 156 of the proximal handle portion 116, while the second handle body 108 can include a receiving portion 134 (e.g., indentation, groove, opening, or otherwise) for receiving a reduced thickness portion 136 of the proximal handle portion 116. A proximal segment 146 of the proximal handle portion 116 can extend proximally from the second handle body 108.

The proximal handle portion 116 can be integrally or separately formed from the push rod 120. As shown in FIG. 1C, the distal segment 156 of the proximal handle portion 116 can define a lumen 138 configured to receive a proximal end 158 of the push rod 120. The proximal handle portion 116 can be configured to translate movement from the second handle body 108 to the push rod 120. Pivotable movement of the second handle body 108 can cause axial movement of the push rod 120. In some instances, distal movement of the thumb opening 130 can cause proximal movement of the push rod 120, while proximal movement of the thumb opening 130 can cause distal movement of the push rod 120.

The spring 118 can be disposed between the distal segment 156 of the proximal handle portion 116 and a proximal portion 132 of the shaft 120, and the spring 118 can surround a proximal portion of the push rod 120. In some instances, the spring 118 can be configured to bias the proximal handle portion 116 to a proximal position and/or provide a desired amount of resistance for controlling the working end 104.

Axial movement of the push rod 120 can be configured to control movement of the working end 104. A proximal portion of the push rod 120 can extend through a lumen 140 defined by the elongate body portion 122, while a remaining portion of the push rod 120 can extend through a lumen defined by the shaft portion 112. In some instances, distal movement of the push rod 120 can cause the working end 104 (e.g., graspers, dissectors, scissors, needle driver, clip applier, or otherwise) to an opened configuration, while proximal movement of the push rod 120 can cause the working end 104 to move to a closed configuration.

As shown in FIG. 1D, the elongate portion 122 can define one or more recesses 142a, 142b configured to receive one or more securing pins 144a, 144b. For example, the elongate portion 122 can include a recess 142a along a top surface of the elongate portion 122 and another recess 142b along a side surface of the elongate portion 122. When the pins 144a, 144b are secured within the recesses 142a, 142b, the pins 144a, 144b can secure the proximal portion 132 of the shaft portion 112 to the elongate portion 122.

In some instances, the diameter $D_4$ of the proximal portion 132 of the shaft portion 112 can be greater than the diameter $D_2$ of the remaining portion of the shaft portion 112 (see FIG. 1C). For example, the diameter $D_4$ can be at least about two times greater than $D_2$ or at least about three times greater than $D_2$. The proximal portion 132 can be integrally or separately formed with the remaining portion of the shaft portion 112. As shown in FIGS. 1C-1D, the proximal portion 132 can include at least one region of reduced thickness 160. The regions of reduced thickness 160 can receive at least a portion of the pins 144a, 144b when the pins 144a, 144b are secured within the recesses 142a, 142b.

If the proximal portion 132 has a greater diameter than the remaining portion of the shaft portion 112, then the lumen 140 can have a diameter $D_1$ that is larger than the diameter $D_2$ of the remaining shaft portion 112. In some instances, the diameter $D_1$ can be at least about 1.5 times larger than $D_2$ and/or less than or equal to about 3 times larger than $D_2$. A larger lumen 140 can reduce the weight of the first handle body 106 and increase surgeon comfort.

The outer diameter $D_2$ of the shaft portion 112 can be less than or equal to about 3.0 mm, less than or equal to about 2.5 mm, less than or equal to about 2.0 mm, or less than or equal to about 1.5 mm. In some instances, the outer diameter $D_2$ of the shaft portion 112 can be about 2.5 mm, about 2.3 mm, or about 2.0 mm. The surgical tool 100 can be introduced into the patient alone or introduced through a port having an inner diameter of less than or equal to about 3.0 mm. An incision sized to receive the tool 100 and/or port can have a length of less than or equal to about 3.0 mm. A small incision having a length of less than or equal to about 3.0 mm can decrease healing time and leave no permanent scar.

Depending on the tool, the shaft portion 112 can have an internal diameter sized to receive the push rod 120, facilitate suction without clogs, or otherwise. For example, if the push rod includes a diameter $D_3$ of less than or equal to about 1.0 mm, then the shaft portion 112 can have an internal diameter of less than or equal to about 1.0 mm. In some instances, the internal diameter of the shaft portion 112 can be about 1.0 mm.

The shaft portion 112 can include a working length $L_2$ configured to provide sufficient length to adequately manipulate the tools, while maintaining a minimum amount of stiffness (see FIG. 1A). The shorter the working length, the more rigid and more effective the surgical tool can be, but shorter working lengths limit port placement options. Accordingly, as shown in FIGS. 1E-1F, it can be desirable for the surgical tool to include a working length $L_2$ sufficiently long to extend from a desirable port location (e.g., a port location desirable for triangulation) and reach the target anatomy, while still leaving enough working length to adequately manipulate the tool. For example, the working length $L_2$ can be at least about 20 cm and/or less than or equal to about 30 cm, preferably, for most procedures, between about 24 cm and about 26 cm. For bariatric procedures, the standard tool length is preferably about 29 cm. Advantageously, if the tool is put in the wrong place, it may be placed in a new position with very little cosmetic impact.

The working length $L_2$ can be at least about 50% of the entire length $L_1$ of the surgical tool 100, at least about 60% of the entire length $L_1$ of the surgical tool 100, or at least about 70% of the entire length $L_1$ of the surgical tool 100. In some instances, the working length $L_2$ can be about 70% of the entire length $L_1$ of the surgical tool. The working length $L_2$ can be at least about three times the length $L_3$ of a proximal portion of the handle portion 102, including the first and second handle bodies 106, 108, or at least about four times the length $L_4$ of the proximal portion of the handle portion 102. The working length $L_2$ can be at least about five times the length $L_4$ of the working end 104, or at least about six times the length $L_4$ of the working end 104. In some instances, the working length $L_2$ can be about seven times the length $L_4$ of the working end 104.

In some scenarios, it may be desirable for the surgical tool 100 to include a stop member 114 configured to maintain the position of the surgical tool 100. The stop member 114 can be disposed coaxially along a portion of the shaft portion 112 and can be movable along the length $L_2$ of the shaft portion 112. During the surgical procedure, after the tool 100 is introduced into the patient, the stop member 114 can be moved to a position external from the patient and adjacent the abdominal wall. The stop member 114 can be sized to support the position of the surgical tool 100 even if the surgeon is not holding on to the surgical tool 100, and the stop member 114 can include a rubber material or any other medical grade metal or polymer capable of supporting the surgical tool 100.

Figure 19:
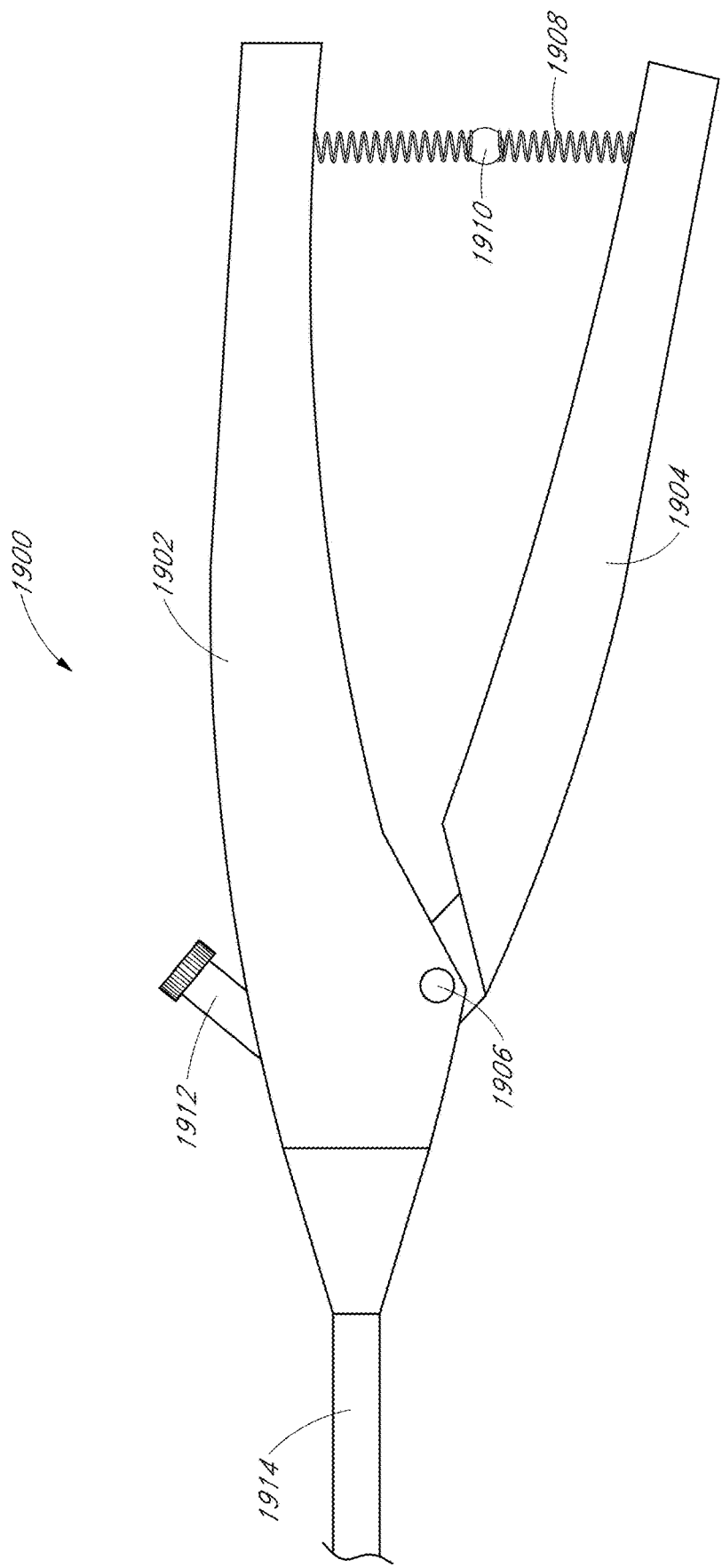
FIG. 19 illustrates another embodiment of an ergonomic handle portion.

FIG. 19 illustrates an alternate handle portion 1900 having an ergonomic design. The handle portion can include a first body portion 1902 pivotably connected to a second body portion 1904 via a pivot pin 1906. The handle body portions 1902, 1904 can be connected by a hinge 1908 pivotable about a central point 1910. In some instances, the hinge 1908 can include a spring mechanism 1908. The spring mechanism 1908 can bias the handle portion to an opened configuration and/or provide a desired amount of resistance for controlling the working end of the surgical tool. In some instances, the handle can include a fluid port 1912 for inputting fluids.

In some configurations, the handle portion (e.g., handle portions 102, 1900, or otherwise) can include one or more shaft portions, each having a shaft diameter of less than or equal to about 1 mm, thus minimizing the likelihood of permanent scars.

FIGS. 20A-20G illustrate a surgical tool 2000 having a handle portion 2002 similar to the handle portion 102. The handle portion 2002 can include a central shaft portion 2008 having a diameter of less than or equal to about 2.5 mm, and preferably less than or equal to about 1 mm, for example, between about 0.8 mm and about 1.0 mm. The central shaft portion 2008 can control movement of a working end 2004, including, but not limited to, any of the working ends described herein. In some embodiments, the central shaft 2008 can provide the working end with one or more degrees of freedom, including, but not limited to, rotation, translation along the tool axis, and/or operation of the working end. The central shaft portion 2008 can connect to the handle portion 2002 as described in connection with the shaft portion 112 and the handle portion 102.

Figure 20A:
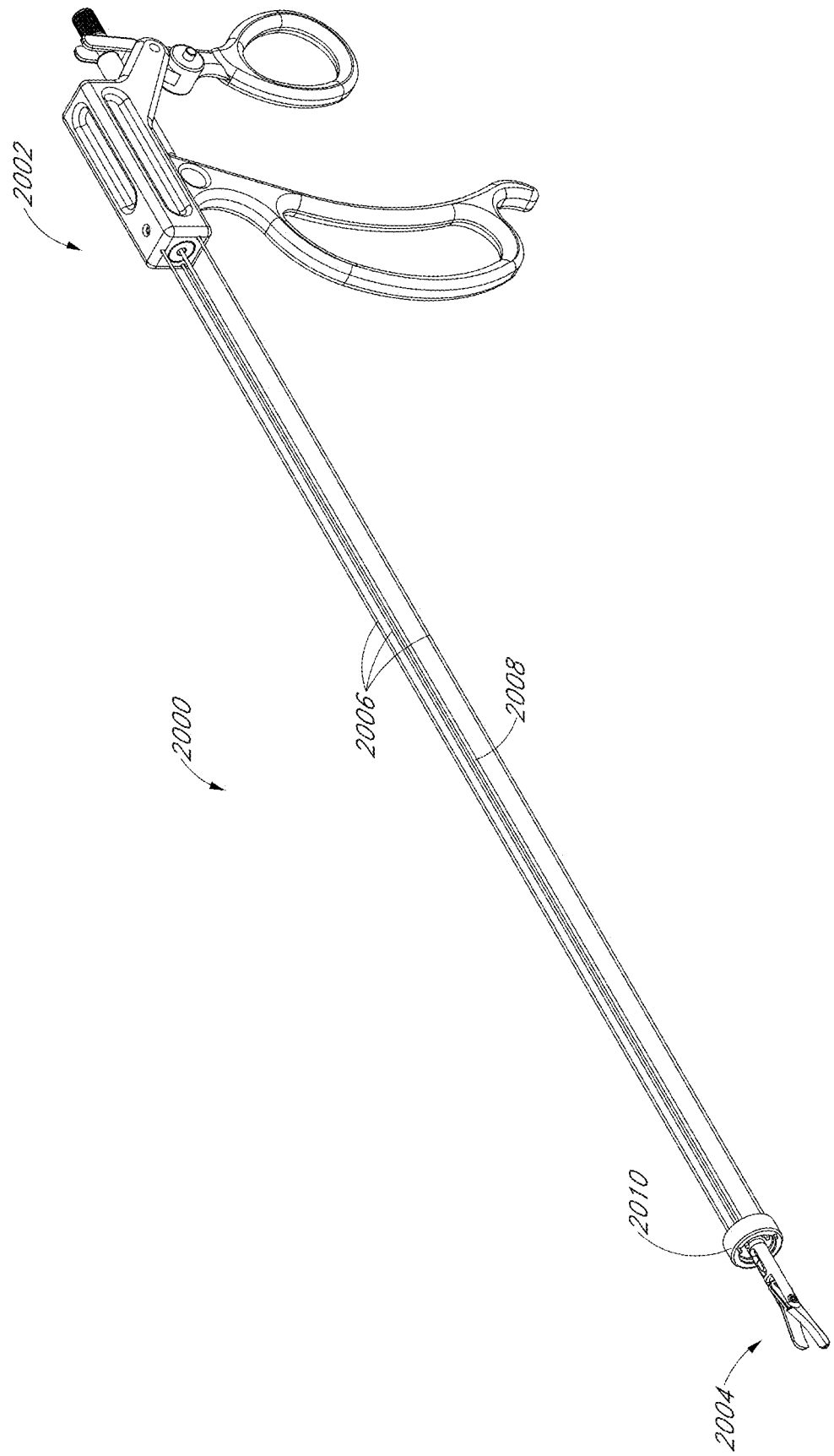
FIG. 20A illustrates a perspective view of another surgical tool.
Figure 20B:
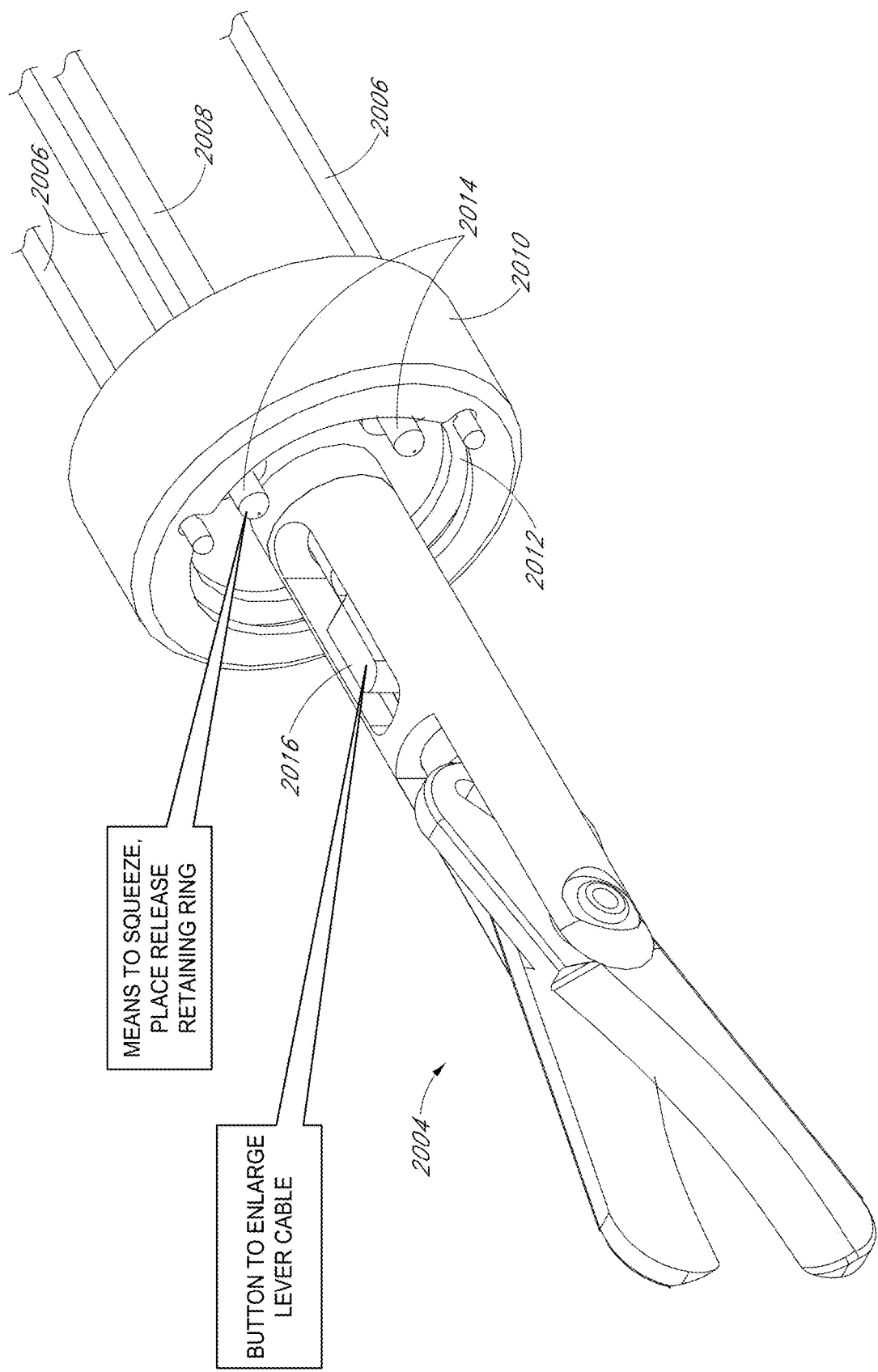
FIG. 20B illustrates an enlarged view of a distal end of the surgical tool shown in FIG. 20A.
Figure 20C:
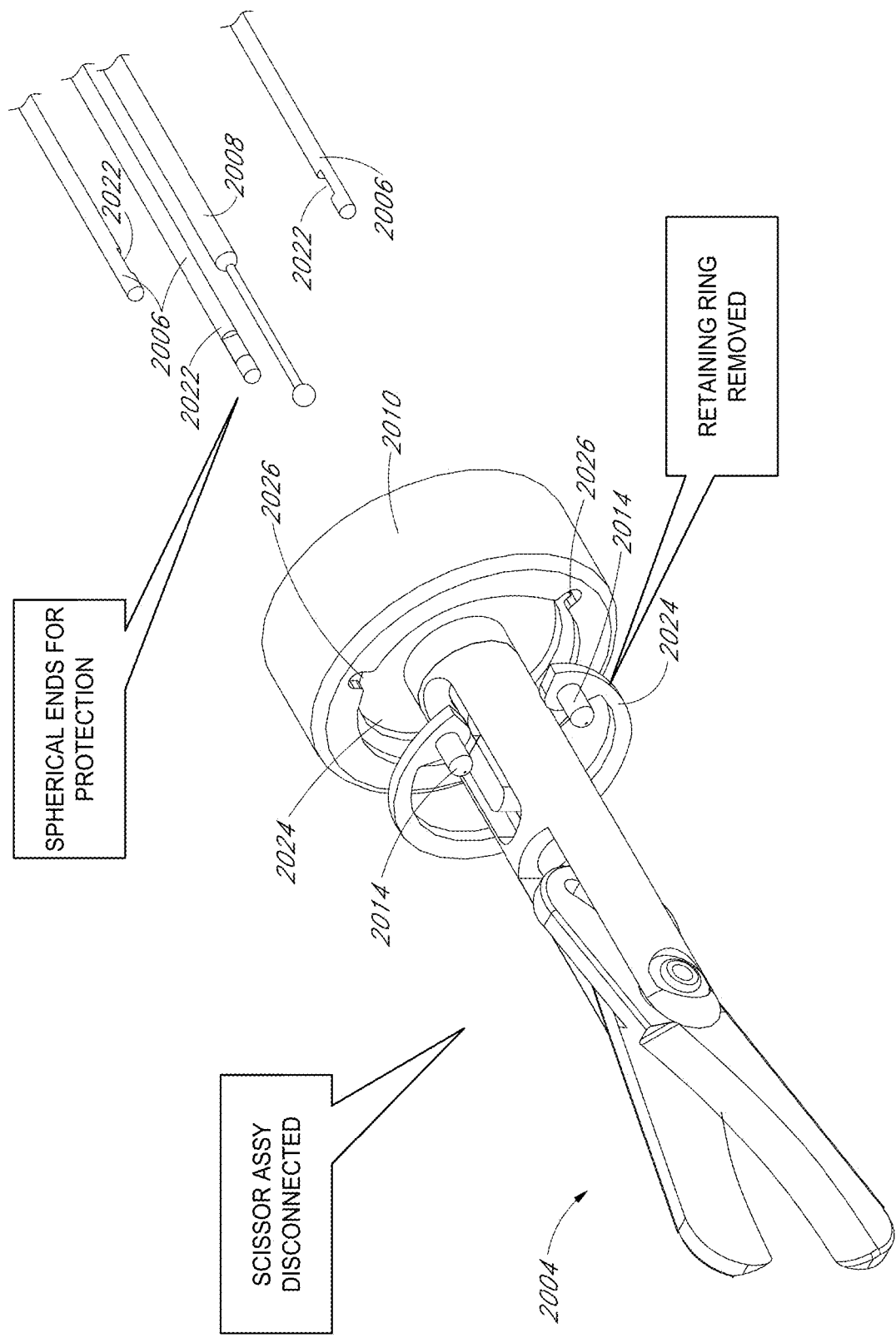
FIG. 20C illustrates an exploded view of the distal end of the surgical tool shown in FIG. 20B.

One or more additional shaft portions 2006 surrounding the central shaft portion 2008 can stabilize the surgical tool. For example, the surgical tool 2000 can include a central shaft portion 2008 surrounded by three evenly spaced additional shaft portions 2006. Each shaft portion 2006, 2008 can be introduced into the abdomen through a separate opening. In some examples, as shown in FIG. 20E, each of the shaft portions can have blunt (e.g., rounded, spherical, etc.) ends for safety. In other examples, each of the shaft portions 2006, 2008 can include a sharpened tip capable of forming the one or more openings through which the shaft portions 2006, 2008 extend. In certain aspects, the shaft portions 2006 can be solid. In certain variants, the shaft portions 2006 can be hollow, for example, to carry cables that can increase functionality of the working end 2004 (e.g., increase degrees of freedom). Additional details regarding methods of achieving multiple degrees of freedom can be found in U.S. Provisional Application No. 61/936,548, filed Feb. 6, 2014, entitled "METHODS AND DEVICES FOR PERFORMING SCARLESS, ROBOTIC ABDOMINAL SURGERY," which is hereby incorporated by reference in its entirety.

During a minimally invasive surgery procedure, all of the shaft portions 2006, 2008 can be simultaneously introduced into the abdomen. Thereafter, a working end can be secured to the central shaft portions 2008. For example, the distal ends of the shaft portions 2006, 2008 can extend through another opening, such as the umbilicus opening, and back out of the abdomen, so the surgeon can secure the working end 2004 to the central shaft portion 2008. Any of the connection features discussed herein can be used to connect the working end to the central shaft portion.

The working end 2004 can include a securing member 2010 for securing the distal ends of each of the additional shaft portions 2006 surrounding the central shaft portion 2008. In some instances, the securing member 2010 can be configured to connect to the central shaft portion 2008. In certain aspects, the securing member 2010 can be configured to fix the position of each of the shaft portions 2006, 2008 to the working end 2004 and relative to each other with a single connection to facilitate ease of use.

Figure 20D:
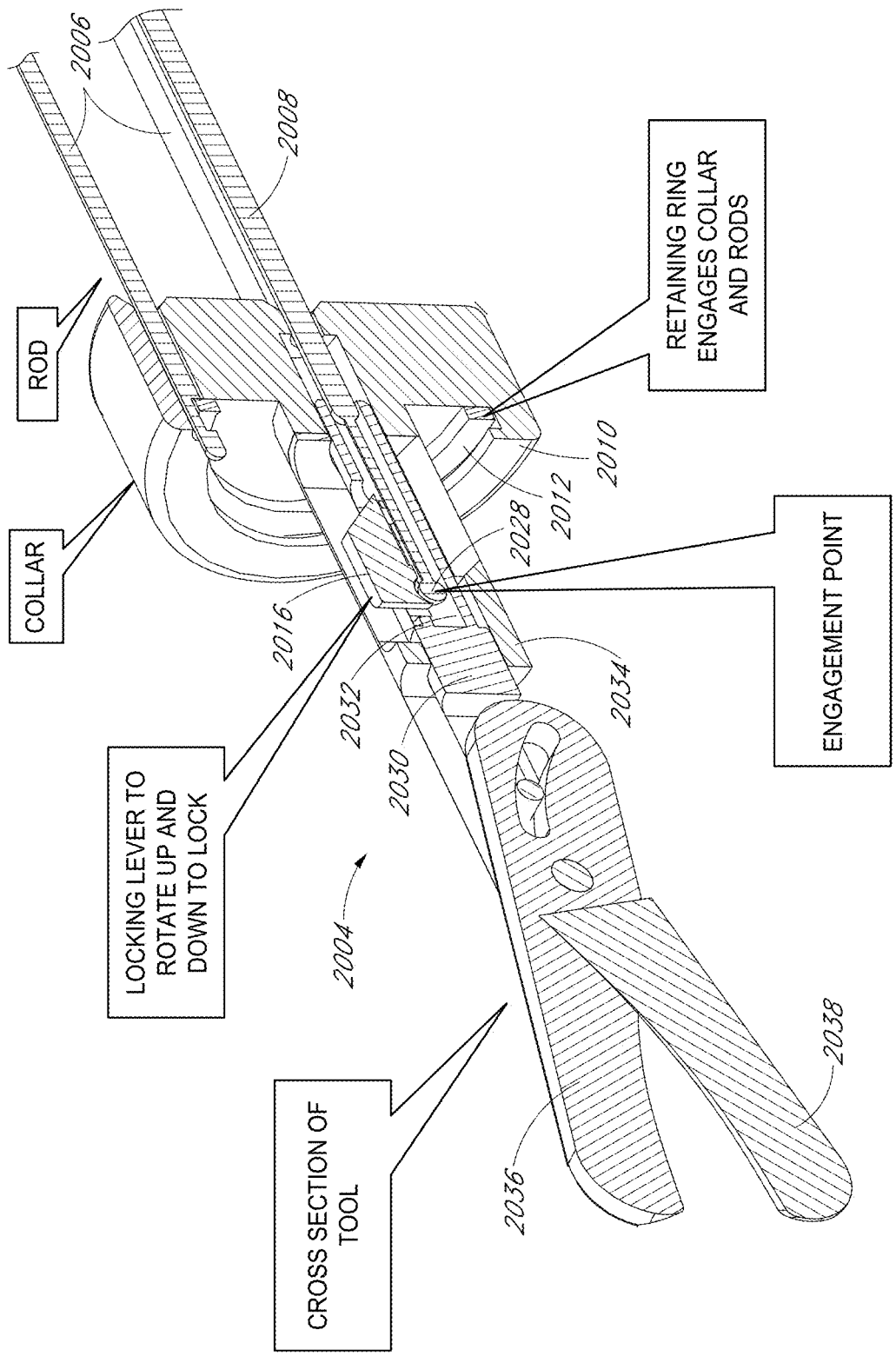
FIG. 20D illustrates a cross-section of the distal end of the surgical tool shown in FIG. 20B.
Figure 20E:
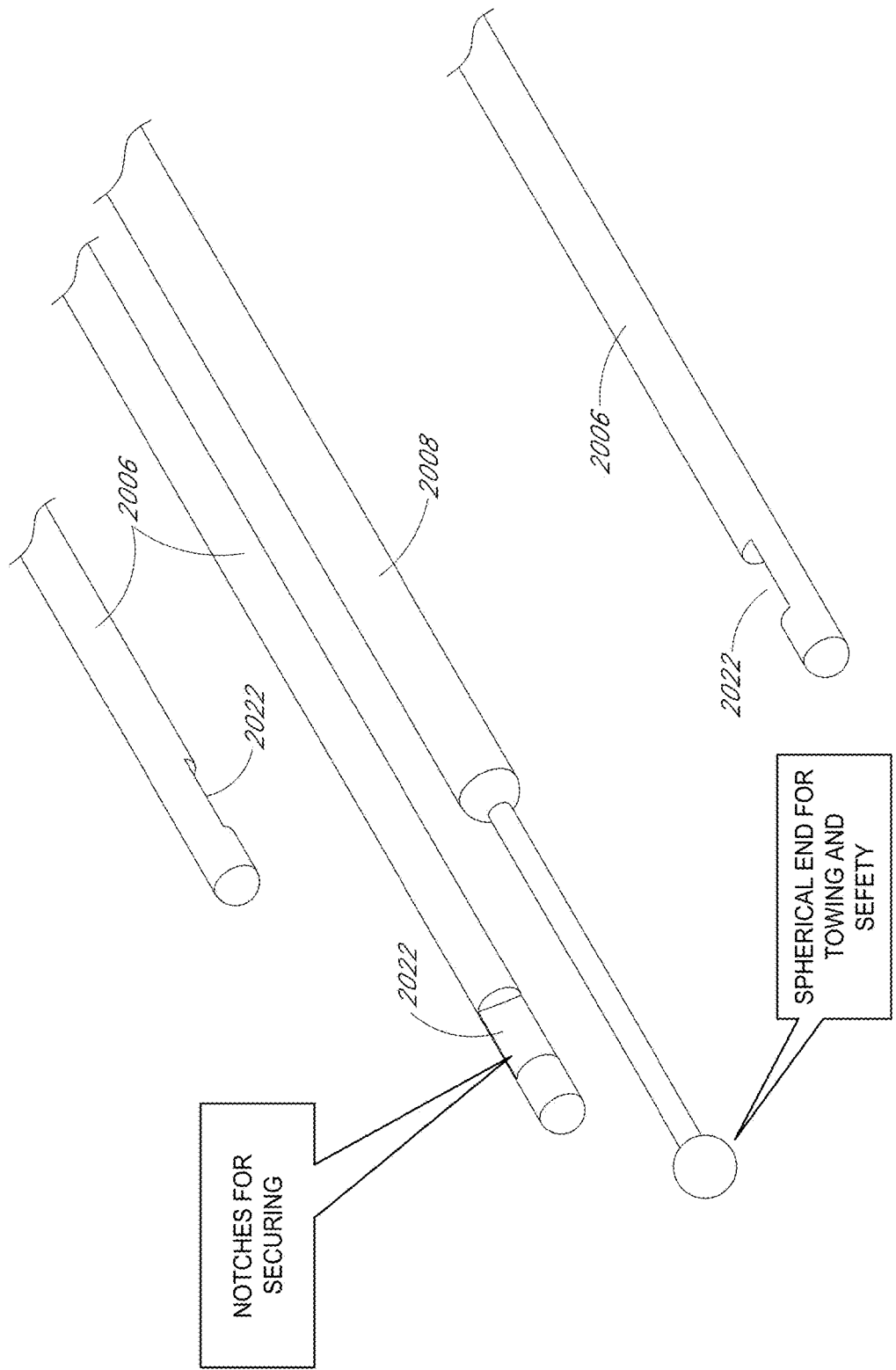
FIG. 20E illustrates distal ends of shaft portions of the surgical tool shown in FIG. 20A.
Figure 20F:
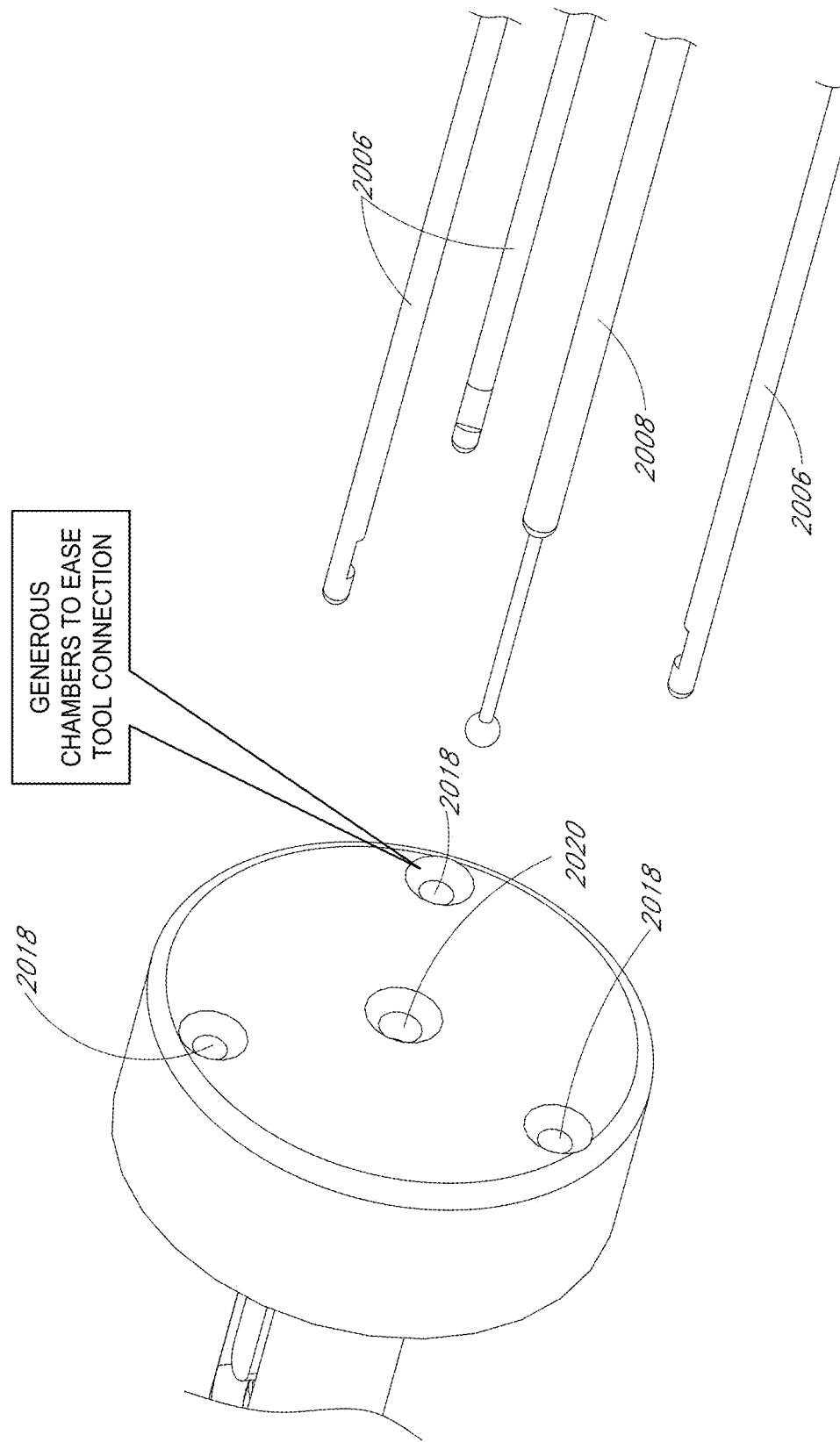
FIG. 20F illustrates the distal ends of the shaft portions and a securing member of the surgical tool shown in FIG. 20A.

As shown in FIG. 20F, the securing member 2010 can be ring-shaped and include a number of openings 2018, 2020 configured to receive the distal ends of each of the additional shaft portions 2006 and the central shaft portion 2008. Each of the openings 2018 can include a chamfered edge to ease the insertion of the shaft portions 2006. A distal face of the securing member 2010 can include a generally circular recess 2024 having grooves 2026 shaped to receive the distal ends of the additional shaft portions 2006 (see FIG. 20C).

Figure 20G:
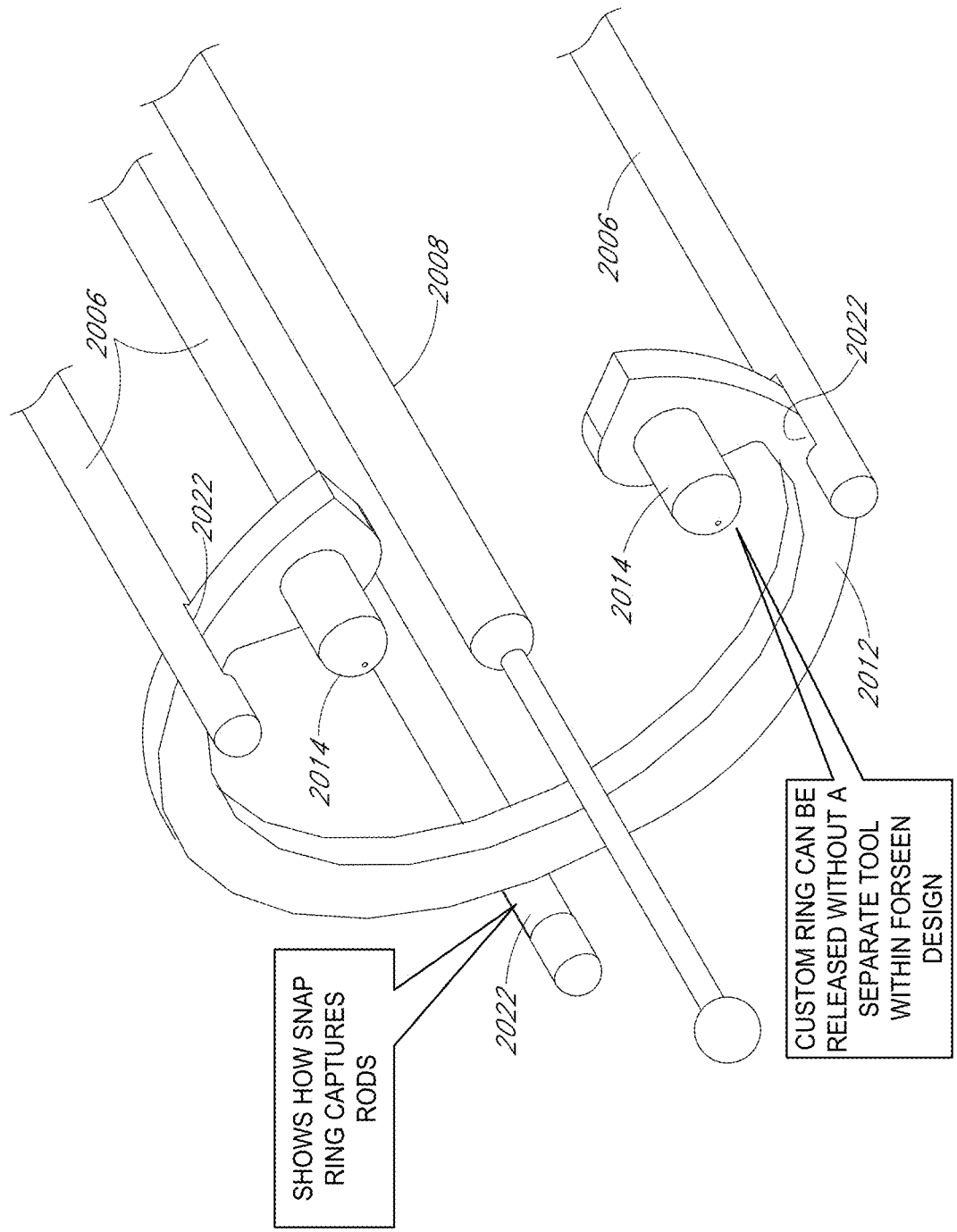
FIG. 20G illustrates the distal ends of the shaft portions and a retaining ring of the surgical tool shown in FIG. 20A.

In some instances, the securing member can include a locking mechanism to fix the positions of the additional shaft portions 2006 in place relative to each other and to the securing member 2010. As shown in FIG. 20G, the surgical tool can include a retaining ring 2012. The retaining ring 2012 can include a generally annular shape and can be shaped to fit within the recess 2024. The retaining ring 2012 can be biased to form a friction fit with the securing member 2010 to secure the addition shaft portions 2006 to the securing member 2010 (see FIG. 20B). The retaining ring 2012 can be removably secured to the securing member 2010 or at least partially fixed to the securing member 2010.

As shown in FIG. 20E, each of the additional shaft portions can include a notch 2022 (e.g., groove, indentation, opening, or likewise) for receiving a portion of the retaining ring 2012. After the securing member 2010 has been connected to each of the additional shaft portions 2006, the retaining ring 2012 can be positioned to secure the distal ends of the shaft portions 2006 to the securing member 2010, as shown in FIG. 20B. To release the retaining ring 2012, the user can push the nubs 2014 toward each other and remove the ring 2012. In certain variants, the retaining ring 2012 can be rotated or otherwise adjusted to release the shaft portions 2006.

As shown in FIG. 20D, the working end 2004 can be a pair of scissors. The working end 2004 can include a housing 2034 configured to receive a slide member 2030. The slide member 2030 can define a receiving portion 2032 shaped to receive a distal portion 2028 of the central shaft portion 2008, which, as shown in the figures, can include a generally spherical shape to assist with controlling the working end 2004. The distal portion 2028 can be introduced into the slide member 2013 from a proximal end of the slide member 2030. Movement of the central shaft portion 2008 can cause corresponding movement of the slide member 2030 to operate the working end 2004.

In some instances, the working end 2004 can include an actuator 2016 to secure or release the distal portion 2028 of the central shaft portion 2008 to the slide member 2030. Pressing the actuator 2016 downward can lock the distal portion 2028 in place.

The receiving portion 2032 and the distal portion 2028 can be shaped such that proximal and distal movement of the distal portion 2028 translates to proximal and distal movement of the slide member 2030. Axial movement of the slide member 2030 can move the jaw members 2036, 2038 between opened and closed configurations. Different types of jaw members are described in further detail below.

Graspers and Related Tools

Figures 2C, 2D:
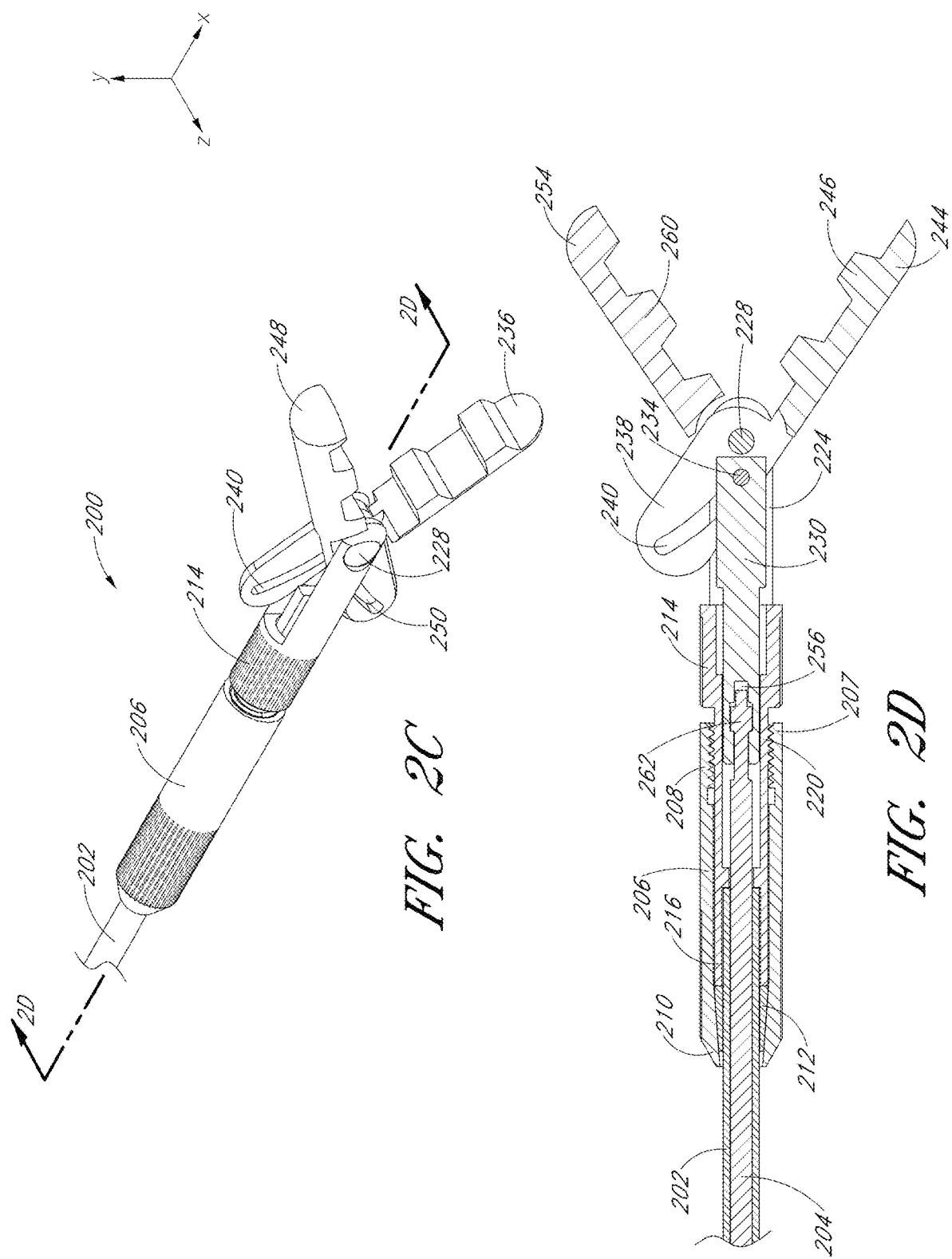
FIG. 2C illustrates a perspective view of the grasper tool shown in FIG. 2A in an opened configuration.
FIG. 2D illustrates a cross-section of the grasper tool shown in FIG. 2C taken along line 2D-2D.

FIGS. 2A-2E illustrate a grasper tool 200 configured to move between a closed configuration (FIGS. 2A-2B) and an opened configuration (FIGS. 2C-2D). The grasper tool 200 can have a generally cylindrical shape in its closed configuration. The grasper tool 200 can have a diameter $D_{200,1}$ of at least about 3 mm and/or less than or equal to about 10 mm, and a length $L_{200,1}$ of at least about 1 cm and less than or equal to about 4 cm.

The grasper tool 200 can be secured to a handle, for example, the handle portion 102, such that the handle can control movement of a push rod 204. Axial movement of the push rod 204 can move the grasper tool 200 between the closed configuration (FIGS. 2A-2B) and the opened configuration (FIGS. 2C-2D).

To assemble the surgical tool, a nut 206 and a ferrule 212 can be positioned coaxially along a portion of the shaft portion 202. In some instances, the ferrule 212 can be secured to the nut 206 (e.g., welded) prior to positioning the nut along the portion of the shaft portion 202. Thereafter, a distal portion 262 of the push rod 204 can be inserted into the receiving portion 218 of the housing 214 from a lateral direction to mate with a receiving portion 256 of the slide member 230 (see FIG. 2E). In this configuration, the housing 214 can be positioned such that a proximal end 216 of the housing 214 abuts a distal end of the ferrule 212. Once the push rod 204 mates with the slide member 230, the nut 206 can be moved distally until a distal portion 208 of the nut 206 threadably engages the housing 214, and a proximal portion 210 of the nut 210 can form a friction fit with the shaft portion 202 via the ferrule 212. Each of these components will be described in further detail below.

In general, the nut 206 can be generally elongated and can include a distal portion 208 and a proximal portion 210. The nut 206 can define a lumen through which the shaft portion 202 extends. In some instances, an inner and/or outer diameter of the proximal portion 210 can be tapered such that the inner and/or outer diameter of the proximal portion 210 is smaller than the inner and/or outer diameter of the distal portion 208 of the nut 206. The distal portion 208 of the nut 206 can include a threaded portion 207 configured to engage a threaded region 220 of the housing 214. The most distal threads 207 can form a friction fit with the threaded portion 220 to prevent the grasper tool 200 from disassembling within the patient. In some instances, at least an outer surface of 206 can include a textured portion 209 (e.g., ribbed). The textured portion 209 can make it easier to grasp the nut 206.

The ferrule 212 can be disposed proximal to the housing 214 and can include a shape generally contoured to the internal surface of the proximal end 210 of the nut 206. For example, the ferrule 212 can be generally tapered with a proximal end having a diameter smaller than a distal end of the ferrule 212. In some configurations, the angle of the ferrule can be at least about 5 degrees and less than about 90 degrees downward relative to a distal face of the ferrule 212. In some configurations, the angle can be between about 5 degrees and about 45 degrees, or between about 45 degrees and 90 degrees. In some instances, the angle can be about 45 degrees. In some instances, this ferrule 212 can be secured to the nut 206 (e.g., welded, glued, or otherwise) or integrally formed with the nut 206 to prevent inadvertent dislodgment of the ferrule 212 inside the patient.

In some instances, the ferrule 212 can include an adjustable diameter and/or be configured to be tightly secured to the shaft. For example, the ferrule 212 can include an elongate slit 268 positioned such that the proximal end 210 of nut 206 can reduce a diameter of the ferrule 212 when the nut 206 engages the housing 214. In some configurations, the ferrule can include multiple slits, including, 2, 3, 4, 5, 6, 7, 8, or more slits. For example, the ferrule 212 can include four different slits positioned at 90 degree increments to allow easier coaptation. In some configurations, the ferrule 212 can include regions of more flexible material rather than slits 268.

Figure 2E:
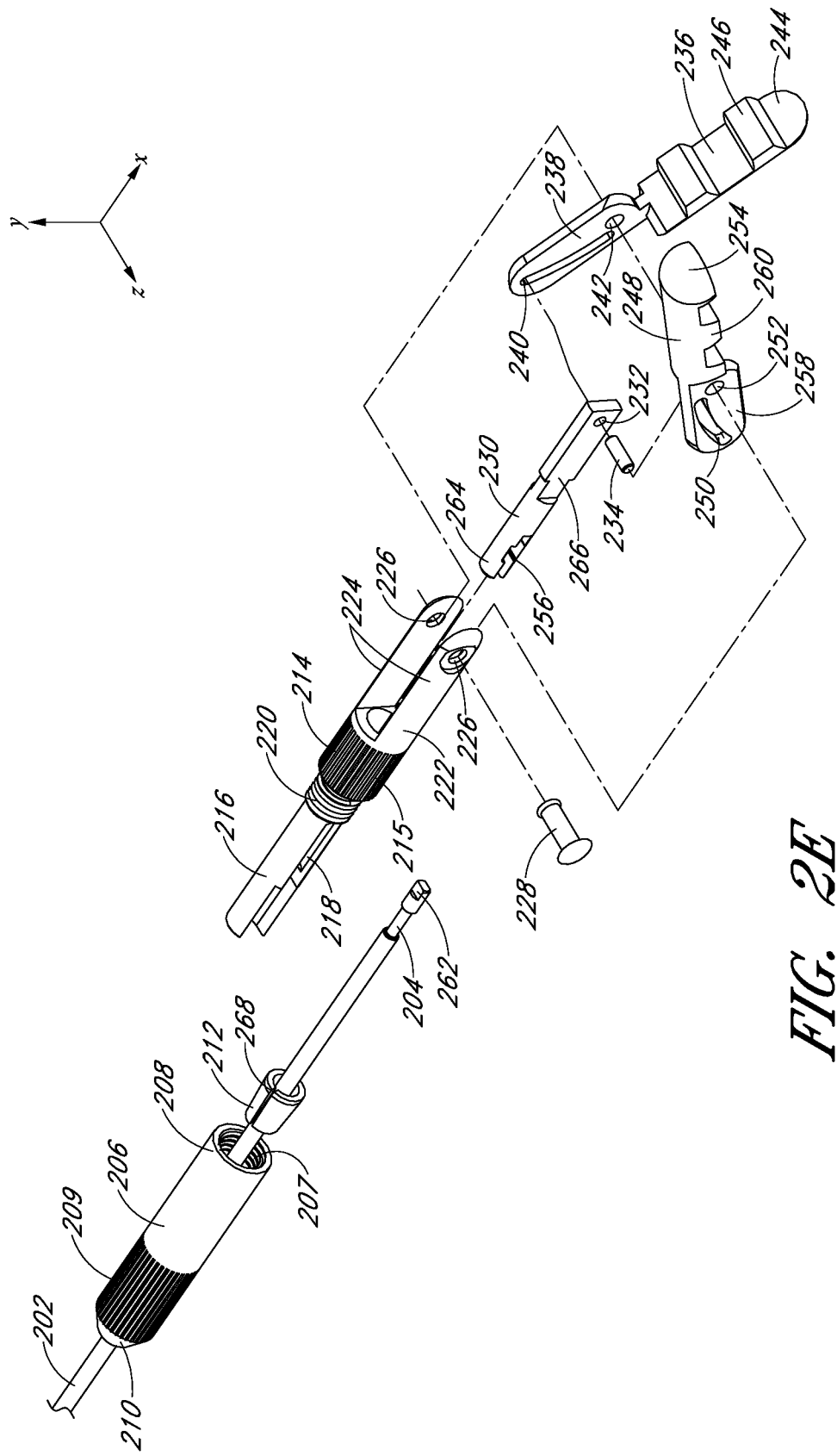
FIG. 2E illustrates an exploded view of the grasper tool shown in FIGS. 2A-2D.
Figures 3A, 3B:
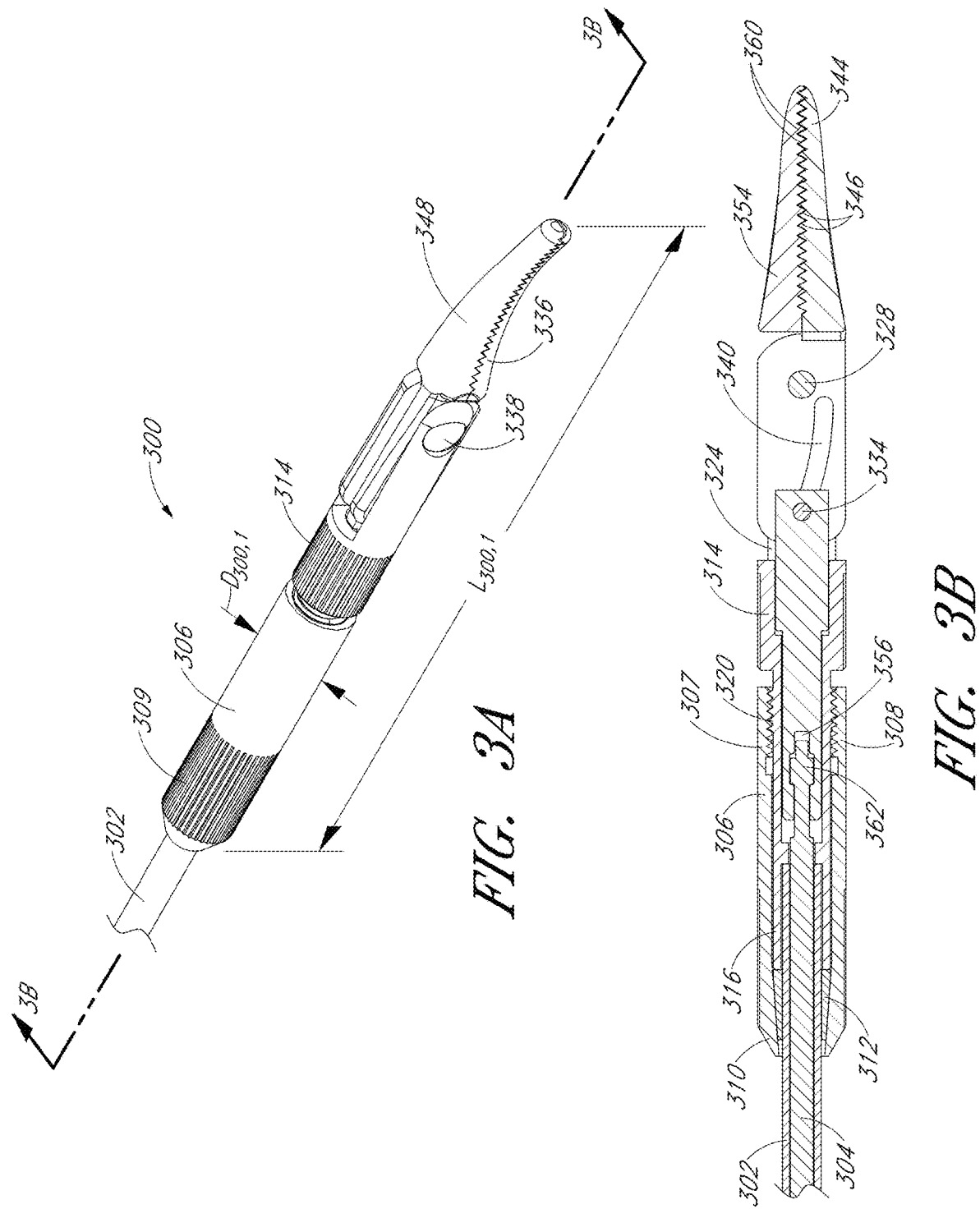
FIG. 3A illustrates a perspective view of a dissector tool in a closed configuration.
FIG. 3B illustrates a cross-section of the dissector tool shown in FIG. 3A taken along line 3B-3B.
Figure 3E:
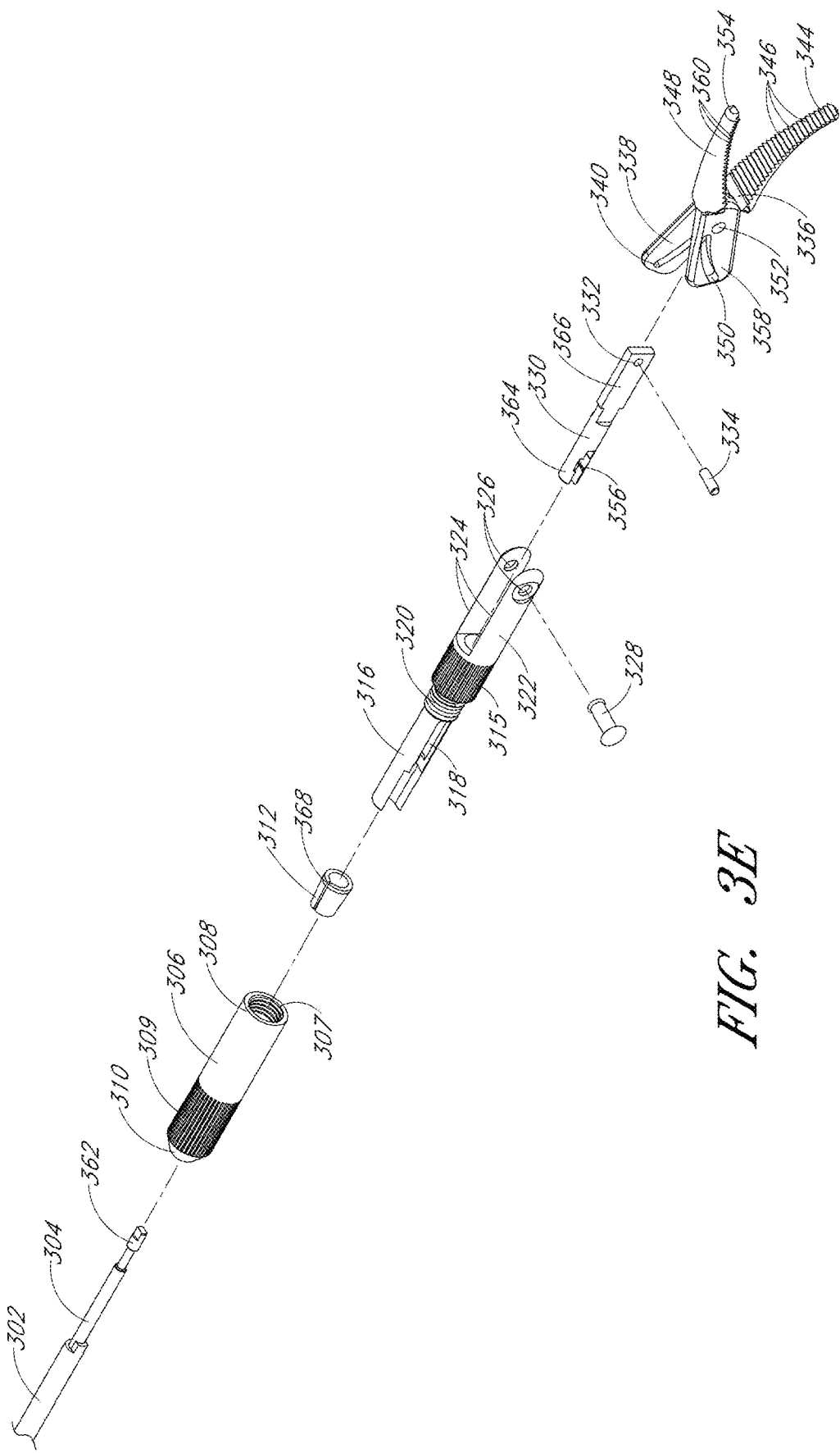
FIG. 3E illustrates an exploded view of the scissor tool shown in FIG. 3A.

FIG. 2F illustrates an alternate ferrule 212a to the ferrule 212 shown in FIG. 2E. The ferrule 212a can include a similar conical shape as ferrule 212 and can include a number of elongated slots extending along a partial length of the ferrule. The slots can be sized and positioned to optimize the friction fit between the nut 206 and the shaft portion 202. For example, as shown in FIG. 2F, the ferrule 212a can include one or more elongate slots 268a along a distal portion of the ferrule 212a and/or one or more elongate slots 268b along a proximal portion of the ferrule 268b. In certain aspects, the ferrule 212a can include two elongate slots 268a and two elongate slots 268b.

The combination of the ferrule 210 and the threaded engagement between the nut 206 and the housing 214 can help ensure that the grasper tool 200 does not disengage from the handle. In addition, the coaxial placement of the nut 206, the ferrule 212, and the housing 214 along the shaft portion 202 makes it more difficult for those components to fall off during the procedure.

The housing 214 can define a lumen configured to receive a distal portion 262 of the push rod 204 and a proximal section 230 of the slide member 230. For example, the push rod 204 can enter the lumen from a receiving portion 218. The receiving portions 218, 256 can be configured such that the distal portion 262 of the push rod 204 can enter both the housing 214 and the slide member 230 from a lateral direction.

In some configurations, the shaft portion 202 can include a diameter of about 2.5 mm and can be configured for insertion into the abdomen without a port. In these configurations, the distal portion 262 can include a diameter of less than or equal to about 2.25 mm.

Although not shown in the drawings, in some configurations, the grasper tool 200 can include a rotatable component surrounding the receiving portion 256 and/or receiving portion 218. After the push rod 204 is introduced one or both of the receiving portions 218, 256, the rotatable component can be rotated, for example, 90 degrees, to close one or both receiving portions 218, 256 to prevent the tool 200 from disassembling from the shaft portion 202. To remove the grasper tool 200, the rotatable portion can be rotated back to permit the push rod 204 to be removed.

The slide member 230 can have a generally cylindrical proximal portion 264 defining the receiving portion 256 for receiving the distal portion 262 of the push rod 204. The distal portion 266 of the slide member 230 can be generally planar and define the opening 232 for receiving the pin 234, which slidably connects with the slide member 230 and the jaw members 236, 248.

The distal portion 262 of the push rod 204 can be configured to mate with the receiving portion 256 of the slide member 230 at a position within the housing 214. For example, the distal portion 262 of the push rod 204 can be shaped such that proximal and distal movement of the push rod 204 causes proximal and distal movement of the side member 230. In some instances, as shown in FIG. 2E, the distal portion 262 of the push rod 204 can have one or more regions of reduced thickness. For example, the junction between the distal portion 262 and the remaining portion of the push rod 204 can include a 90 degree step to prevent slippage between the receiving portion 256 and the distal portion 262 of the push rod 204. In some instances, the distal tip of the distal portion 262 can be tapered to facilitate insertion of the push rod 204 directly through the tissue without any other tools.

The housing 214 can include a distal portion 222 having two arms 224 that define a receiving portion configured to receive the proximal portion 264 of the slide member 230. Each arm 224 can include an opening 226 configured to receive a pin 228, and each jaw member 236, 248 can define an opening 242, 252 configured to receive the pin 228. The pin 228 can secure the housing 214 to the jaw members 236, 248. At least a portion of an outer surface of the distal portion 222 can include a textured surface 215 (e.g., ribbed). The textured surface 215 can be positioned between the threaded region 220 and the arms 224.

Each jaw member 236, 248 can include a proximal portion 238, 258 and a distal portion 244, 254. In some instances, the distal portions 244, 254 can be at least partially rounded and/or the proximal portions 238, 258 can be generally planar. The jaw members 236, 248 can be positioned such that the proximal portions 238, 258 overlap each other along an x-y plane, while the distal portions 244, 254 overlap each other along an x-z plane. To facilitate this configuration, the proximal portions 238, 258 can include a width that is less than a width of the distal portions 244, 254.

The distal portion 244, 254 of each jaw member 236, 248 can include one or more teeth 246, 260. The teeth 246, 260 can be disposed along surfaces of the distal portions 244, 254 that are generally orthogonal to side walls of the proximal portions 238, 258. In some instances, the teeth 246, 260 can be shaped to grasp tissue without puncturing the tissue.

Each proximal portion 238, 258 can include an elongate slot 240, 250. In certain aspects, the elongate slots 240, 250 can each include a cam surface configured such that movement of a pin 234 along the elongate slots 240, 250 causes rotation of the jaw members 236, 248 to open and close the jaws of the instrument. The pin 234 can extend through an opening 232 of the slide member 230 and through each elongate slot 240, 250 such that the distal portion 266 of the slide member 230 is disposed between the proximal portions 238, 258 of the jaw members 236, 248. In certain aspects, the first jaw member 236 can include an elongate slot 240 having a distal end that is closer to a bottom surface of the first jaw member 236 than a proximal end of the jaw member 240. Conversely, the second jaw member 248 can include an elongate slot 250 having a proximal end closer to a bottom surface of the second jaw member 248 than a distal end of the elongate slot 250.

In some procedures, the grasper tool 200 can be secured to a shaft portion 202 prior to introducing the surgical tool into the patient. In other procedures, the shaft portion 202 can be first introduced through a first opening in the abdominal wall without the grasper tool 200. The distal end of the shaft portion 202 can then be introduced through a second opening and back out of the patient. Thereafter, the grasper tool 200 can be secured to the shaft portion 202, and the grasper tool 200 can be pulled back through the second opening and into the patient.

After the grasper tool 200 has been introduced into the surgical environment, the grasper tool 200 can be used to grab the target anatomy. Axial movement of the push rod 202 can move the slide member 230 in an axial direction. Depending on the configuration of the elongate slots 240, 250, distal movement of the push rod 204 can move the pin 234 distally along the elongate slots 240, 250 and cause the jaw members 236, 248 to move to an opened configuration, while proximal movement of the push rod 204 can move the pin 234 proximally along the elongate slots 240, 250 to close the jaw members 236, 248. Other configurations can be designed such that proximal movement of the push rod 204 can open the jaw members 236, 248 and distal movement of the push rod 204 can close the jaw members 236, 248.

The present disclosure should not be construed to be limited to the types of graspers illustrated in FIGS. 2A-2E. The jaw members 236, 248 and teeth 246, 260 can take on various configurations. As shown in FIG. 2G, the jaw members 236, 248 can take the form of a clip applier, for example, for use with Hem-o-lok®, LIGACLIP®, Hemoclip®, or other clips. The clip applier can include jaw members having proximal portions 244a, 254a, each having teeth 246a, 260a for grasping the clip. Other teeth shapes 246a, 260a are also possible depending on the shape of the clip.

In other configurations, the graspers can include one or more recesses along an inner surface of the jaw members and/or be shaped such that there is a space between the jaw members when the graspers are in a closed configuration. These graspers can be useful for grasping, for example, a portion of the bowel within the space without traumatically injuring the bowel. As another example, the teeth 246, 260 can vary along a length of the jaw members 236, 248. For instance, the teeth 246, 260 can be serrated to securely hold the target anatomy. In some instances, the grasper tool can include sharper teeth at a distal end of the grasper tool to permit a firm grasp when removing the target anatomy (e.g., uterus, gallbladder, or otherwise). In some instances, the graspers can include Debakey type teeth (e.g., teeth shown in FIGS. 3A-3E) to provide a secure and atraumatic grasping. In some instances, the teeth 246, 260 can be rounded for grasping blood vessels. In some instances, the grasper tool can be fenestrated along a length of the jaw members and/or include a fenestrated tip.

In some instances, the grasper tool 200 can be a needle driver configured to hold a needle. For example, as shown in FIGS. 2H-2J, the proximal portions of the jaw members 244b, 254b can include a generally curved shape and a blunt distal end. The jaw members can include a number of teeth 260 separated by grooves extending along one or more directions. These grooves can make it easier to grab the needle during suturing.

In some instances, the handle portion 102 can include a locking mechanism, for example, a ratcheting mechanism, lever, detent, or otherwise, to lock the position of the jaw members 236, 248 until manually released.

FIGS. 3A-3E illustrate a dissector tool 300 configured to removably engage with a handle, such as the handle portion 102. The dissector tool 300 can engage the handle similarly to the method described in connection with FIGS. 2A-2E. In addition, the dissector tool 300 can be configured to open (FIGS. 3C-3D) and close (FIGS. 3A-3B) in a manner similar to FIGS. 2A-2E. Numerical references to the components are the same as previously described, except that the references are in the 300s instead of the 200s.

Unlike the grasper tool 200, the dissector tool 300 can include curved jaw members 336, 348 to facilitate, for example, dissection of vessels from other structures, separation of tissue planes, stabilization of tissues, and in some instances, suture grasping and knot tying. As shown in FIGS. 3A-3E, the curved jaw members 336, 348 can be tapered in a distal direction. Each jaw member can include one or more teeth 346, 360 for grasping. These teeth 346, 360 can be thinner than the teeth 246, 260 of the grasper tool 200. Alternatively, the teeth 346, 360 can take on any configuration described above in connection with grasper tool 200.

Although FIGS. 3C and 3D show both jaw members 336, 348 moving relative to each other, in some configurations, only one of the jaw members 336, 348 moves, while the other jaw member remains stationary.

The present disclosure should not be construed to be limited to the types of dissectors illustrated in FIGS. 3A-3E. In some instances, the jaw members 336, 348 can include a right angle to dissect around blood vessels.

FIGS. 4A-4E illustrate a scissor tool 400 configured to removably engage with a handle, such as the handle portion 102. The scissor tool 400 can engage the handle similarly to the method described in connection with FIGS. 2A-2E. In addition, the scissor tool 400 can be configured to open (FIGS. 4C-4D) and close (FIGS. 4A-4B) in a manner similar to FIGS. 2A-2E. Numerical references to the components are the same as previously described, except that the references are in the 400s instead of the 200s.

In some instances, the scissor tool 400 can include a slide member 430 as shown in FIG. 4E. The slide member 430 can include a proximal portion 464 having a receiving portion 456 configured to receive a distal portion 464 of a push rod 404. A distal portion 466 of the slide member 430 can include two arms 470 that define an opening configured to receive proximal portions 438, 458 of the jaw members 436, 448. Each arm 470 can define an opening 434 configured to receive a pin 434. The pin 434 can extend through each of the openings 434 and through the elongate slots 440, 450 of the jaw members 436, 448.

In some instances, the scissor tool 400 can include one or more gaskets 429 (e.g., o-rings). The gaskets 429 can be used to maintain the connection between the pin 428 and the housing 414.

Unlike the grasper tool 200, the scissor tool 400 can include jaw members 436, 448 without any teeth. Instead, the jaw members 436, 448 include a sharpened blade configured to cut tissue or sutures. In addition, the jaw members 436, 448 can have rounded ends to protect the tissue when the scissor tool 400 is introduced into the patient, and during use of the scissors inside the patient.

The present disclosure should not be construed to be limited to the types of scissors illustrated in FIGS. 4A-4E. Various other scissor shapes can be imagined. For example, the distal portions 444, 454 can be tapered and/or include a sharp distal tip that can be used to cut very fine surfaces, such as, for tapering small blood vessels, or tapering the ureter or appendix for later anastomosis. In some configurations, the distal tip portions of the jaw members 436, 448 can be slightly bent inward toward each other to create the friction required for cutting structures internally without the surgeon applying this force from the handle. In some configurations, the jaw members 436, 448 can include a combination of a scissor tool and a grasper tool.

Figure 5A:
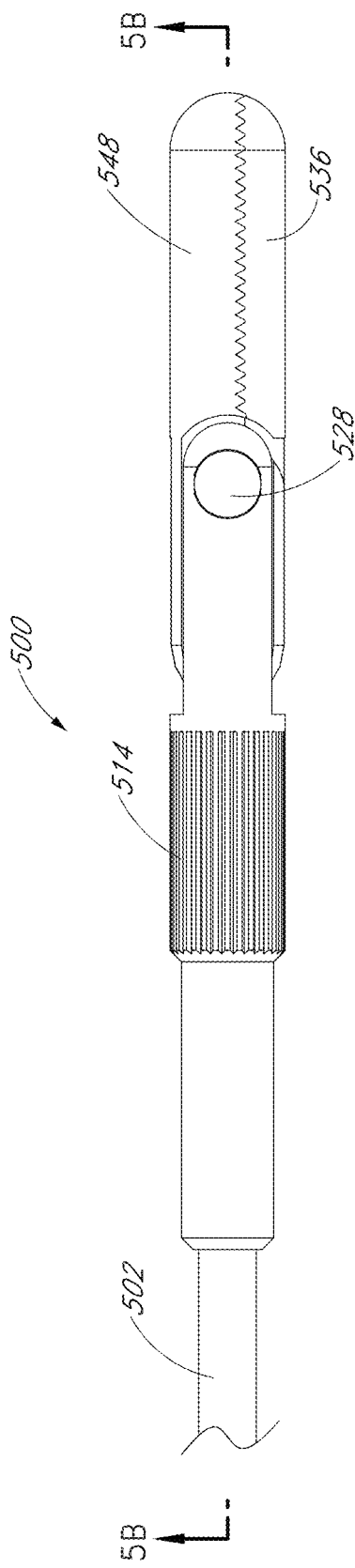
FIG. 5A illustrates an elevational view of another grasper tool.
Figure 5B:
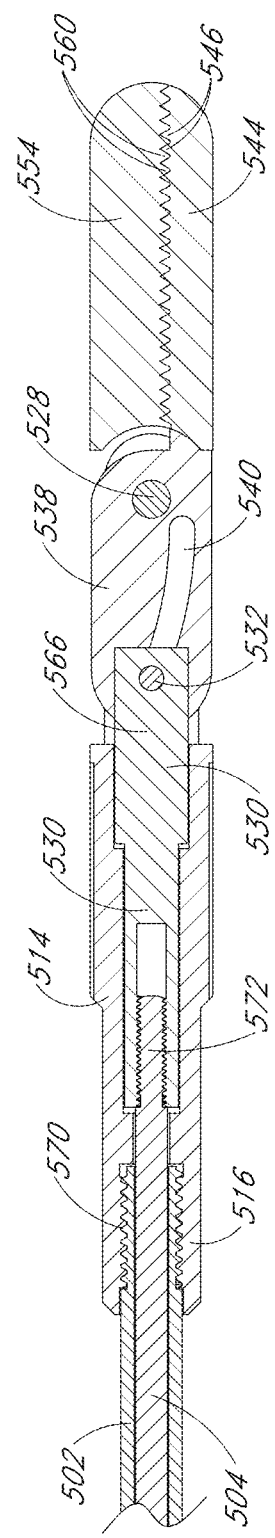
FIG. 5B illustrates a cross-section of the grasper tool shown in FIG. 5A taken along line 5B-5B.
Figure 5C:
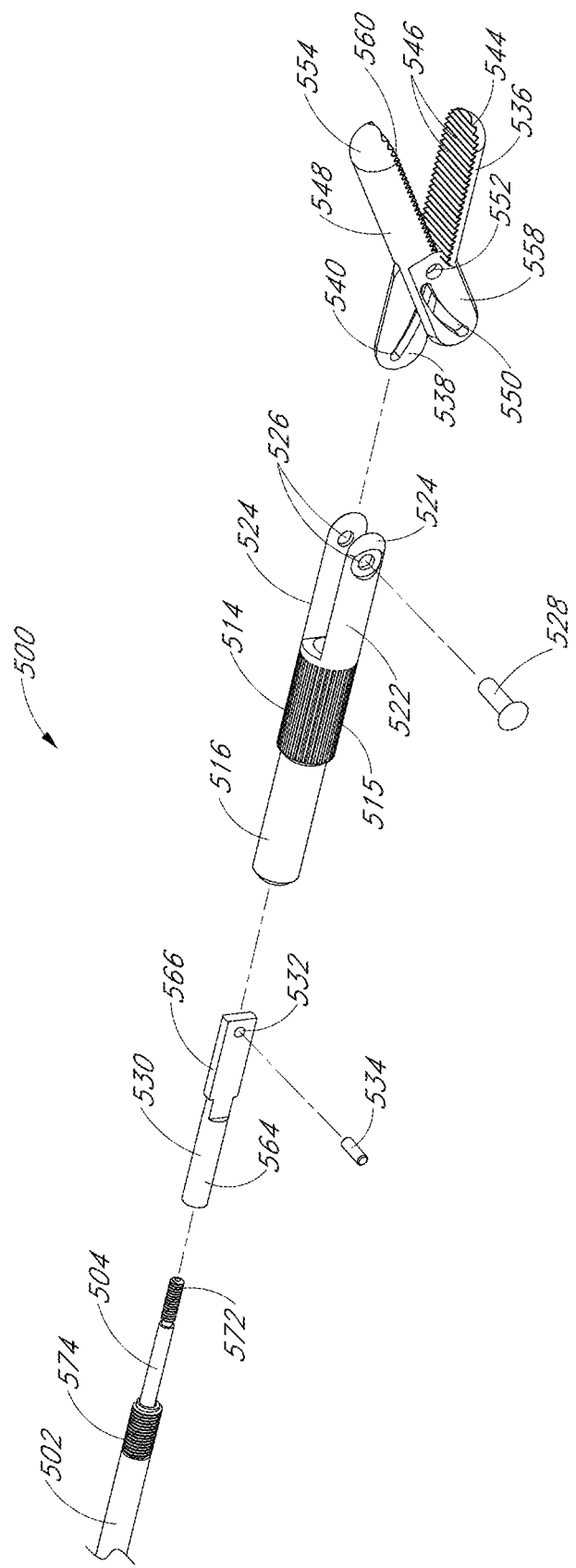
FIG. 5C illustrates an exploded view of the grasper tool shown in FIG. 5A.

FIGS. 5A-5C illustrate a grasper tool 500 configured to removably engage with a handle, such as the handle portion 102. The grasper tool 500 can include a number of components similar to the grasper tool 200 components, and the grasper tool 500 can be introduced into the patient using the methods described in connection with the grasper tool 200. In addition, the grasper tool 500 can be configured to open and close in a manner similar to grasper tool 200. Numerical references to similar components are the same as previously described, except that the references are in the 500s instead of the 200s.

The proximal portion 516 of the housing 514 can be removably coupled to the shaft portion 502. In some configurations, the shaft portion 502 can have a diameter of less than or equal to about 3.0 mm, preferably less than or equal to about 2.5 mm.

The grasper tool 500 can include a slide member 530 removably coupled to a push rod 504 and slidably disposed within a housing 514. A proximal portion 564 of the slide member 530 can define a lumen for receiving a distal portion of the push rod 504. Axial movement of the slide member 530 can cause a pin 534 to move along elongate slots 540, 550 to cause the jaw members 536, 548 to move between a closed configuration and an opened configuration.

Unlike the grasper tool 200, the grasper tool 500 can removably connect to the shaft portion 502 and the push rod 504 using one or more threaded regions. For example, as shown in FIGS. 5B and 5C, the shaft portion 502 can include a threaded region 570 along an outer surface of the distal portion of the shaft portion 502. The threaded region 570 can threadably engage an inner surface of a proximal portion 516 of the housing 514. In some instances, the push rod 504 can include a threaded region 572. The threaded region 572 can threadably engage an inner surface of a distal portion 564 of the slide member 530.

To assemble the grasper tool 500, the threaded portion 572 of the push rod 504 can be introduced into the lumen defined by the proximal portion 564 of the slide member 530, and the threaded region 570 of the shaft portion 502 can be introduced into the proximal portion 516 of the housing 514. Thereafter, the shaft portion 502 can be rotated to threadably engage the shaft portion 502 and the housing 514, and the push rod 504 can be rotated to threadably engage the push rod 504 and the slide member 564. In some instances, if the grasper tool 500 is secured to handle portion 102, the user can rotate the push rod 504 by rotating the proximal end 146 of the proximal handle portion 116. In some instances, the user can rotate the push rod 504 after threadably engaging the shaft portion 502 and the housing 514.

Figure 6C:
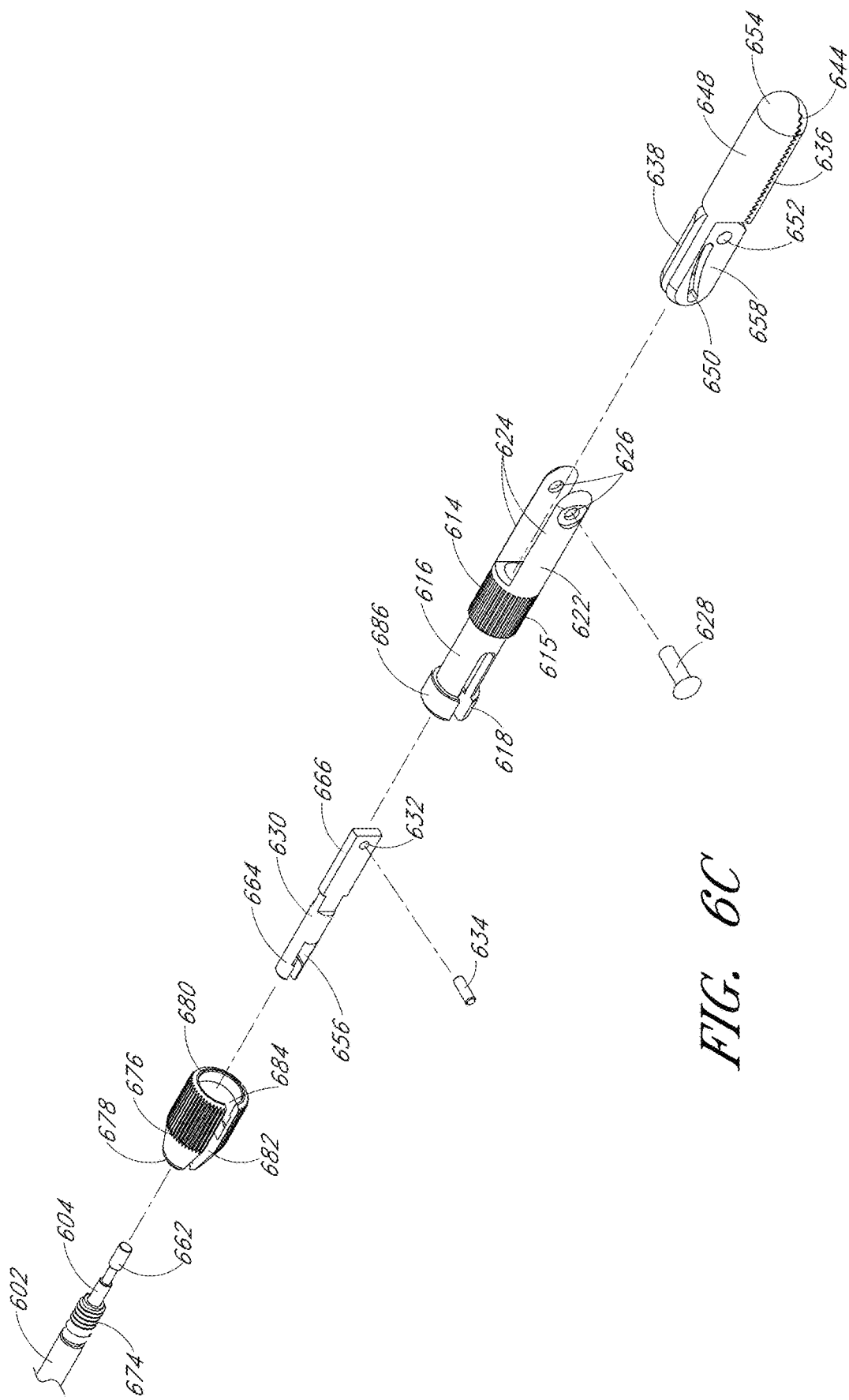
FIG. 6C illustrates an exploded view of the grasper tool shown in FIG. 6A.

FIGS. 6A-6C illustrate a grasper tool 600 configured to removably engage with a handle, such as the handle portion 102. The grasper tool 600 can include a number of components similar to the grasper tool 200 components, and the grasper tool 600 can be introduced into the patient using the methods described in connection with the grasper tool 200. In addition, the grasper tool 600 can be configured to open and close in a manner similar to grasper tool 200. Numerical references to similar components are the same as previously described, except that the references are in the 600s instead of the 200s.

The grasper tool 600 can include a slide member 630 removably coupled to a push rod 604 and slidably disposed within a housing 614. A proximal portion 664 of the slide member 630 can define a receiving portion 656 for receiving a distal portion 662 of the push rod 604. The receiving portion 656 can be configured to receive the distal portion 662 of the push rod 604 from a lateral direction.

The distal portion 662 of the push rod and the receiving portion 656 of the slide member 630 can be configured such that axial movement of the push rod 604 can move the slide member 630 in an axial direction. Axial movement of the slide member 630 can cause a pin 634 to move along elongate slots 640, 650 to cause the jaw members 636, 648 to move between a closed configuration and an opened configuration.

The grasper tool 600 can include a nut 670 having a proximal end 678 and a distal end 680. The proximal end 678 of the nut 676 can define a lumen for receiving the shaft portion 602. For example, an outer surface of the distal end of the shaft portion 602 can include a threaded region 674 configured to threadably engage an inner surface of the proximal end 678 of the nut 676. In some instances, an outer surface of the proximal end 678 of the nut 676 can be tapered.

The distal end 680 of the nut 676 can be configured to engage a proximal portion 616 of the housing 614. For example, the distal end 680 of the nut 676 can include a recessed portion 684 configured to receive an outwardly projecting portion 686 of the housing 614. The nut 676 can include a lengthwise slit 682 configured to permit the nut to be clipped over the outwardly projecting portion 686 of the housing.

To assemble the grasper tool 600, the distal end 662 of the push rod 604 can be introduced into the receiving portions 618, 656 from a lateral direction. Thereafter, the nut 676 can be clipped over the projection portion 686 and the shaft portion 602 can be rotated to threadably engage the proximal end 678 of the nut 676.

FIGS. 7A-7C illustrate a grasper tool 700 configured to removably engage with a handle, such as the handle portion 102. The grasper tool 700 can include a number of components similar to the grasper tool 200 components, and the grasper tool 700 can be configured to open and close in a manner similar to grasper tool 200. Numerical references to similar components are the same as previously described, except that the references are in the 700s instead of the 200s.

The grasper tool 700 can include a slide member 730 removably coupled to a push rod 704 and slidably disposed within a housing 714. A proximal portion 764 of the slide member 730 can define a receiving portion 756 for receiving a distal portion 762 of the push rod 704. The receiving portion 756 can be configured to receive the distal end 762 of the push rod 704 from a lateral direction.

The distal portion 762 of the push rod and the receiving portion 756 of the slide member 730 can be configured such that axial movement of the push rod 704 can move the slide member 730 in an axial direction. Axial movement of the slide member 730 can cause a pin 734 to move along elongate slots 740, 750 to cause the jaw members 736, 748 to move between a closed configuration and an opened configuration.

The proximal portion 716 of the housing 714 can define a lumen configured to engage a distal end of the shaft portion 702. For example, an outer surface of the distal end of the shaft portion 702 can include a threaded region 774 configured to threadably engage an inner surface of the proximal portion 716 of the housing 714.

To assemble the grasper tool 700, the distal end 762 of the push rod 704 can be introduced into the receiving portions 718, 756 from a lateral direction. Thereafter, the shaft portion 702 can be rotated to threadably engage the proximal portion 716 of the housing 714.

Figure 8C:
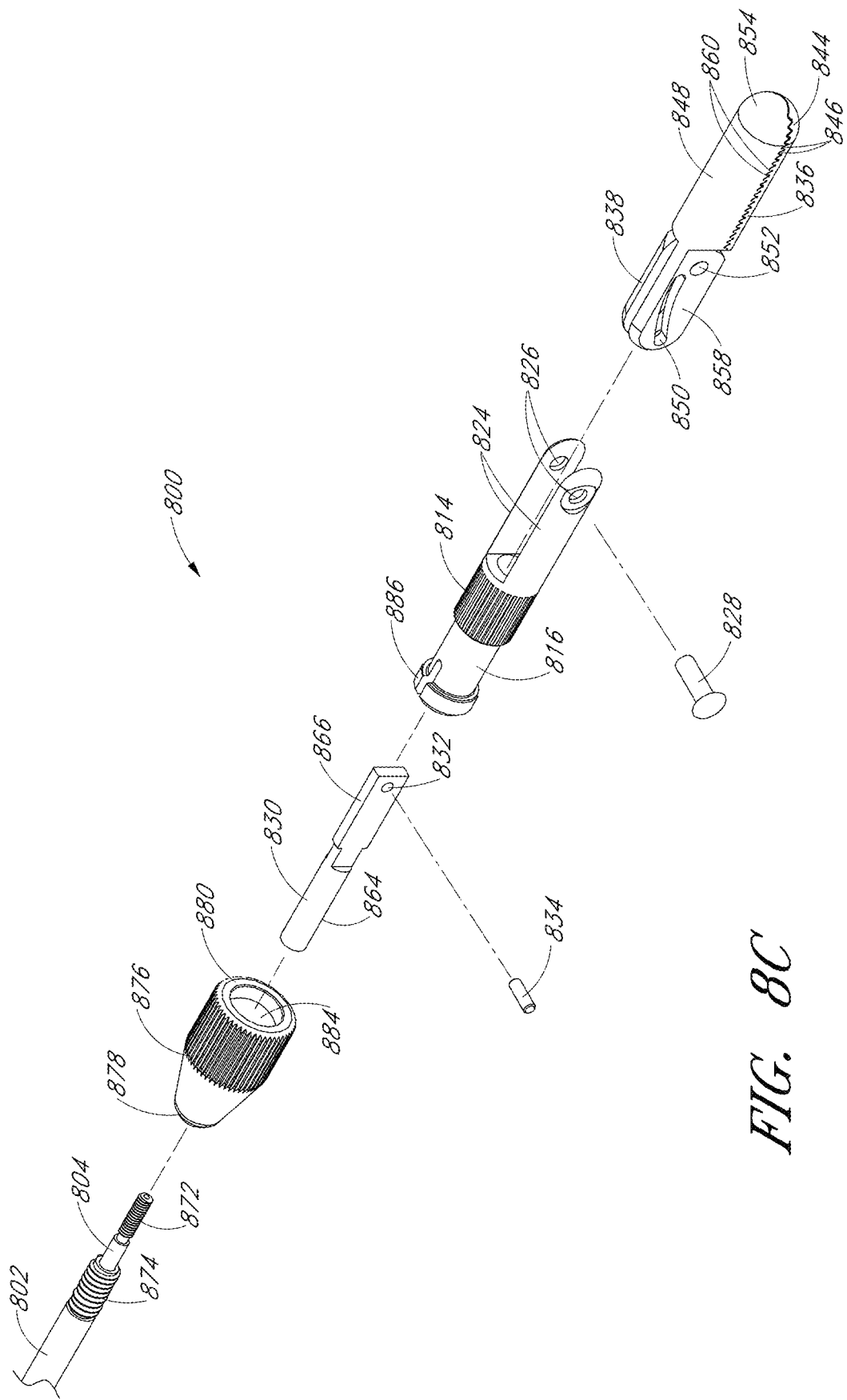
FIG. 8C illustrates an exploded view of the grasper tool shown in FIG. 8A.

FIGS. 8A-8C illustrate a grasper tool 800 configured to removably engage with a handle, such as the handle portion 102. The grasper tool 800 can include a number of components similar to the grasper tool 200, 500, 600 components, and the grasper tool 800 can be introduced into the patient using the methods described in connection with the grasper tool 200. In addition, the grasper tool 800 can be configured to open and close in a manner similar to grasper tool 200. Numerical references to similar components are the same as previously described, except that the references are in the 800s instead of the 200s, 500s, and/or 600s.

The grasper tool 800 can removably connect to the shaft portion 802 and push rod 804 using one or more threaded regions. Similar to grasper tool 500, the push rod 804 can include a threaded region 872 configured to threadably engage an inner surface of a distal portion 864 of the slide member 830.

The grasper tool 800 can include a nut 870 having a proximal end 878 and a distal end 880. The proximal end 878 of the nut 876 can define a lumen for receiving the shaft portion 802. For example, an outer surface of the distal end of the shaft portion 802 can include a threaded region 874 configured to threadably engage an inner surface of the proximal end 878 of the nut 876. In some instances, an outer surface of the proximal end 878 of the nut 876 can be tapered.

The distal end 880 of the nut 876 can be configured to engage a proximal portion 816 of the housing 814. For example, the distal end 880 of the nut 876 can include a recessed portion 884 configured to receive an outwardly projecting portion 886 of the housing 814.

To assemble the grasper tool 800, the threaded portion 872 of the push rod 804 can be introduced into the lumen defined by the proximal portion 864 of the slide member 830. With the nut 876 secured to the projecting portion 886, the threaded portion 874 of the shaft portion 802 can be introduced into the proximal portion 878. Thereafter, the shaft portion 802 can be rotated to threadably engage the shaft portion 802 and the nut 876, and the push rod 804 can be rotated to threadably engage the push rod 804 and the slide member 864. In some instances, if the grasper tool 800 is secured to handle portion 102, the user can rotate the push rod 804 by rotating the proximal end 146 of the proximal handle portion 116. In some instances, the user can rotate the push rod 804 after threadably engaging the shaft portion 802 and the housing 814.

Although the above-mentioned grasper tool embodiments 200, 500, 600, 700, 800 describe different connection features, one or more of the connection features from any of the grasper tool embodiments 200, 500, 600, 700, 800 can be combined with each other. In addition, any of the working ends (e.g., graspers, dissectors, scissors, needle driver, insertion tip, or otherwise) discussed herein, can be used with any combination of the connection features.

Clip Holder

FIGS. 9A-9E illustrate a clip holder 900 configured to retain one or more clips or staples. Smooth metal clips or non-absorbable polymer clips such as Hem-o-lok® clips or any other absorbable or non-absorbable material could potentially be utilized in this clip holder. The clip holder 900 can be positioned within the abdomen for ready access when clips 910 are necessary, especially during a vessel rupture or when required to control a vessel or to reposition a peritoneal covering.

Various clip and staple designs having a first leg and a second leg can be used with the clip holder, including, but not limited to the Hem-o-lok®, LIGACLIP®, LAPRA- TY®, or Hemoclip®. For example, as shown in FIG. 9D, the clip 910 can include a first leg 918 connected to a second leg 922. Each of the legs 918, 922 can be generally curved. The first leg 918 can include a hooked ending 920 configured to engage an end 924 of the second leg 922 when the clip 910 is applied to a vessel.

The clip holder 900 can include a shaft portion 902 and a cartridge 904. The shaft portion 902 and the cartridge 904 can be integrally formed or removably secured with each other, for example, using any of the connection mechanisms described herein. In some configurations, the shaft portion 902 can include a diameter of less than or equal to about 3.0 mm, preferably less than or equal to about 2.5 mm, having a threaded region to threadably engage the cartridge 904. The distal portion of the threaded region can be configured to create significant friction to prevent turning of the cartridge 904 while attempting to load the clip applier internally.

In some configurations, the cartridge 904 can hold clips 910 having varying shapes and sizes. For example, larger clips can be centrally positioned, while smaller clips can be placed near the tapered ends of the cartridge. With this configuration, the surgeon only needs one cartridge 904 per surgery, and the surgeon can select the cartridge that best fits his predicted needs.

The cartridge 904 can have a diameter D sized to receive a clip 910 and pass through an incision formed in the umbilicus. For example, the diameter D of the cartridge 904 can be at least about 8 mm and/or less than or equal to about 25 mm, preferably between about 10 mm and about 12 mm.

The cartridge can have a length L sized to receive a number of clips 910. The length L of the cartridge 904 can be at least about 1 cm and/or less than or equal to about 15 cm. For example, the clip applier can be about 3 cm long and hold 10-15 10 mm and six 5 mm clips. In another configuration, the clip cartridge 904 can be 5 cm long and hold 15-25 10 mm clips and 10 5 mm clips. In another configuration, the cartridge can be 15 cm long and hold 6-10 15 mm clips, 10-20 10 mm clips, and 10-20 5 mm clips.

The cartridge 904 can include a generally cylindrical body having rounded proximal and distal ends 906, 914. The cartridge 904 can include one or more openings 908 configured to receive the one or more clips 910. As shown in FIG. 9E, the one or more openings 908 can include a shape generally similar to the shape of the clips 910. The openings can be configured such that the clips 910 can be inserted from a top portion of the cartridge 904. In order to reduce the weight of the clip holder 900, the cartridge can include a number of openings formed within the central wall portions 930 of the cartridge 904.

Each clip 916 can rest on a support structure 926 within each opening 908. The support structures 926 and openings 908 can be configured to allow partial deflection of the clips 916 toward the closed configuration. For example, the support structure 926 can be shaped to permit the clip legs 918, 922 to move toward the support structure 926 without securing the clip ends 920, 924 to each other. In some instances, the openings 908 permit the clips 910 to deflect at least about 20 degrees and/or less than or equal to about 30 degrees. In another configuration, the deflection could be at least 10 degrees and/or less than or equal to about 20 degrees. In another configuration this deflection could be at least about 30 degrees and/or less than or equal to about 40 degrees.

The clip holder can include one or more side inserts 912 configured to retain the clips 910, preferably two side inserts 912. The side inserts 912 can be integrally or separately formed with the cartridge 904. If the slide inserts 912 and the cartridge 904 are separately formed, the sidewalls of the cartridge 904 can include one or more slits configured to receive the side inserts 912. Each slide insert 912 can include a portion extending into each opening 908 and/or a groove or other opening configured to receive the clip 910. In some instances, the clips 910 can be biased to an opened configuration and press against the side inserts 912.

The clip holder cartridge 904 can be disposable or reusable. To load the cartridge, a clip applier can be used to grab a clip 910 and move the clip 910 partially toward the closed configuration. In this partially closed configuration, the clip 910 can be inserted into a clip opening 912. Once the clip 910 is released from the clip applier tool, the clip 910 can rest on the support structure 926 and open until the legs 918, 922 push against the side insert. The clip applier can include jaw members such as those shown in FIG. 2G.

To remove the clip 910, the clip applier can be used to grab a clip 910 and move the clip partially toward the closed configuration. In this partially closed configuration, the clip 910 can be removed from the clip opening 912 and deployed in the patient anatomy as desired.

Suction Tools

Figure 10:
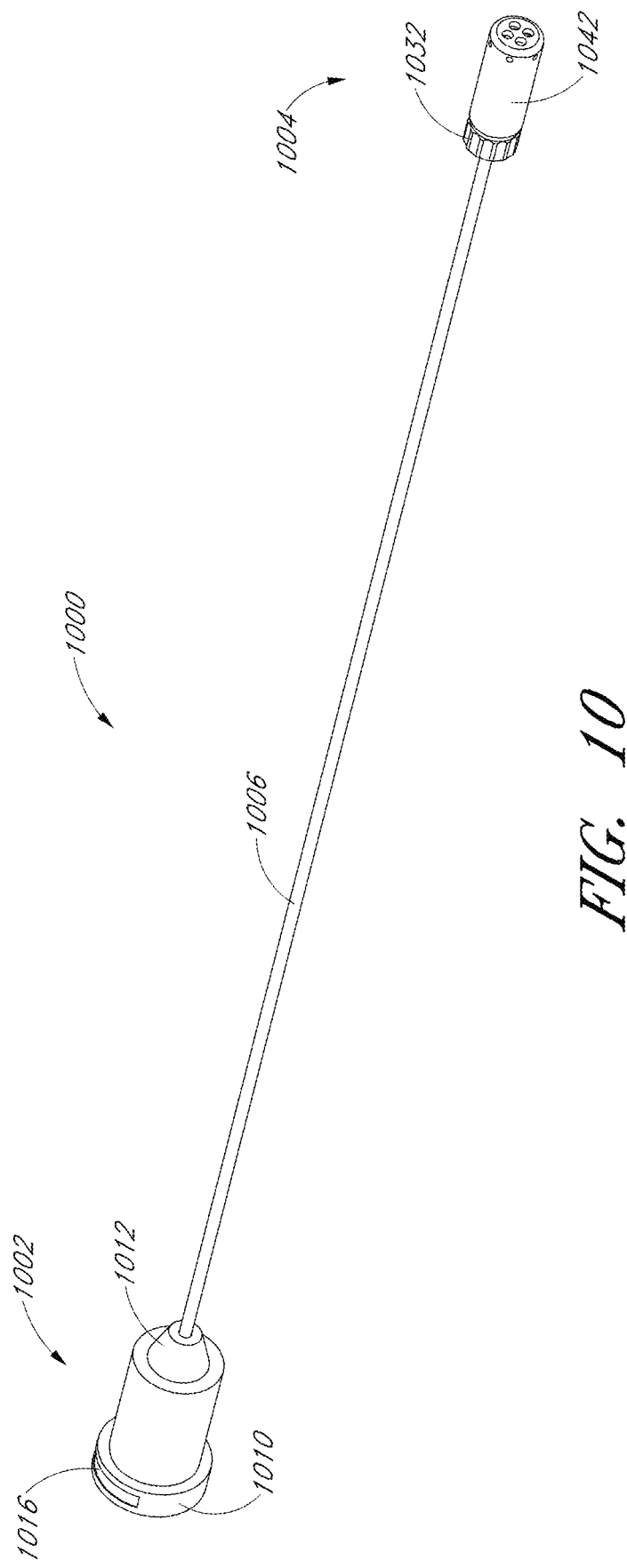
FIG. 10 illustrates a perspective view of a suction tool.
Figures 11A, 11B:
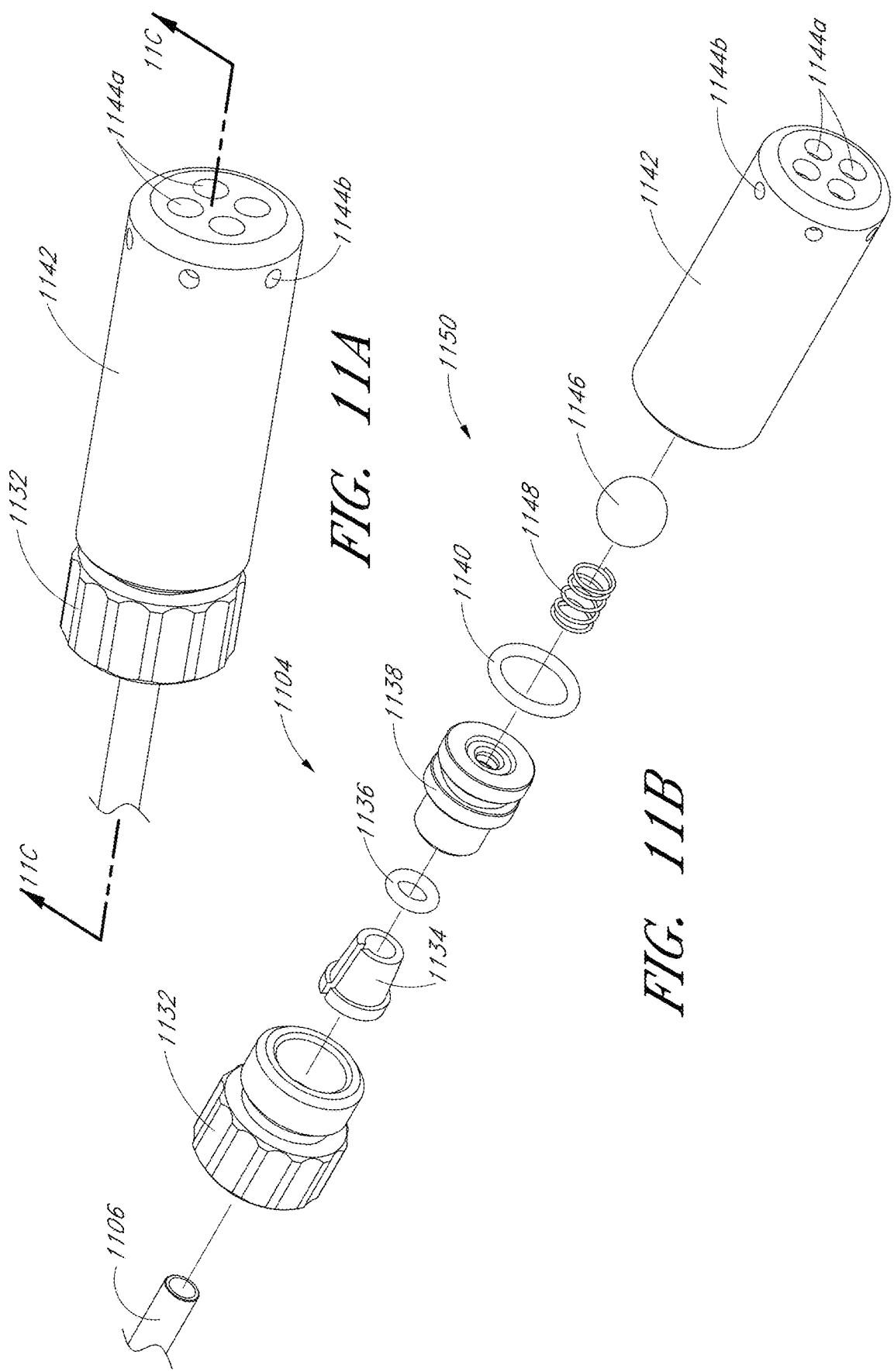
FIG. 11A illustrates a perspective view of a suction end.
FIG. 11B illustrates an exploded view of the suction end shown in FIG. 11A.

FIG. 10 illustrates a suction tool 1000 having a suction connector 1002, a suction end 1004, and a suction shaft 1006 extending from the suction connector 1002 to the suction end 1004. The suction connector 1002 can removably secure the suction tool 1000 to a source of suction. For example, the suction connector 1002 can define a cavity for receiving a distal portion of the suction source, and a clip 1016 can secure the suction tool 1000 to the suction source. Various clip designs are described in connection with FIGS. 13A-13J.

In some instances, the surgical tool 1000 can include a ferrule configured to facilitate a friction fit between the suction connector 1002 and the source of suction. The ferrule (not shown) can be secured to the suction connector 1002 (e.g., by welding, gluing, or otherwise) or be integrally formed with the suction connector 1002.

The suction connector 1002 can include a proximal end 1010 and a distal end 1012. The proximal end 1010 can include an annular projecting portion and/or an outer surface of the distal end 1012 can include a tapered region. The distal end 1012 can be configured to receive at least a portion of the suction shaft 1006.

A distal portion of the suction shaft 1006 can connect to the suction end 1004. The suction shaft 1006 can include a diameter sized to increase the flow rate, while minimizing the appearance of scars. For example, the shaft can include a diameter of less than or equal to about 3 mm, preferably about 2.5 mm.

FIGS. 11A-11D illustrate various views of a suction end 1104. The suction end 1104 can include a suction tip 1142 configured to house one or more components of the suction end 1104. For example, the suction tip 1142 can be secured to the shaft 1106 using one or more of a fastener 1132, a ferrule 1134, an inner gasket 1136, a funnel 1138, and/or an outer gasket 1140.

The suction tip 1142 can have a length of at least about 1 cm and/or less than or equal to about 5 cm and a diameter of less than or equal to about 1 cm. In some configurations, the suction tip 1142 can include a number of apertures, including one or more apertures 1144a at a distal face of the suction tip 1142 and/or one or more apertures 1144b along a sidewall portion of the suction tip 1142. The apertures 1144a, 1144b can be spaced apart and sized to control flow. For instance, the suction tip 1142 can include six evenly spaced lateral apertures 1144b and/or four evenly spaced distal apertures 1144a. The distal apertures 1144a can have a larger diameter than the lateral apertures 1144b.

The apertures 1144a, 1144b and suction shaft 1006 can be configured to permit a flow rate of at least about 200 cc/minutes and/or less than or equal to about 1000 cc/min, for example, for example, between about 500 cc/min to about 1000 cc/min or between about 800 cc/min and about 1000 cc/min.

As shown in FIGS. 11C-11D, the ferrule 1134 can be disposed along a distal portion of the shaft 1006, and the inner gasket 1136 can be disposed along the distal portion of the shaft 1006 and adjacent to a distal end of the ferrule 1134. The ferrule 1134 can be configured to facilitate a friction fit between the fastener 1132 and the suction shaft 1106 and/or between the funnel 1136 and the suction shaft 1106. In some instances, the ferrule 1134 can be similar to the ferrule 212 or the ferrule 212a. For example, the ferrule 1134 can be generally tapered in a distal direction.

The funnel 1138 can include a proximal portion and a distal portion. The proximal portion can be secured over at least a portion of the ferrule 1134 and the inner gasket 1136, while the outer gasket 1140 can secure a proximal portion of the funnel 1138 to the suction tip 1142. The distal portion of the funnel 1138 can define a lumen sized to receive a distal end of the suction shaft 1106. In some configurations, the distal face of the funnel 1138 can include a recessed portion for receiving a proximal end of a valve.

The fastener 1132 can include a proximal portion and a distal portion. The proximal portion of the fastener 1132 can remain external to the suction tip 1142. In some configurations, a proximal end of the fastener 1132 and/or a proximal end of the suction tip 1142 can include a number of chamfer cuts to facilitate a connection between the different components. The distal portion of the fastener 1132 can define a cavity configured to receive at least a portion of the ferrule 1134 and/or the funnel 1138. As shown in FIGS. 11C-11D, the distal portion of the fastener 1132 can be disposed between the suction tip 1142 and the proximal portion of the funnel.

During surgery, when the suction source is turned off, fluid stored in the shaft 1106 can often flow back out of the suction tip 1142. In these scenarios, it can be difficult to discern whether the outflow of fluid is from the suction tool 1100 or a vessel rupture. Accordingly, it can be desirable to incorporate a check valve into the suction end 1104. For example, as shown in FIGS. 11C-11D, it can be desirable to include a ball check valve 1150 having a spring 1148 and a ball 1146. As shown in FIG. 11C, when fluid is not flowing proximally, the spring 1148 biases the ball 1146 to a closed configuration such that fluid cannot flow distally out of the suction tip 1142. When a source of suction is turned on and fluid moves proximally through the suction end 1104, the fluid pushes the ball proximally to compress the spring, so fluid can flow past the valve 1150.

FIGS. 12A-12D illustrate a suction end 1204 similar to the suction end 1104. Numerical references to similar components are the same as previously described, except that the references are in the 1200s instead of the 1100s.

The suction end 1204 extends distally from a distal end of a suction shaft 1206. In some configurations, the suction shaft 1206 can have a diameter of less than or equal to about 3.0 mm, preferably less than or equal to about 2.5 mm. A distal portion of the suction shaft 1206 can include a threaded region 1258 configured to threadably engage the fastener 1232. In some configurations at least a portion of the fastener 1232, can include a threaded region 1206 configured to threadably engage the suction tip 1242.

The suction tip 1242 can include a number of apertures 1244a, 1244b that can take on various configurations. For example, the suction tip 1242 can include an aperture configuration similar to the suction tip 1142. In some configurations, the suction tip 1242 can include between about four and nine apertures 1244a and/or between about six and fifteen apertures 1244b depending on the desired flow rate. As shown in FIG. 12B, the suction tip 1242 can include a center aperture 1244a surrounded by four evenly spaced apertures 1244a. In some instances, the suction tip can include a number of indentations 1246.

Figure 12C:
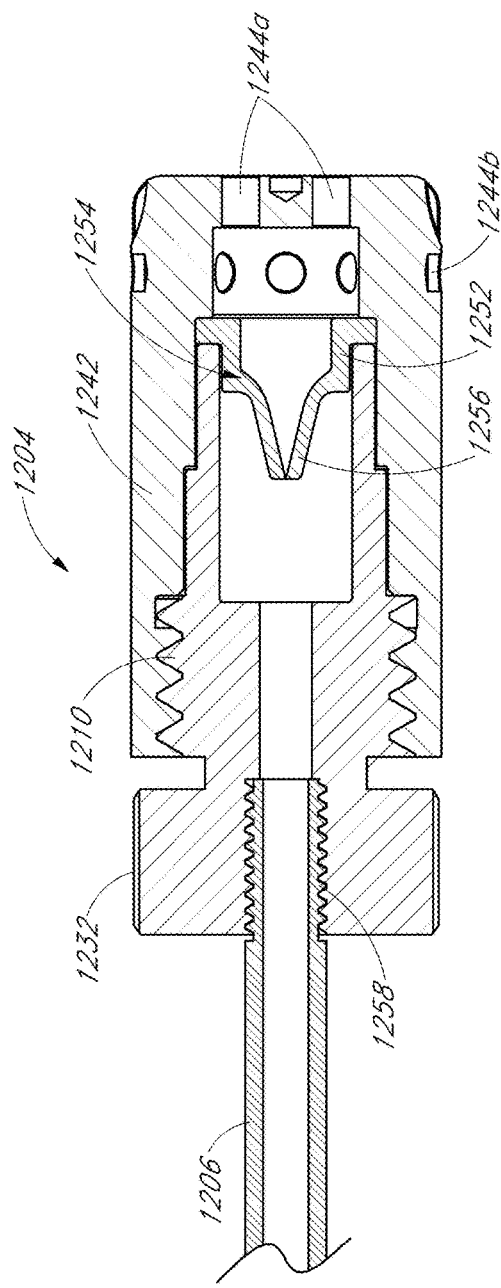
FIG. 12C illustrates a cross-section of the suction end shown in FIG. 12A taken along line 12C-12C in a closed configuration.
Figure 12D:
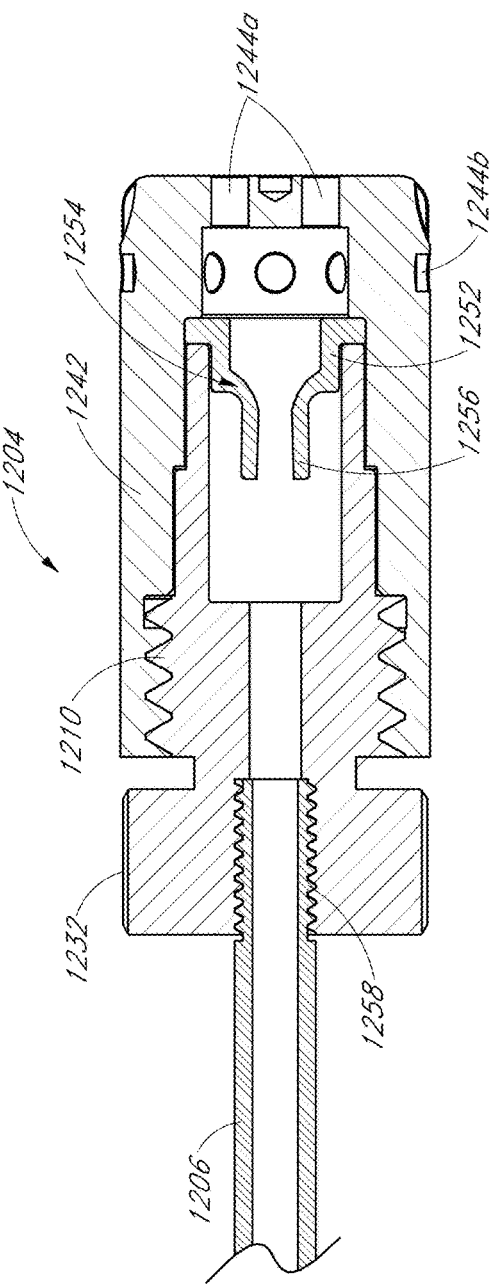
FIG. 12D illustrates a cross-section of the suction end shown in FIG. 12A taken along line 12D-12D in an opened configuration.

As discussed above, it can be desirable to include a one-way valve to prevent an outflow of fluid through the suction tool and out of the suction end 1204. As shown in FIGS. 12C-12D, the one-way valve can be a duckbill valve 1254 having a proximal portion 1256 and a distal portion 1252. The proximal portion 1256 of the valve 1254 can be disposed within a cavity defined by the distal portion of the fastener 1232, and/or the distal portion 1232 can include an outwardly projecting annular rim 1252 positioned between the distal end of the fastener 1232 and a distal face of the suction tip 1242. The duckbill valve 1254 can be configured to prevent the outflow of fluid from the suction end 1204, but permit the proximal flow of fluid when the source of suction is turned on.

Although the above-mentioned suction end embodiments 1104, 1204 describe different features, one or more of the features from either of the suction end embodiments 1104, 1204 can be combined with each other.

FIGS. 13A-13J illustrate various clips that can be used to secure the suction connector to the suction source and/or to secure the suction end to the suction shaft, in addition to or in alternative to the use of the fastener described above. These clip mechanisms can also be used with any of the surgical tools described herein to add an additional level of safety to ensure that the tips of these instruments do not fall off inside the patient. Although both configurations are possible, the clips will be discussed in connection with connecting the suction end to the suction shaft. Any of the clips described herein can be used alone or in connection with the fastener 1132 and/or or threaded portion 1258 described above.

Figures 13A, 13B:
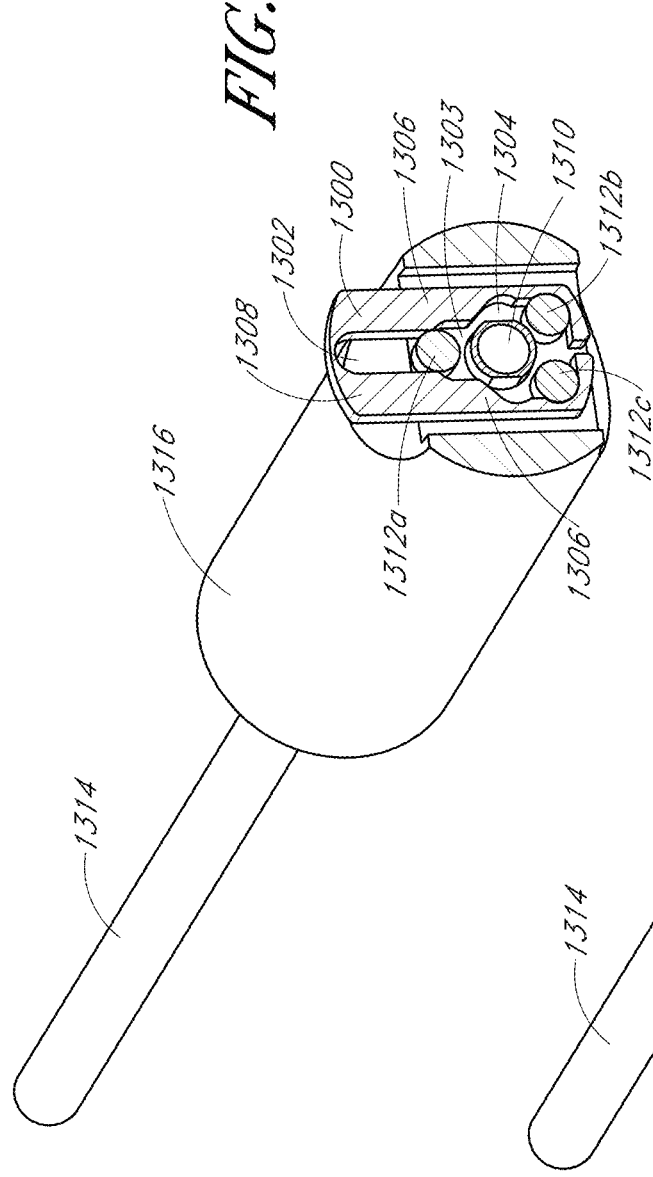
FIG. 13A illustrates a perspective view of a surgical tool having a locking clip to ensure that the tip does not fall off inside the patient in an opened configuration.
FIG. 13B illustrates the surgical tool shown in FIG. 13A in a closed configuration.

As shown in FIGS. 13A and 13B, the suction end 1316 can include a number of rods, for example, three rods, 1312a, 1312b, 1312c extending through the suction end. The clip 1300 can be positioned to secure the suction shaft 1314 to the rods 1312a, 1312b, 1312c, and thus the suction end 1316. The clip 1300 can be positioned generally transverse to a longitudinal axis of the suction source 1314.

As shown in FIGS. 13A-13B, the clip 1300 can include two leg portions 1306 defining a cavity having a first opening portion 1302, a second opening portion 1303, and/or a third opening portion 1304. The first opening portion 1302 can have an elongated shape with a width generally corresponding to a diameter of the rod 1312a to prevent the suction end 1306 from falling off. In some instances, the width can be less than or equal to about 1 cm, or less than or equal to about 0.5 cm. The second opening portion 1303 can be sized to receive a distal portion 1310 of the suction source 1314. The third opening portion 1304 can be larger than the first opening portion 1302 and can be sized to receive the distal portion 1310 of the suction source 1314 and at least two rods 1312b, 1312c. The clip 1300 can include a metal material that is sufficiently thick to provide a spring mechanism to lock the pins into place.

The clip 1300 can move from an opened configuration (FIG. 13A) to the closed configuration (FIG. 13B) by applying a downward force on an upper surface 1308 of the clip 1300. When the clip 1300 is in the opened configuration (FIG. 13A), at least a portion of 1312a is positioned within the second opening portion 1303, while the distal portion 1310 of the suction source 1314 and at least two rods 1312b, 1312c are positioned within the third opening portion 1304. In the closed configuration (FIG. 13B), at least a portion of the distal end 1310 of the suction source 1306 is positioned within the second opening portion 1303, while the at least two rods 1312b, 1312c are positioned in an upper portion of the third opening portion 1304.

Figure 13C:
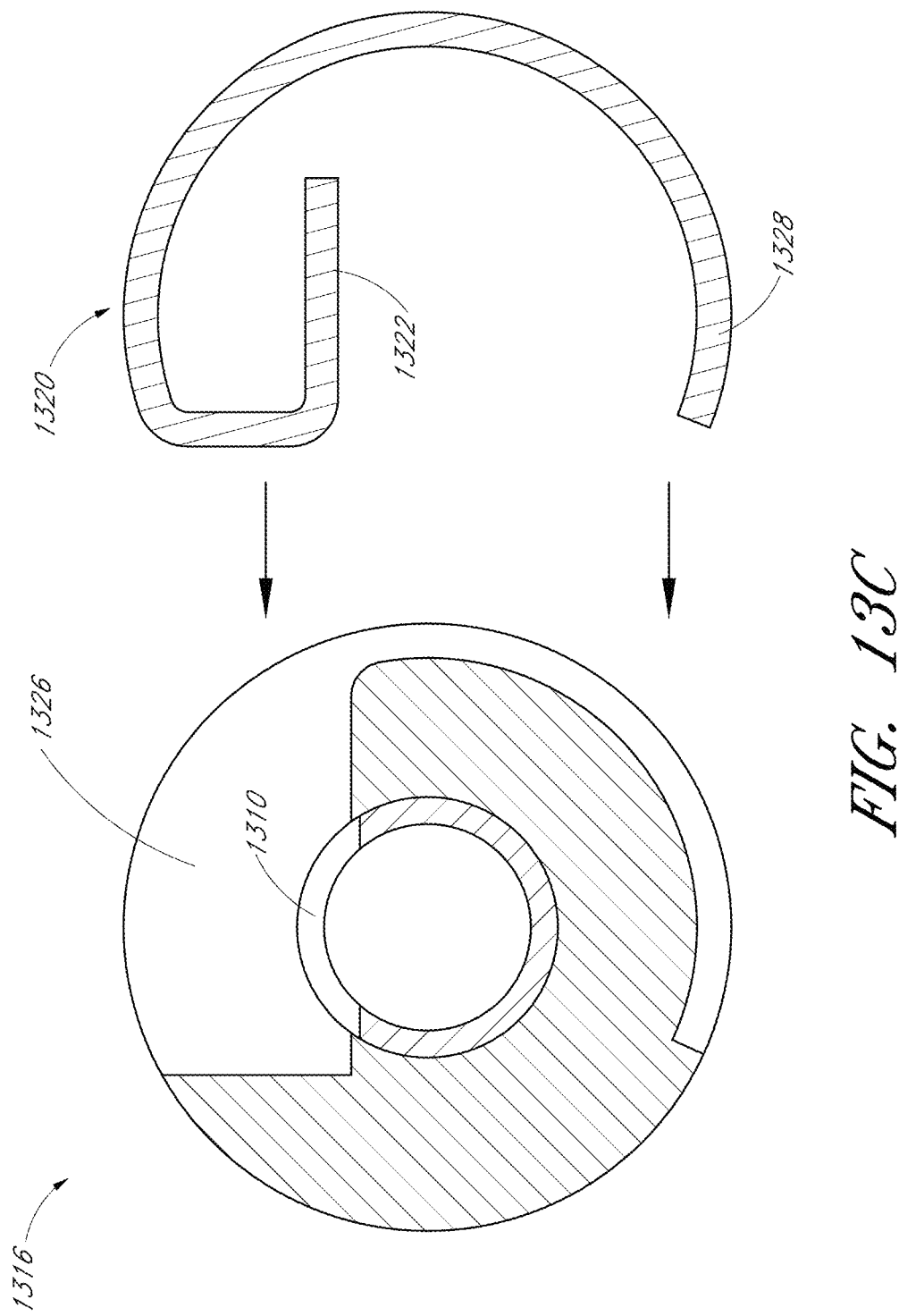
FIG. 13C illustrates a cross-section of a different locking clip mechanism to hold the interchangeable surgical tool heads in place in an opened configuration.
Figure 13D:
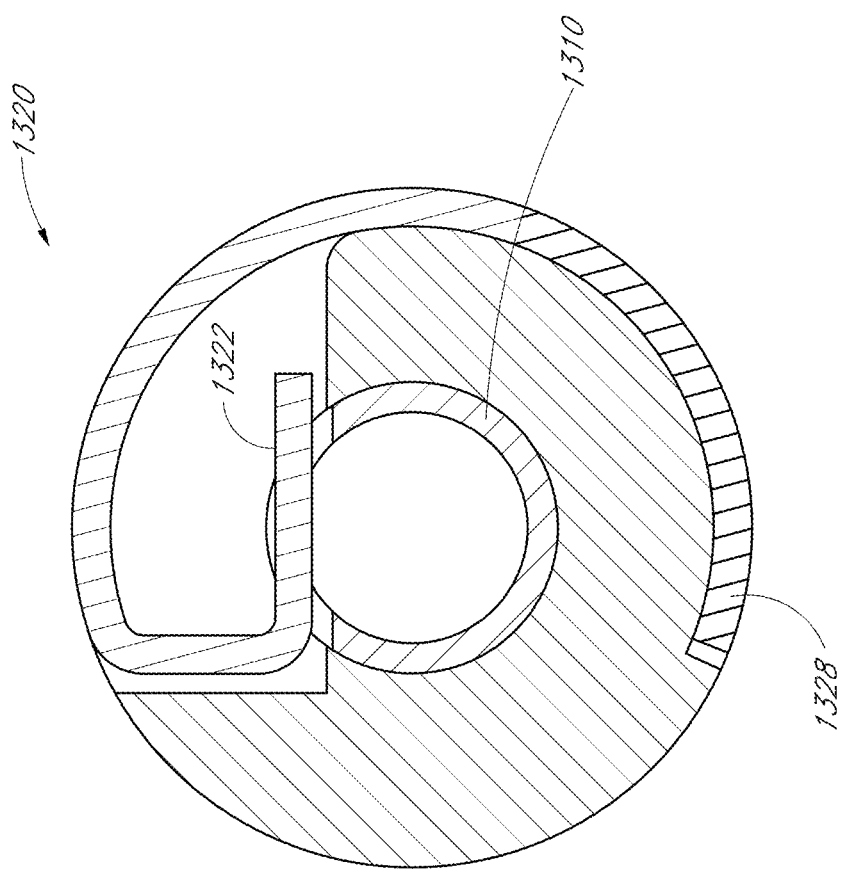
FIG. 13D illustrates the cross-section of the surgical tool and the c-clip shown in FIG. 13C in a closed configuration.

FIGS. 13C-13D illustrate a c-clip 1320 having a generally rounded configuration and capable of moving between an opened configuration (FIG. 13C) and a closed configuration (FIG. 13D). The c-clip can include a first rounded portion 1322 having a radius that is smaller than the radius formed by a second rounded portion 1328. The second rounded portion 1328 can be sized to receive at least the suction shaft 1310. The first rounded portion 1322 can have a diameter that is less than or equal to about half the diameter of the suction end 1316.

The suction end 1316 can include a recess 1326 configured to receive the clip 1320. As shown in FIG. 13D, when the c-clip 1320 enters the recess 1326, the clip 1320 can secure the suction end 1316 to the suction shaft 1310. For example, the c-clip 1320 can be biased inward to secure the suction shaft 1320 to the suction end 1316. In some instances, the suction shaft 1310 can either include a notched portion for receiving the first rounded portion 1322 or the suction shaft 1310 can be flexible.

Figure 13F:
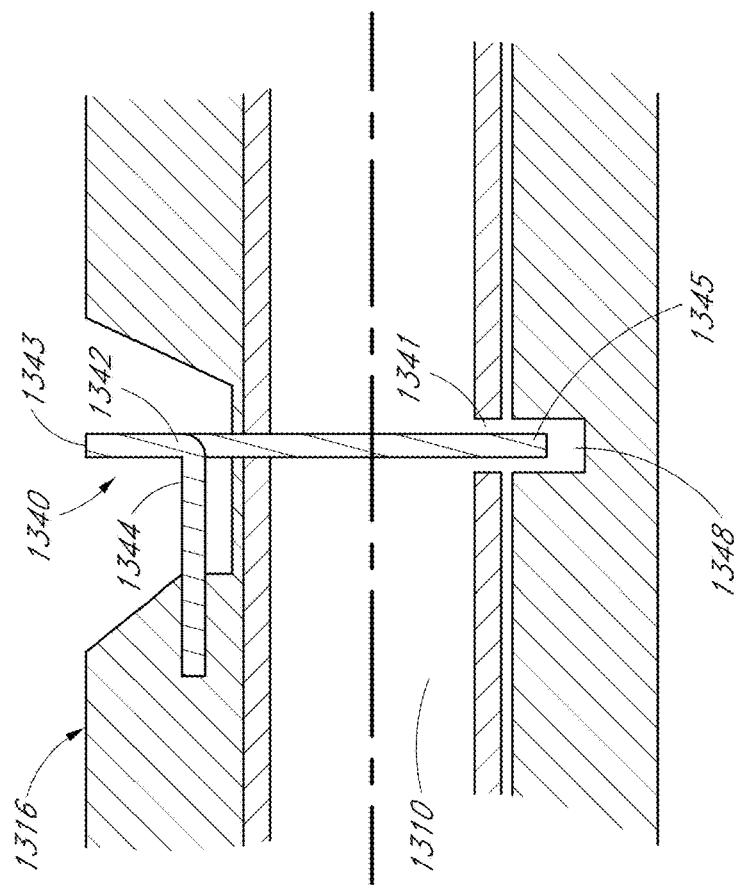
FIG. 13F illustrates a different cross-section of the surgical tool and the leaf spring clip shown in FIG. 13E.
Figure 13E:
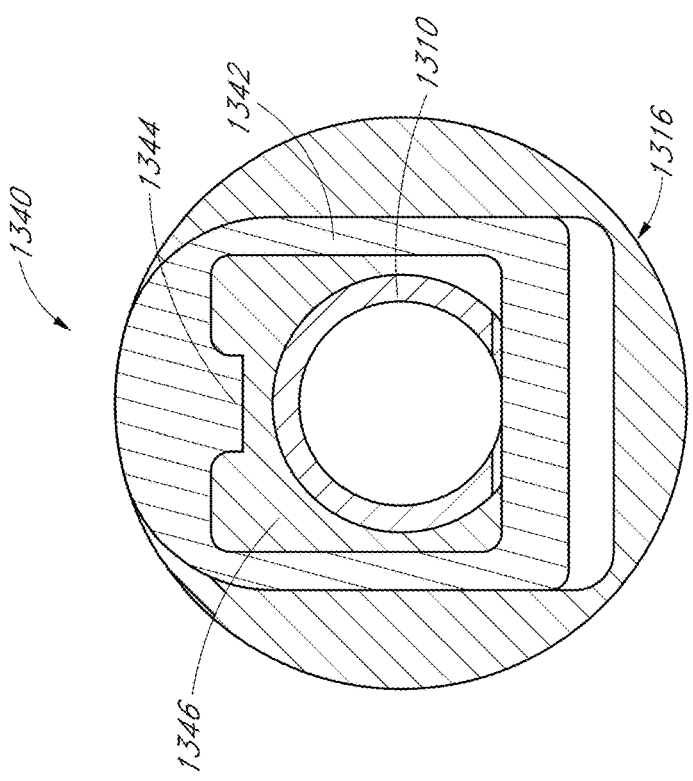
FIG. 13E illustrates a cross-section of a surgical tool and a leaf spring clip used to hold the interchangeable tool heads in place.

FIGS. 13E-13F illustrate a leaf spring 1340 for securing the suction end 1316 to the suction shaft 1310. The leap spring 1340 can include a body portion 1342 having an upper end 1343 and a lower end 1345. The body portion 1342 can define an opening 1346 through which the suction shaft 1310 extends. As shown in FIG. 13F, the leaf spring 1340 can include a projecting portion 1344 extending along an axis generally perpendicular to the body portion 1342 and secured to the suction end 1316. The projecting portion 1344 can remain fixed, while the body portion 1342 moves between an upper position (shown in FIGS. 13E-13F) and a lower position along an axis generally transverse to the longitudinal axis of the suction end 1316. In some instances, the leaf spring can be biased to the upper position.

The suction end 1316 can include a recess 1348 configured to receive the leaf spring 1340. Downward movement of the leaf spring 1340 into the recess portion 1348 permits the user to insert the suction shaft 1310 into the suction end 1316 or remove the shaft 1310 from the suction end 1316. After the suction shaft 1310 is introduced through the suction end 1316, the leaf spring 1340 can be released. Once released, the leaf spring 1340 can move back to the upper position to secure the suction shaft 1310 to the suction end 1346. In some instances, as shown in FIG. 13F, the suction shaft 1310 can include a notched portion 1341 or a region having a reduced diameter for receiving the lower end 1345 of the leaf spring 1340. In other examples, the suction shaft 1310 can be flexible.

Figure 13G:
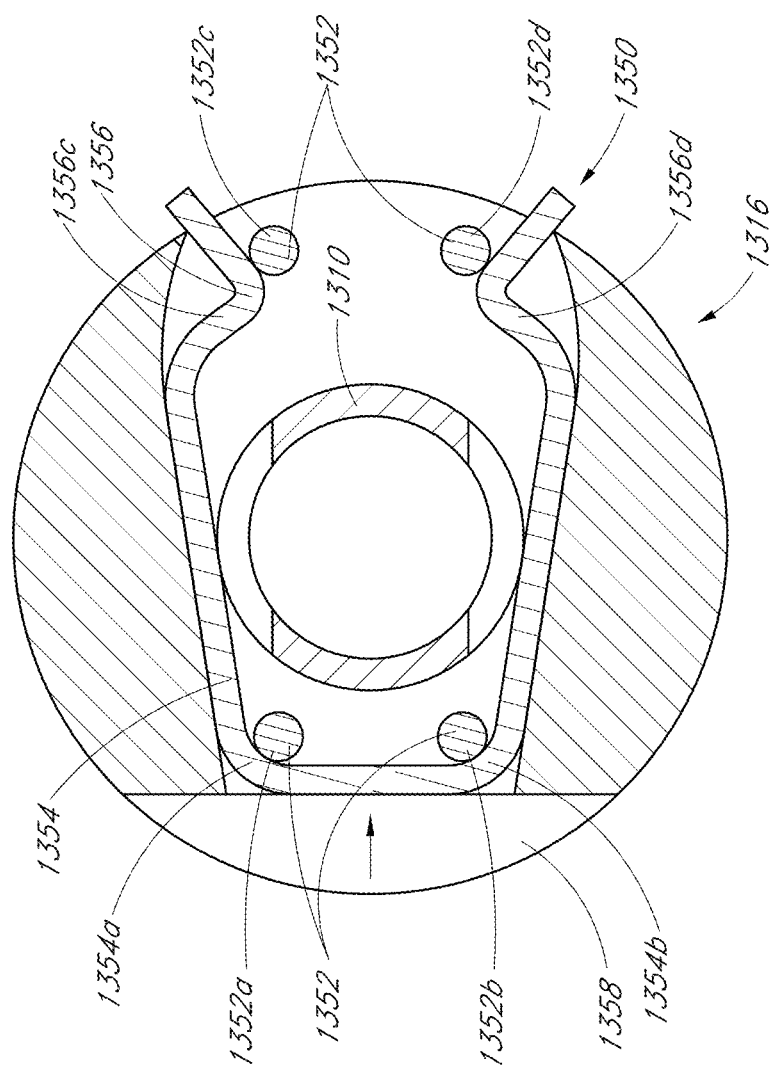
FIG. 13G illustrates a cross-section of a surgical tool and a wedge spread clip in an opened configuration.
Figure 13H:
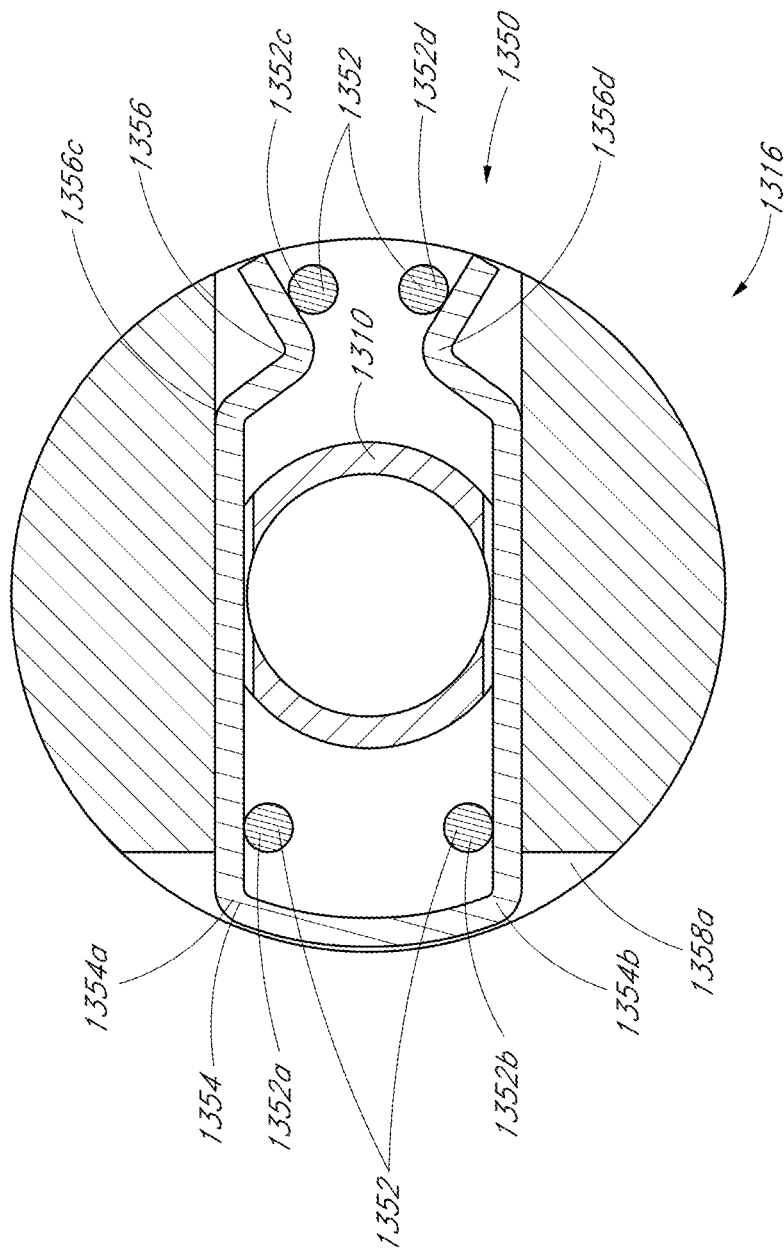
FIG. 13H illustrates a cross-section of the surgical tool and the wedge spread clip shown in FIG. 13G in a closed configuration.

FIGS. 13G and 13H illustrate a wedge spread 1350 for securing the suction end 1316 to the suction shaft 1310. The suction end 1316 can define a recessed portion 1358 for receiving the wedge spread 1350. The wedge spread 1350 is capable of moving within the recessed portion 1358, between an opened configuration (FIG. 13G) and a closed configuration (FIG. 13H). In some instances, the wedge spread 1350 can be biased toward the closed configuration.

As shown in FIGS. 13G and 13H, the suction 1316 can include a number of rods 1352, for example, four rods, to help secure the suction end 1316 to the suction shaft 1310. The rods 1352 can control the shape of the wedge spread 1350.

The wedge spread 1350 can include an upper body portion 1354 and a lower body portion 1356. The upper body portion 1354 can be sized to receive at least the suction shaft 1310. As shown in FIG. 13G, the upper body portion can include curved portions 1354a, 1354b configured to abut the rods 1352a, 1352b when the wedge spread 1350 is in the opened configuration. The rods 1352a, 1352b can limit movement of the wedge spread 1350 and The lower body portion 1356 can include curved portions 1356c, 1356d that curve inward toward the center of the wedge spread 1350 and contact rods 1352c, 1352d. As the wedge spread moves from the closed configuration (FIG. 13H) to the opened configuration (FIG. 13G), the rods 1352c, 1352b can cause the lower curved portions 1352c, 1352d to move apart and increase a width of the upper body portion 1354.

Downward movement of the wedge spread 1350 can move the wedge spread 1350 to the opened configuration. In the opened configuration, the suction shaft 1310 can be introduced into or removed from the suction end 1316. When the wedge spread 1350 is released back to the closed configuration, the upper body portion 1354 can have a width that is less than or equal to the width of the suction shaft 1310. The suction shaft 1310 can be flexible or can include notched portions for receiving the wedge spread 1350. In the closed configuration, the wedge spread 1350 can limit movement of the suction shaft 1310.

Figure 13I:
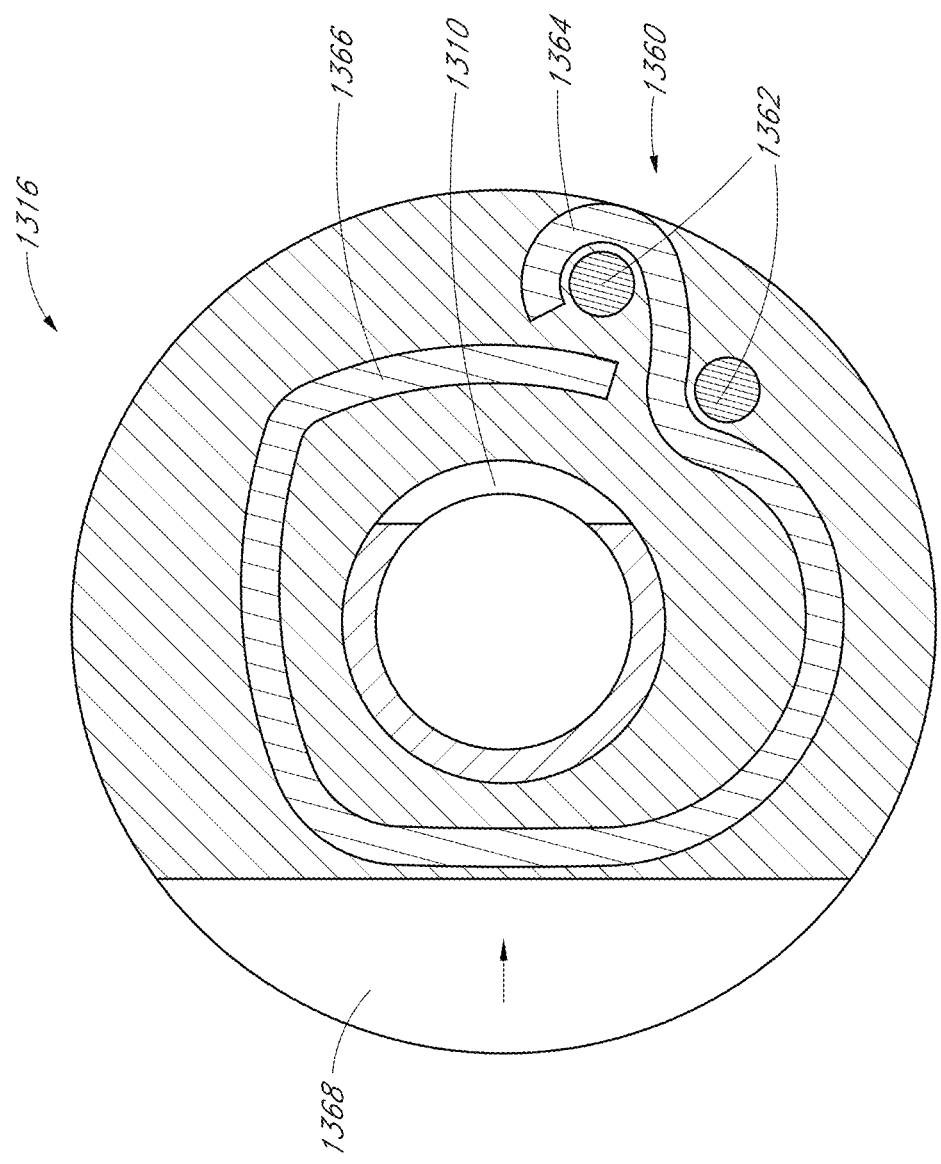
FIG. 13I illustrates a cross-section of a surgical tool and a G-clip in an opened configuration.
Figure 13J:
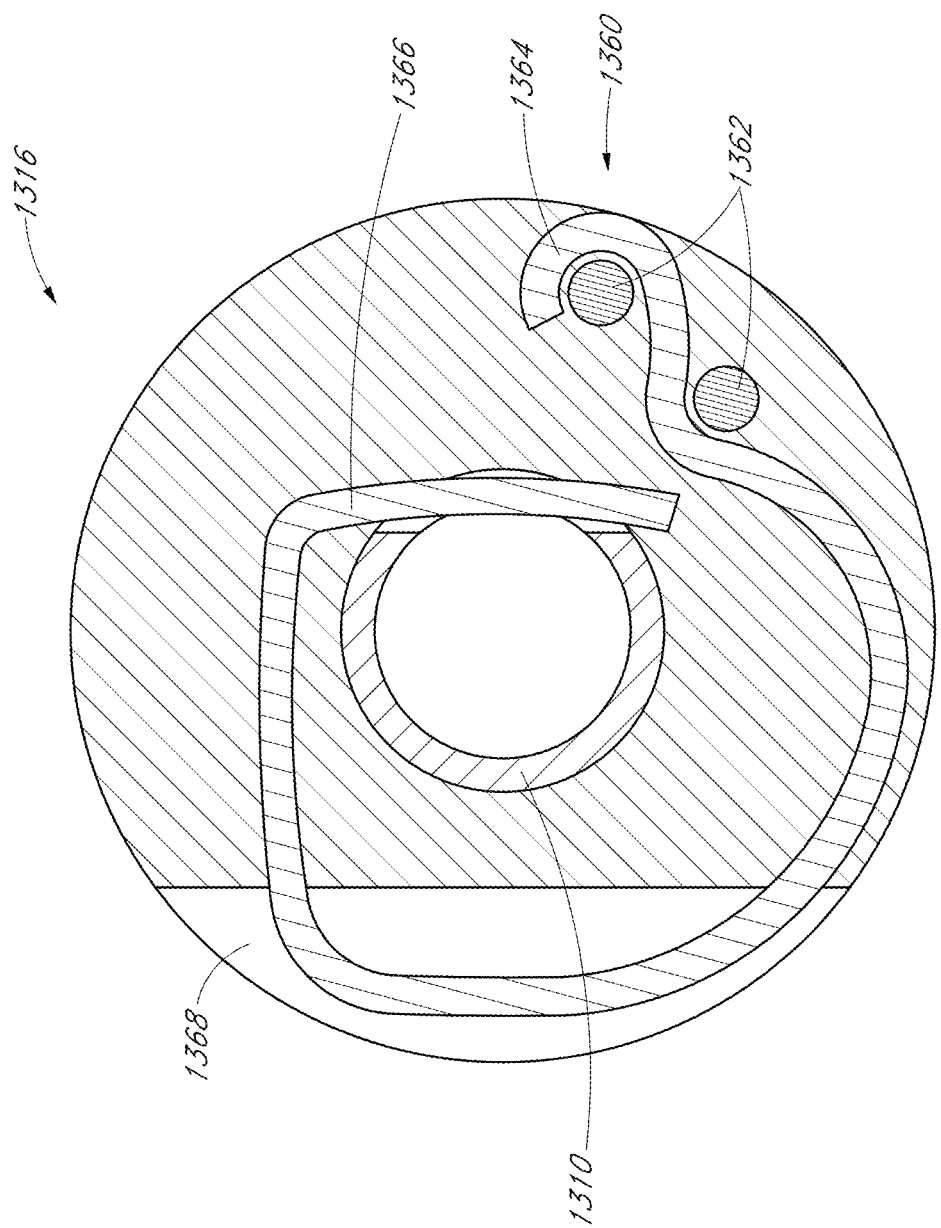
FIG. 13J illustrates a cross-section of the surgical tool and the G-clip shown in FIG. 13I in a closed configuration.

FIGS. 13I-13J illustrate a G-clip 1360 having a generally rounded configuration and capable of moving between an opened configuration (FIG. 13) and a closed configuration (FIG. 13J). The G-clip can include a first rounded portion 1364 having a radius that is smaller than the radius formed by a second rounded portion 1366. The first rounded portion 1364 can be configured to wrap around one or more rods 1362, for example, two rods, as shown in FIGS. 13I and 13J. The second rounded portion 1366 can be sized to receive at least the suction shaft 1310.

The suction end 1316 can include a recess 1368 configured to receive the clip 1360. As shown in FIG. 13D, when the G-clip 1360 enters the recess 1368, the clip 1360 can secure the suction end 1316 to the suction shaft 1310. The suction shaft 1310 can either include a notched portion for receiving the first rounded portion 1322 or the suction shaft can be flexible.

Figure 17:
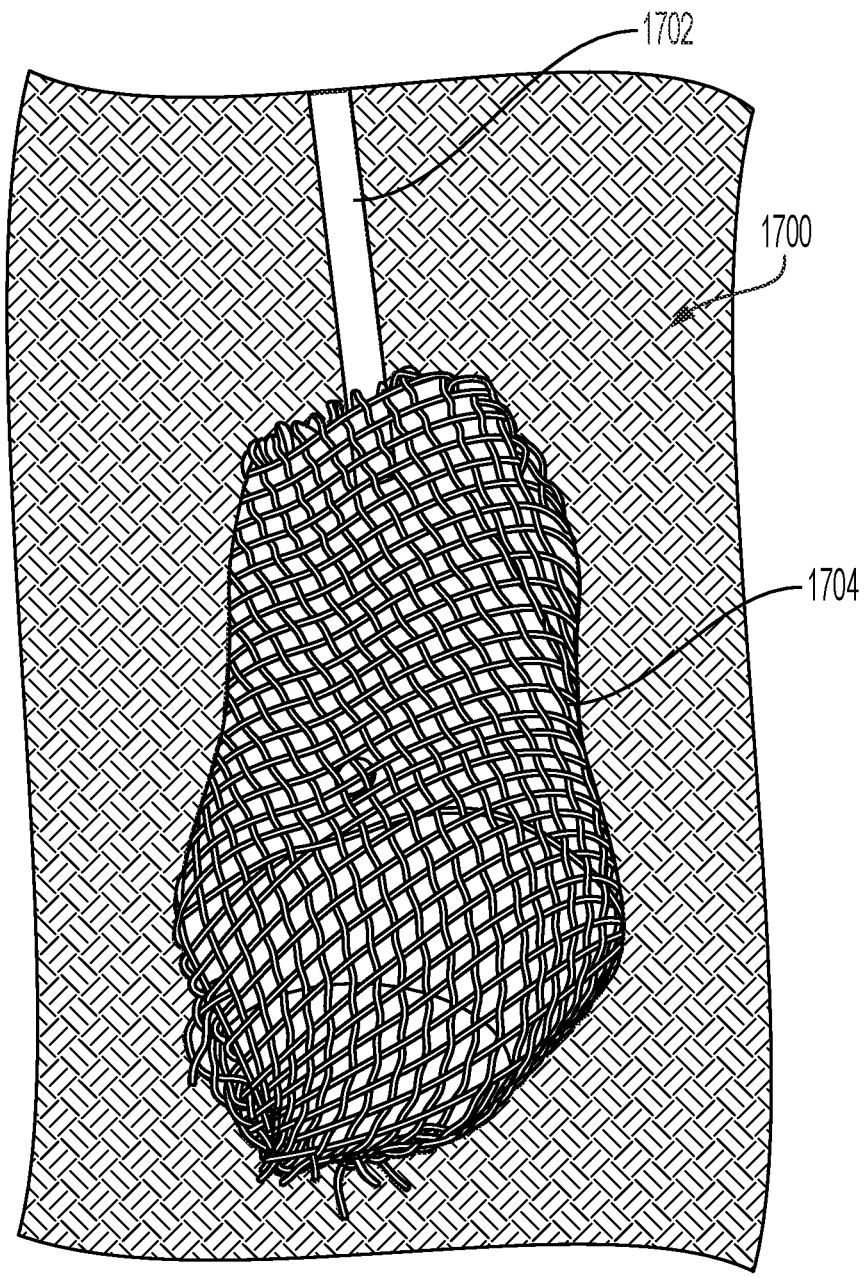
FIG. 17 illustrates a perspective view of a suction end having a diffusion tip, which prevents plugging of the suction device.

FIG. 17 illustrates a diffusion tip 1700 positioned over a suction end (e.g., 1104, 1204, or otherwise). The diffusion tip 1700 can be removably positioned over the suction end or permanently secured (e.g., welded, glued, etc.). The diffusion tip 1700 can include a fine mesh screen 1704 that is shaped to be atraumatic and rigid enough for controlled movement, both forward motion and retraction. For example, a suction tool having the diffusion tip 1700 can require at least about 5 lb. of force. The mesh can be constructed from a non-kinking material, such as nitinol.

The mesh pores can sufficiently large to permit the suction of fat without clogging the pores, while still being small enough to control flow rate. The mesh pores prevent clots from moving upstream through the shaft portion. Any clots small enough to pass through the mesh pores will be able to pass through the shaft portion. As mentioned above, the flow rate can be at least about 200 cc/min and/or less than or equal to about 1000 cc/min, preferably at least about 500 cc/min or at least about 800 cc/min.

Electrocautery Tools

FIGS. 14A-14E illustrate a surgical tool 1400 having a hook electrode assembly 1404 for performing electrocautery during minimally invasive surgery, for example, for cauterizing or cutting. The hook electrode assembly 1404 can mate with a distal end of a shaft portion 1402 using, for example, a simple threaded mechanism or using any of the connection features described herein. Similar to other devices described herein, the shaft portion 1402 can include a diameter of less than or equal to about 2.5 mm, and preferably about 2.3 mm.

The shaft portion 1402 can include a central core 1412 capable of conducting electrical charge. At least a portion of the central core 1412 can be surrounded by an insulation casing 1414.

A distal portion 1408 of the core 1412 may not be surrounded by the insulation casing 1414. The distal portion 1408 can be configured to mate with a recess portion 1444 within the body portion 1406. In some embodiments, the shaft material can include, but is not limited to, a metal, such as stainless steel, or a non-conducting polymer, such as carbon fiber or PTFE, to provide the shaft with sufficient stiffness.

The hook electrode assembly 1404 can include a body portion 1406 connected to an electrode 1426. The body portion 1406 can include a core 1430 capable of conducting an electrical charge from the core 1412 to the electrode 1426. The core 1430 can generally be surrounded by an insulation casing 1428. In some instances, the body portion 1604 can include a proximal section 1422 having a region of reduced diameter.

The electrode 1426 can include a material capable of conducting an electrical charge. The electrode 1426 can be integrally or separately formed from the body portion core 1430. As shown in FIGS. 14A-14E, the electrode 1426 can have a hook shape. For example, the distal end 1420 of the electrode 1426 can be positioned generally perpendicular to a central axis of the surgical tool 1400. In some configurations, the insulation casing 1428 can surround at least a portion of the electrode 1426.

Camera

Figure 15B:
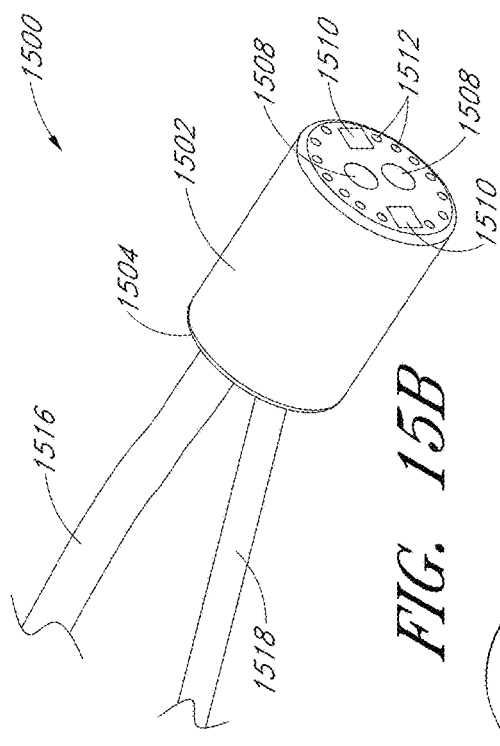
FIG. 15B illustrates a front perspective view of the camera shown in FIG. 15A and in a second configuration.
Figure 15E:
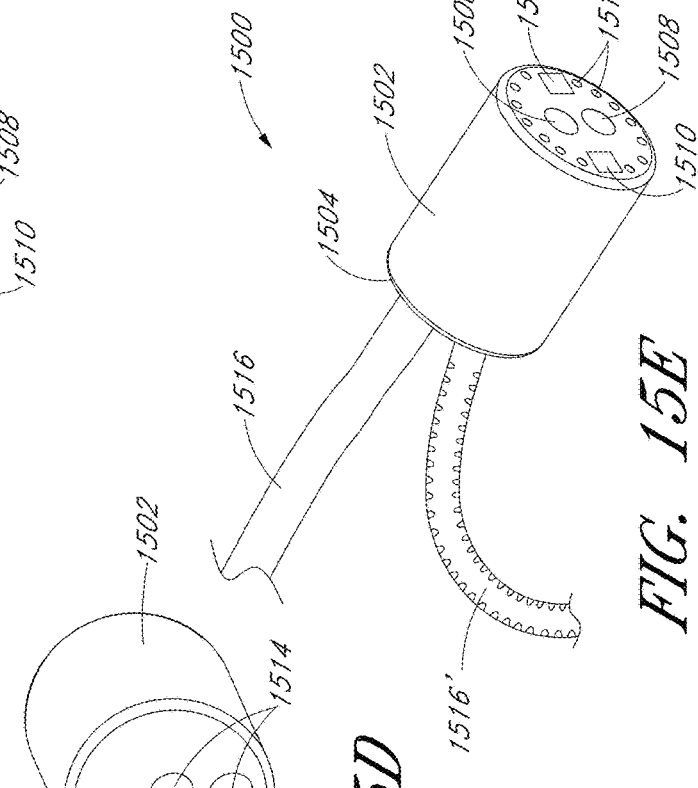
FIG. 15E illustrates the camera shown in FIG. 15A with flexible cords.
Figure 15D:
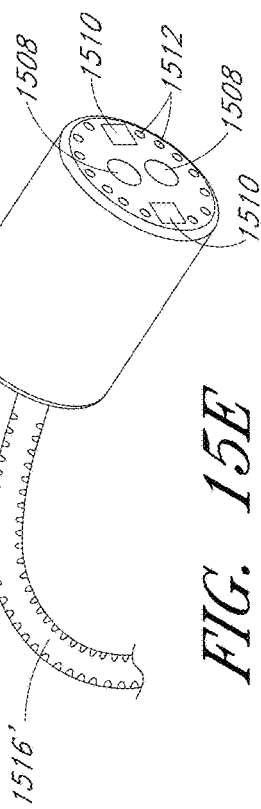
FIG. 15D illustrates a rear perspective view of the camera shown in FIG. 15A.
Figure 15A:
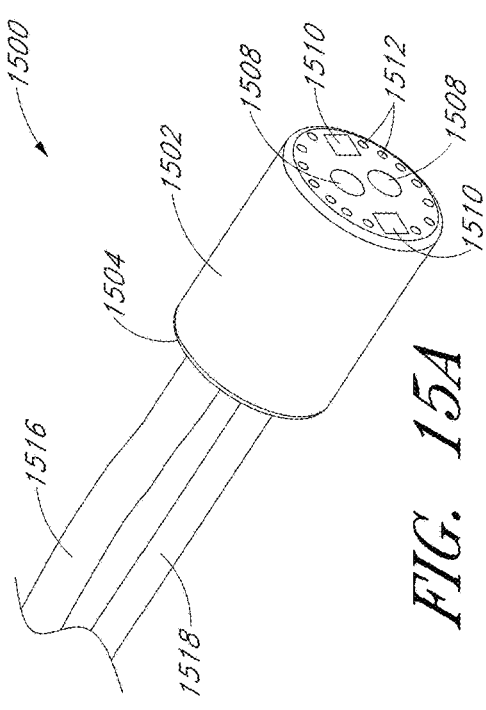
FIG. 15A illustrates a front perspective view of a camera in a first configuration.
Figure 15C:
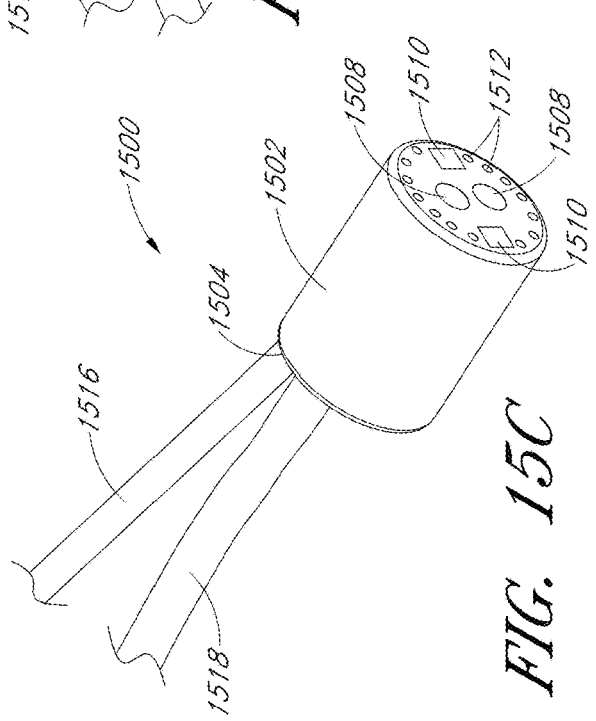
FIG. 15C illustrates a front perspective view of the camera shown in FIG. 15A and in a third configuration.

It can be desirable to insert a camera through one of the incisions, for example, through an incision positioned in the umbilicus region. The camera can be useful for visualizing the surgical procedure. FIGS. 15A-15B illustrate perspective views of a camera 1500 capable of insertion through an umbilicus opening. The camera 1500 can include a camera body 1502 connected to a flexible cord 1516 and/or a control rod 1508. During surgery, the flexible cord 1516 can extend through the umbilicus opening, while the control rod 1508 can extend through the umbilicus opening or any opening that will provide optimal visualization of the surgical site. In some instances, the control rod 1508 can have a diameter of less than or equal to about 3.0 mm, less than or equal to about 2.5 mm, or less than or equal to about 2.0 mm.

In general, the camera body 1502 can be generally cylindrical and include a proximal end 1504 and a distal end 1502. The camera body 1502 can be sized to be introduced through an opening in the umbilicus. For example, the camera body 1502 can have a length between about 1 cm and about 8 cm, and the camera body 1502 can include a diameter between about 1 cm and about 2.5 cm, preferably about 1 cm. One or more image sensors 1508 and/or lights 1510, 1512 can be disposed at the distal end 1506 of the camera body 1502. The images sensors 1508 can be sufficiently spaced apart to provide a better three-dimensional image than current robotic or laparoscopic devices, while still capable of being introduced through an incision that will not affect the cosmesis.

The one or more image sensors 1508 can include CMOS or CCD chips. In some configurations, the camera 1500 can include two image sensors 1508 positioned along the distal end 1506 of the camera body 1502. In order to improve three-dimensional visualization of the target anatomy, the image sensors 1508 can be positioned as far apart from each other as possible. For example, as shown in FIG. 15A, one CCD chip 1508 can be positioned at one distal edge of the camera body 1502 and the other CCD chip 1508 can be positioned at the opposite distal edge.

The one or more lights 1510, 1512 can include, for example, an LED 1512 and/or a xenon fiber optic light 1510. Various light configurations can be used. For example, the lights 1510, 1512 can be disposed at a center of the distal end 1506 of the camera body 1502 and/or surround a periphery of the distal end 1506 of the camera body 1502. In other configurations, a number of lights 1510, 1512 can surround each image sensor 1508.

As shown in FIG. 15A, the camera 1500 can include two xenon fiber optic lights 1510 centrally located at the distal end 1506 of the camera body 1502. In some instances, the xenon lights 1510 are disposed along an axis generally perpendicular to the axis along which the image sensors 1508 are positioned. The back end of the camera 1500 can include a plug for mating with the xenon fiber optic light source.

In some instances, the camera 1500 can include one or more LEDs 1512. As shown in FIG. 15A, a number of LEDs 1512, for example, eight LEDs 1512, can be disposed along a periphery of the distal end 1506 of the camera body 1502. In some scenarios, the LEDs can emit the same color. Alternatively, different subsets of LEDs 1512 can emit different colors, including, but not limited to, white, warm white, cool white, red, green, and blue. Utilizing different colored LEDs 1512 can help accent different anatomical features. For instance, when targeting a certain anatomy, the surgeon can activate one subset of the LEDs emitting a first color, and when targeting another anatomy, the surgeon can activate a different subset of LEDs emitting a second color.

The flexible cord 1516 can extend from the proximal end 1504 of the camera body 1502 and surround the connections between the camera body 1502 and a power source. In some instances, the flexible cord 1516 can surround the connection between the image sensors 1508 and a three-dimensional camera plug-in. The three-dimensional camera plug-in can connect to a three-dimensional viewing screen worn by the surgeon. In some instances, the flexible cord 1516 can surround the connections between the lights 1510, 1512 and their respective light sources. As shown in FIG. 15E, the camera 1500 can include multiple flexible cords 1516, 1516'.

The camera body 1502 can removably connect to the control rod 1518. For example, the camera body 1512 can define one or more shaft lumens 1514 configured to receive the control rod 1518. In some instances, the camera body 1502 can threadably engage the control rod 1518. Although not shown, in some configurations, the control rod can permit flexible angulation of the camera. For example, the control rod 1518 can be flexible (e.g., mechanically-actuated, formed from a rigid material with slits, formed from a flexible material, or otherwise). If the control rod 1518 is mechanically actuated, the control rod 1518 can include an actuation member, such as a pull wire configured to bend the control rod 1518.

Due to the positioning of certain anatomical features, such as the kidneys, relative to the umbilicus, it can be difficult to maneuver existing camera devices to visualize those anatomical features. To help maintain the correct angle of the camera body 1502, each lumen 1514a, 1514b, 1514c can be positioned at a different angle such that the control rod 1518 can maintain the camera body 1502 at a specific angle. For example, as shown in FIG. 15B, the camera body 1502 can include a first lumen 1514a substantially collinear with the camera body. A second lumen 1514b can be disposed at a 30 degree upward angle, and a third lumen 1514c can be disposed at a 30 degree downward angle. The lumens 1514a, 1514b, 1514c can be disposed at other angles and/or the camera body 1502 can include additional lumens.

Ports

A standard port, as shown in FIG. 16A, generally has a fixed length. However, as mentioned above, the thickness of the abdominal wall can vary between about 1 mm and about 20 cm. Accordingly, it can be desirable to have a single port capable of adjusting to the thickness of a particular patient's abdominal wall. In addition, it can be desirable to adjust the length of the port to maximize the usable length of the surgical tool. The usable length of the tool is only as long as the portion of the tool extending past an inner edge of the port when the port is introduced into the patient. As such, a longer than necessary port can shorten the usable length of the surgical tool and disrupt the surgical tool's range of motion.

FIG. 16C illustrates an adjustable port 1600 and an adjustment tool 1602 configured to adjust a length of the port 1600 between a minimum length and a maximum length. In some instances, the length of the adjustable port 1600 can vary between about 4 cm to about 7 cm. In some instances, the length of the adjustable port 1500 can vary between about 4 cm and about 14 cm.

The adjustable port 1600 can include an inner member 1622 slidably disposed within the outer member 1604. The outer member 1604 can include a generally tubular structure having a length substantially equal to a minimum length of the adjustable port. The minimum length can be less than or equal to about 8 cm, or less than or equal to about 4 cm.

The outer member 1604 can also include a first end 1606 and a second end 1608. The first end 1606 can include an outwardly projecting annular rim 1610 that can be either rigid or flexible. During the procedure, the rim 1610 can be positioned external to the patient and against the abdominal wall, as shown in FIGS. 16H-16J.

In some instances, an inner surface of the outer member 1602 can include a threaded region 1612. The threaded region 1612 can extend along a majority of a length of the outer member 1602, along substantially the entire length of the outer member 1602, or along the entire length of the outer member 1602.

The inner member 1622 can be generally tubular and include a first end 1614 and a second end 1616. The first end 1614 can include a number of mating features 1632 (e.g., projections, nubs, grooves, openings, or otherwise) configured to engage the adjustment tool 1602.

The length of the inner member 1622 can be less than or equal to about the length of the outer member 1604 and depend on the desired maximum length of the adjustable port 1600. For example, the maximum length can be less than or equal to about the length of the outer member plus the length of the inner member. The maximum length can be between about 7 and about 14 cm.

In some instances, at least a portion of an outer surface of the inner member 1622 can include a threaded region 1618 configured to threadably engage the threaded region 1612 of the outer member 1604. For example, the threaded region 1618 can be positioned near the first end 1614. In other examples, the threaded region 1618 can extend along a majority of a length of the inner member 1622, along substantially the entire length of the inner member 1622, or along the entire length of the inner member 1622.

FIG. 16C illustrates an adjustment tool 1602. The adjustment tool 1602 can be generally tubular and include a first end 1624 and a second end 1626. The first end 1624 can include an outwardly extending annular rim 1628. The diameter of the rim 1628 can be larger than an inner diameter of the outer member 1604, such that the first end 1624 of the tool 1602 does not extend into a lumen defined by the outer member 1604. The outer diameter and inner diameter of the remaining portion of the tool 1602 can generally correspond to the outer and inner diameters of the inner member 1622.

The second end 1626 can include a number of attachment features 1629 (e.g., projections, nubs, grooves, openings, or otherwise) corresponding to the mating features 1632 of the inner member 1622. In some instances, the adjustment tool can include a gap 1630 extending along a length of the tool 1602.

FIGS. 16H-16J illustrate the port 1600 having different lengths depending on the thickness of the abdominal wall 1634. As shown in FIG. 16H, the first and second ends of the inner member 1614, 1616 are generally aligned with the first and second ends of the outer member 1606, 1608 such that the port is at its minimum length. For a thicker abdominal wall 1634 such as those shown in FIGS. 16I and 16J, the adjustment tool 1602 can be used to adjust the maximum length shown in FIG. 16J. In some instances, the port 1600 can be lengthened until a proximal end of the inner member threaded region 1618 reaches the distal end of the threaded region 1612.

As shown in FIGS. 16E-16G, the adjustment tool 1602 can be used to rotate the inner member 1622 relative to the outer member 1604 to adjust the length of the port 1600. The adjustment tool 1602 can be used to both decrease and increase the length of the port 1600. For example, the attachment features 1629 of the adjustment tool 1602 can mate with the mating features 1632 of the inner member 1604 such that rotation of the adjustment tool 1602 can rotate the inner member 1622 relative to the outer member 1604. Once the port 1600 is at a desirable length, the adjustment tool 1602 can be removed and the surgical tools can be introduced through the port.

In some configurations, a face plate 1636 can engage an annular rim 1628 of the adjustable port. The face plate 1636 can be configured to prevent the escape of fluids (e.g., insufflation gas) from the abdomen when surgical tools are introduced through the port 1600. For example, the plate 1636 can include a number of flexible flaps 1638 capable of forming a seal around a surgical tool extending through the port 1600. In some instances, the plate 1636 can include a one-way valve configured to prevent the escape of fluids.

In some configurations, the plate 1636 can be adapted for the introduction of the camera 1500 described herein. For example, the plate 1636 can include an opening specifically designed for the flexible cord 1516 to prevent the escape of fluids around the cord 1516. The opening can be offset from the center of the plate 1636. The plate 1636 can be adapted for use with any port, including, but not limited to the adjustable port 1600 or the GelPort®.

Insertion Tip

As mentioned above, the minimally invasive surgical procedure can include the use of an insertion tip to create one or more openings in the abdominal wall. The insertion tip can be secured to the handle portion using any of the connection features described herein. For example, as shown in FIGS. 18A-18C, the insertion tip 1800 can include a tip portion 1888 having a sharpened distal tip capable of forming an incision. The tip portion 1888 can define a lumen capable of engaging the shaft portion 1802 and/or push rod 1804. For example, the lumen can have a varying diameter, a reduced diameter portion capable of threadably engaging a threaded portion 1872 of the push rod 1804 and a larger diameter portion capable of threadably engaging a threaded portion 1874 of the shaft portion 1802. The tip portion 1888 can include a length between about 5 mm and about 12 mm, preferably between about 10 mm to 11 mm.

Although not shown, the tip portion 1888 can include a proximal tubular portion defining the lumen for engaging the shaft portion and/or push rod. In this configuration, the tip portion 1888 can include a distal tip portion having a sharpened blade for forming incisions.

In use, the insertion tip 1800 can be secured to the shaft portion and then used to form the incision. Once the incision has been created, the entire insertion tip can be removed and the insertion tip can be replaced with a different working end. Alternatively, the insertion tip can be introduced through an umbilicus opening and back out of the abdomen. Thereafter, the insertion tip can be replaced with a different working end.

In some scenarios, it may desirable for the insertion tip to include a retractable tip portion or include a retractable sheath (not shown). These retractable safety tips can prevent injury when the tip is not in use and shield the tip portion when the tip portion is inside the abdomen.

With the retractable tip portion, similar to the insertion tip 1800, these retractable safety tips can be secured to the shaft portion using the same threaded features. The tip portion can define a lumen extending through at least a distal portion of the tip portion. The lumen can be configured to receive a spring-loaded shield or otherwise retractable shield. At least a distal portion of the shield can extend outward from the distal end of the tip portion to protect the sharpened tip of the tip portion. During use, when pressure is applied to the distal tip of the tip portion (e.g., when forming the incision), the shield can retract into the lumen to release the sharpened tip. After the sharpened tip forms the incision and enters the abdomen, the shield can move distally to cover the sharpened tip.

With the retractable sheath configuration, the tip portion can connect to a retractable sheath portion configured to retract at least partially over the shaft portion when pressure is applied to the distal tip of the sheath (e.g., when forming incision). When the sheath retracts, the insertion tip can form the incision.

As used herein, the relative terms "proximal" and "distal" shall be defined from the perspective of the surgical tool. Thus, proximal refers to the direction of the handle portion of the surgical tool and distal refers to the direction of the working end.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Various embodiments have been disclosed above. These various embodiments may be used alone or in combination, and various changes to individual features of the embodiments may be altered, without departing from the scope of the invention. For example, the order of various method steps may in some instances be changed, and/or one or more optional features may be added to or eliminated from a described device. Therefore, the description of the embodiments provided above should not be interpreted as unduly limiting the scope of the invention as it is set forth in the claims.

What is claimed is:

1. A scarless surgical tool comprising:
   a handle portion comprising:
   a central shaft; and
   a plurality of stabilizing shafts surrounding the central shaft, the plurality of stabilizing shafts being positioned with respect to the central shaft such that the plurality of stabilizing shafts puncture skin prior to or simultaneously with entrance of the central shaft through the punctured skin; and
   a working end configured to be removably secured to the handle portion, the working end comprising:
   a proximal portion configured to receive each of the plurality of stabling shafts and the central shaft of the handle portion; and
   a distal portion comprising a tool portion, the central shaft configured to control movement of the tool portion when the working end is secured to the handle portion, each of the plurality of stabilizing shafts carrying cables configured to facilitate functionality of the tool portion of the working end.

2. The scarless surgical tool of claim 1, wherein the proximal portion of the working end comprises a securing member configured to receive each of the plurality of stabilizing shafts.

3. The scarless surgical tool of claim 1, wherein each of the plurality of stabilizing shafts has a diameter of less than or equal to about 1.0 mm.

4. The scarless surgical tool of claim 1, wherein each of the stabilizing shafts has a sharpened distal tip capable of forming an opening.

5. The scarless surgical tool of claim 1, wherein a length of the central shaft is longer than a length of each of the plurality of stabilizing shafts.

6. The scarless surgical tool of claim 1, wherein the working end comprises a locking mechanism configured to fix the position of the plurality of stabilizing shafts relative to each other.

7. The scarless surgical tool of claim 6, wherein the locking mechanism comprises a retaining ring configured to secure a connection between the plurality of stabilizing shafts and the working end.

8. The scarless surgical tool of claim 1, wherein the tool portion is graspers, and wherein axial movement of the central shaft can move the graspers between an open configuration and a closed configuration.

9. The scarless surgical tool of claim 1, wherein each of the plurality of stabilizing shafts comprises a notch at a distal portion of each of plurality of stabilizing shafts.

10. The scarless surgical tool of claim 1, wherein each of the plurality of stabilizing shafts is solid.

\* \* \* \* \*